United States Patent
Sabovic

(10) Patent No.: US 9,498,464 B2
(45) Date of Patent: Nov. 22, 2016

(54) TREATMENT OF ARTERIAL WALL BY COMBINATION OF RAAS INHIBITOR AND HMG-COA REDUCTASE INHIBITOR

(71) Applicant: ARTSKIN d.o.o., Logatec (SI)

(72) Inventor: Miso Sabovic, Ljubljana (SI)

(73) Assignee: ARTSKIN D.O.O., Logatec (SI)

( * ) Notice: Subject to any disclaimer, the term of this patent is extended or adjusted under 35 U.S.C. 154(b) by 0 days.

(21) Appl. No.: 14/363,550

(22) PCT Filed: Dec. 7, 2012

(86) PCT No.: PCT/EP2012/005074
§ 371 (c)(1),
(2) Date: Jun. 6, 2014

(87) PCT Pub. No.: WO2013/083286
PCT Pub. Date: Jun. 13, 2013

(65) Prior Publication Data
US 2014/0323536 A1  Oct. 30, 2014

(30) Foreign Application Priority Data

Dec. 9, 2011  (SI) .................................. 201100459
Aug. 27, 2012 (SI) .................................. 201200268

(51) Int. Cl.
| A61K 31/41 | (2006.01) |
| A61K 31/40 | (2006.01) |
| A61K 45/06 | (2006.01) |
| A61K 31/405 | (2006.01) |

(52) U.S. Cl.
CPC ............ *A61K 31/40* (2013.01); *A61K 31/405* (2013.01); *A61K 31/41* (2013.01); *A61K 45/06* (2013.01)

(58) Field of Classification Search
USPC .......................................................... 514/381
See application file for complete search history.

(56) References Cited

U.S. PATENT DOCUMENTS

| 7,932,263 B2 * | 4/2011 | Mehta ............................ 514/279 |
| 2003/0049314 A1 * | 3/2003 | Liang et al. .................. 424/465 |
| 2004/0259925 A1 * | 12/2004 | Riedel et al. ................. 514/381 |
| 2010/0074951 A1 * | 3/2010 | Kim et al. ..................... 424/476 |
| 2011/0190277 A1 * | 8/2011 | Riedel et al. ............... 514/223.5 |

FOREIGN PATENT DOCUMENTS

| WO | WO 2004/062557 | 7/2004 |
| WO | WO 2006/105806 | 10/2006 |
| WO | WO 2009/134076 | * 11/2009 |
| WO | WO 2012/116985 | 9/2012 |

OTHER PUBLICATIONS

Maejima et al., Circulation Journal, Mar. 2011, 75:589-595.*

Anderson et al., "An Updated Coronary Risk Profile. A Statement for Health Professionals," *Circulation*, vol. 83, 1991, pp. 356-362.
Basta et al., "Advanced Glycation End Products and Vascular Inflammation: Implications for Accelerated Atherosclerosis in Diabetes," *Cardiovascular Research*, vol. 63, 2004, pp. 582-592.
Blum et al., "The Pleiotropic Effects of Statins on Endothelial Function, Vascular Inflammation, Immunomodulation and Thrombogensis," *Atheroscherosis*, vol. 203, 2009, pp. 325-330.
Bowness, J. Michael, "Atherosclerosis and Aging of the Arterial Wall," *Can Med Assoc J*, vol. 147, No. 2, 1992, p. 201.
Carerj et al., "Normal Vascular Aging Evaluated by a New Tool: E-Tracking," *Echocardiography*, vol. 1, 2006, p. S49.
Corretti et al., "Guidelines for the Ultrasound Assessment of Endothelial-Dependent Flow-Mediated Vasodilation of the Brachial Artery," *J Am Coll Cardiol*, vol. 39, 2002, pp. 257-265.
Horiuchi et al, "Fluvastatin Enhances the Inhibitory Effects of a Selective Angiotensin II Type Receptor Blocker, Valsartan on Vascular Neointimal Formation," *Circulation*, vol. 107, 2003, pp. 106-112.
Ichihara et al., "Fluvastatin Prevents Development of Arterial Stiffness in Haemodialysis Patients with Type 2 Diabetes Mellitus," *Nephrol Dial Transplant*, vol. 17, 2002, pp. 1513-1517.
Jankowski et al., "Pleiotropic Effects of Drugs Inhibiting the Renin-Angiotensin-Aldosterone System," *Current Pharmaceutical Design*, vol. 15, 2009, pp. 571-584.
Jurasic et al., "Beta Stiffness-Setting Age Standards," *Acta Clin Croat*, vol. 48, 2009, pp. 253-258.
Kannel, William B., "Risk Stratification in Hypertension: New Insights from the Framingham Study," *Am J Hypertens*, vol. 1, No. 3, 2000.
Karalliedde et al., "Valsartan Improves Arterial Stiffness in Type 2 Diabetes Independently of Blood Pressure Lowering," *Hypertension*, vol. 51, 2008, pp. 1617-1623.
Kim et al., "The Effect of an Angiotensin Receptor Blocker on Arterial Stiffness in Type 2 Diabetes Mellitus Patients with Hypertension," *Diabetes Metab J*, vol. 35, No. 3, Jun. 2011, pp. 236-242.
Lee et al., "Aging and Arterial Stiffness," *Circulation Journal*, vol. 94, 2010, pp. 2258-2262.
Lunder et al., Subtherapeutic, Low-Dose Fluvastatin Improves Functional and Morphological Arterial Wall Properties in Apparently Healthy, Middle-Aged Males—A Pilot Study, *Atherosclerosis*, vol. 215, No. 2, 2010, pp. 446-451.
Lunder et al., "Reduction of Age-Associated Arterial Wall Changes by Low-Dose Valsartan," *European Journal of Cardiovascular Prevention & Rehabilitation*, 2011, pp. 1-6.
Mancini et al., "Reduction of Morbidity and Mortality by Statins, Angiotensin-Converting Enzyme Inhibitors, and Angiotensin Receptor Blockers in Patients with Chronic Obstructive Pulmonary Disease," *Journal of the American College of Cardiology*, vol. 47, 2006, pp. 2554-2560.
Mitchell et al., "Arterial Stiffness and Cardiovascular Events: The Framingham Heart Study," *Circulation*, vol. 121, 2010, pp. 505-511.
Najjar et al., "Arterial Aging: Is it an Immutable Cardiovascular Risk Factor?," *Arterial Aging, Hypertension*, vol. 46, 2005, pp. 454-462.

(Continued)

*Primary Examiner* — Rei-Tsang Shiao

(74) *Attorney, Agent, or Firm* — Mueting, Raasch & Gebhardt, P.A.

(57) ABSTRACT

The present invention relates to a pharmaceutical combination composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having at least one cardiovascular disorder or having at least one risk factor for cardiovascular disorder.

6 Claims, 12 Drawing Sheets

(56) References Cited

OTHER PUBLICATIONS

Figure 1:
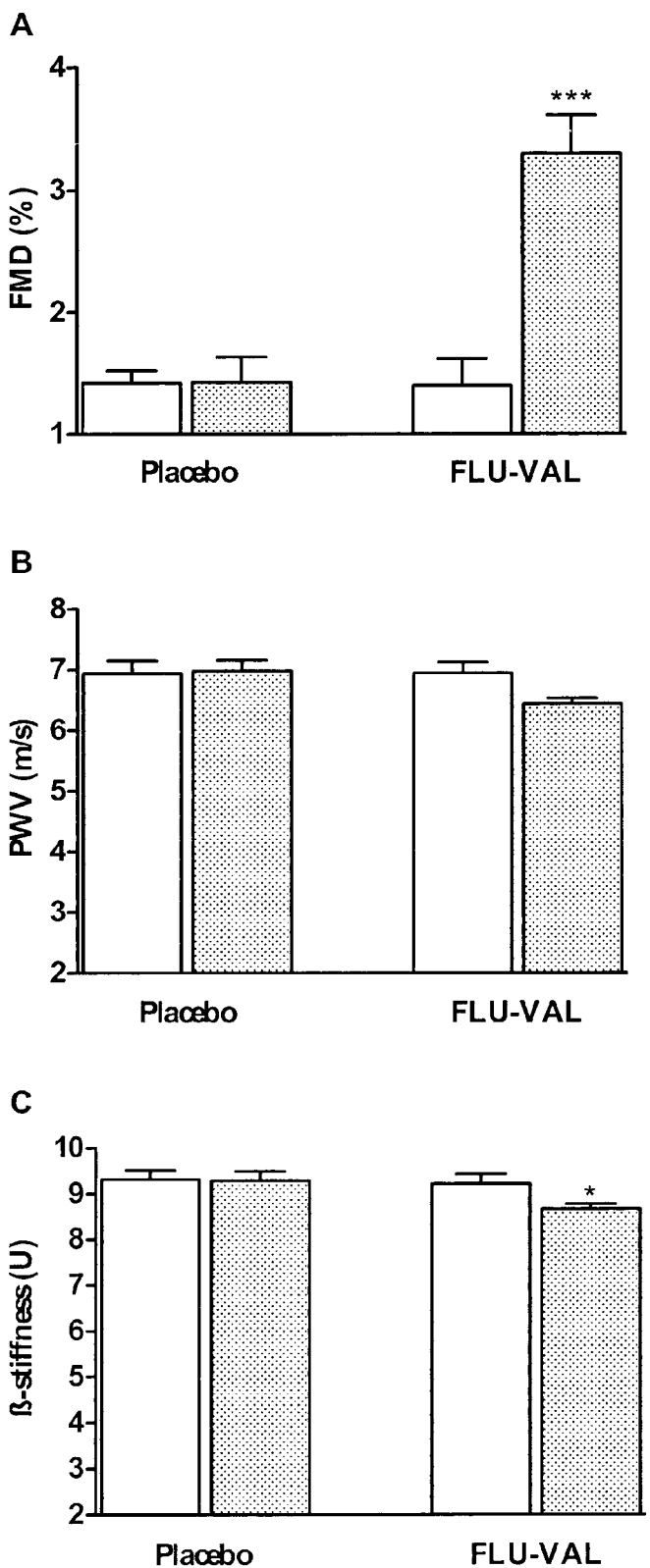

Nakamura et al., "Selective Angiotensin Receptor Antagonism with Valsartan Decreases Arterial Stiffness Independently of Blood Pressure Lowering in Hypertensive Patients," *Hypertension Research Clinical and Experimental, Osaka, JP*, Vo. 28, No. 12, 2005, pp. 937-943.

Nickenig, Georg, "Should Angiotensin II Receptor Blockers and Statins be Combined", *Circulation*, vol. 110, 2004, pp. 1013-1020.

Sander et al., "Hypertension and Lipids: Lipid Factors in the Hypertension Syndrome," *Curr Hypertens Rep*, vol. 4, 2002, pp. 458-463.

Sinigoj et al., "The Preventive Cardiovascular Effect of a Combination of Statin and Angiotensin Receptor Blocker at Sub-Therapeutic Doses in Middle-Aged Healthy Volunteers," *BMC Pharmacology*, 2009, 9 (Suppl. 2):A63.

Suzuki et al., "Combination Therapy of Candesartan with Statin Inhibits Progression of Atherosclerosis More than Statin Alone in Patients with Coronary Artery Disease," *Coronary Artery Disease*, vol. 22, No. 5, 2011, pp. 352-358.

Yamamoto et al., "Pravastatin Enhances Beneficial Effects of Ahmesartan on Vascular Injury of Salt-Sensitive Hypertensive Rats, via Pleiotropic Effects," *Arteriosclerosis, Thrombosis, and Vascular Biology*, vol. 27, 2007, pp. 556-563.

Yoshikawa et al., "Effects of Combined Treatment with Angiotensin II Type 1 Receptor Blocker and Statin on Stent Restenosis," *J Cardiovasc Pharmacol*, vol. 53, No. 2, 2009, pp. 179-186.

Zhen et al., "Fluvastatin Enhances the Inhibitory Effects of a Selective $AT_1$ Receptor Blocker, Valsartan, on Atherosclerosis," *Hypertension*, vol. 44, 2004, pp. 758-763.

"Third Report of the National Cholesterol Education Program (NCEP) Expert Panel on Detection, Evaluation, and Treatment of High Blood Cholestrol in Adults (Adult Treatment Panel III) Final Report," *Circulation*, vol. 106, 2002, pp. 3143-3421.

\* cited by examiner

A

B

C

A

B

C

A

B

C

A

B

C

A

B

C

A

B

C

US 9,498,464 B2

TREATMENT OF ARTERIAL WALL BY COMBINATION OF RAAS INHIBITOR AND HMG-COA REDUCTASE INHIBITOR

This application is a U.S. National Stage Application of International Application No. PCT/EP2012/005074 filed Dec. 7, 2012, which was published in English on Jun. 13, 2013 as International Patent Publication WO 2013/083286 A1. International Application No. PCT/EP2012/005074 also claims priority to Slovenian Application Nos. P-201100459, filed Dec. 9, 2011 and P-201200268, filed Aug. 27, 2012.

FIELD OF INVENTION

The present invention relates to a pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall, for use in the prevention, reduction or reversal of arterial aging, and/or for use in decreasing the worsening of the occurrence of cardiovascular disorders in unhealthy subjects. Furthermore, the pharmaceutical composition according to the invention is also suitable for use in maintaining or improving the functional and morphological properties of the arterial wall, for use in the prevention, reduction or reversal of arterial aging, and/or for use in decreasing the worsening or the occurrence of cardiovascular disorders in subjects having at least one cardiovascular disorder and/or subjects having at least one risk factor for a cardiovascular disorder.

BACKGROUND OF INVENTION

Ageing (British English) or aging (American English) is the accumulation of changes in an organism or object over time. Aging in humans refers to a multidimensional process of physical, psychological and social change. Aging is defined as the gradual biological impairment of normal function, probably as a result of changes made to cells, molecules and tissues/morphological components. These changes have a direct impact on the functional ability of organs such as for example the heart, brain, kidney and lungs, biological systems such as for example the nervous, digestive and reproductive system and ultimately the organism as a whole.

Although aging affects the whole body the consequences of aging are related to the involved organ or system. The aging of arteries produces the most detrimental consequences of aging. Aging causes progressive decline in physiological arterial functions and morphology. Aging arteries generate changes in hemodynamic that importantly contribute to the development of cardiovascular diseases. In addition, aging arteries are more susceptible for the development of certain conditions such as atherosclerosis. Taken all facts together, arterial aging substantially contributes to the development and worsening of cardiovascular diseases such as for example myocardial infarction, stroke, dementia, critical limb ischemia, aortic aneurism, and similar. Thus, aging, specifically arterial aging, is one of most important risk factors for the development and worsening of cardiovascular diseases. It is widely believed that aging per se is not a modifiable risk factor. This conclusion does not necessarily apply to the arterial aging, however. Cardiovascular diseases remain the leading cause of morbidity and mortality in developed countries despite current intensive management strategies. Importantly, up to date, no effective treatment that would be able to prevent, reduce or even reverse the process of arterial aging has been disclosed.

Arterial aging is characterized by alterations in cells, matrix, and biomolecules present in the arterial wall. Arterial aging is a foundation for the initiation and progression of cardiovascular diseases. Although arterial aging literary starts immediately after birth, it seems that important age-related changes occur at middle age. In this period (approximately between 20-65 years) age-related changes gradually and continuously progress. Basic representative functional and morphological age-related arterial changes are for example endothelial dysfunction, vascular smooth muscle cell proliferation/invasion/secretion, matrix fragmentation, collagenisation and glycation that result in typical age related changes such as for example increased arterial stiffness and decreased arterial wall elasticity. Age-associated arterial wall phenotype creates a microenvironment enriched with reactive oxygen species and inflammatory molecules. Several age-modified angiotensin II signaling molecules control and facilitate the processes producing age-related arterial changes. Age-related arterial changes are clinically silent, but as described above may lead to development and worsening of cardiovascular diseases. Targeting arterial age/aging can reduce the incidence/occurrence and progression of said cardiovascular diseases.

Arterial aging is a result of gradual changes of morphological (i.e. structural) and functional properties of the arterial wall. The arterial wall consists of three layers: intima, media and adventia. The most inner part of the arterial wall is endothelium (a part of intima), which is directly exposed to the blood in the artery lumen. There is a large amount of evidence providing that aging itself induces the stiffening of media and consequently the stiffening of whole arterial wall (morphological property) and the impairment of endothelial function (functional property).

On the other hand, it is well known in the art that the functional and morphological properties of the arterial wall are also negatively influenced, if a subject has a cardiovascular disorder or a risk factor for a cardiovascular disorder. In fact, arterial aging may be accelerated, if a subject has a cardiovascular disorder or a risk factor for a cardiovascular disorder.

It is well known in the art that arterial stiffness and endothelial dysfunction are among the most important mechanisms facilitating the development and worsening of cardiovascular disorders such as hypertension, myocardial infarction, stroke, dementia, and similar. As regards the correlation between arterial aging, arterial stiffness, and cardiovascular risks, Mitchell at al. have found that increased arterial stiffness is a marker of increased cardiovascular risk, and arterial stiffness increases by aging. (Mitchell G F et al., Arterial stiffness and cardiovascular events: The Framingham Heart Study. Circulation 2010; 121:505-11). Thus, arterial aging, in particular affecting the gradual increase of arterial stiffness, increases the risk for cardiovascular disorders.

It is also well known in the art that one has to distinguish between arterial aging in apparently healthy subjects and arterial aging in connection with cardiovascular diseases (Najjar S. S. et al., Arterial Aging, Hypertension 2005; 46:454-462). When discussing apparently healthy subjects, Najjar et al. describe the changes in the arterial structure and function as part of "normative aging", whereas when discussing cardiovascular diseases, they refer to accelerated changes which is not comparable to normative aging. Furthermore, J. M. Bowness reports that changes in the composition of the extracellular matrix associated with normal aging are clearly different from those occurring in the development of advanced atherosclerotic lesions (J. M. Bowness, Atherosclerosis and aging of the arterial wall, Can Med Assoc J 1992; 147(2):201). Moreover, H.-Y. Lee et al. disclose that arterial walls stiffen with age and that this aging process in the arterial tree is heterogeneous, with distal arteries not exhibiting these stiffening changes, which is different from the atherosclerotic process (H.-Y. Lee et al., Circulation Journal 2010; 94; 2258-2262).

Thus, arterial aging is different in unhealthy and healthy subjects, wherein unhealthy subjects are subjects e.g. having at least one cardiovascular disorder or having a risk factor for a cardiovascular disorder, and healthy subjects are subjects not having a cardiovascular disorder. Since arterial aging is typically correlated with a deterioration of the functional and morphological properties of the arterial wall, it can be concluded that also the properties of the arterial wall are affected depending on whether the subject is unhealthy (e.g. has a cardiovascular disorder) or healthy (e.g. does not have a cardiovascular disorder). On the other hand, both, arterial aging and deterioration of the properties of the arterial wall, facilitate the development and worsening of cardiovascular disorders.

The renin-angiotensin-aldosterone system (RAAS) plays an important role in regulating blood volume and systemic vascular resistance, which together influence cardiac output and arterial pressure. As the name implies, there are three important components to this system: renin, angiotensin, and aldosterone. Renin, which is primarily released by the kidneys, stimulates the formation of angiotensin in blood and tissues, which in turn stimulates the release of aldosterone from the adrenal cortex. When renin is released into the blood, it acts upon a circulating substrate, angiotensinogen, that undergoes proteolytic cleavage to form the decapeptide angiotensin I. Vascular endothelium, particularly in the lungs, has an enzyme, angiotensin converting enzyme (ACE), that cleaves off two amino acids to form the octapeptide, angiotensin II (AII), although many other tissues in the body (heart, brain, vascular) also can form AII.

Renin inhibitors are antihypertensive drugs that inhibit the first and rate-limiting step of RAAS. Since the 1970s scientists have been trying to develop potent inhibitors with acceptable oral bioavailability. The first and second generations faced problems like poor bioavailability and lack of potency. The third generation is non-peptidic renin inhibitors with acceptable oral bioavailability and potency for clinical use in the treatment of hypertension.

Angiotensin-converting enzyme (ACE) inhibitors produce vasodilation by inhibiting the formation of angiotensin II. This vasoconstrictor is formed by the proteolytic action of renin (released by the kidneys) acting on circulating angiotensinogen to form angiotensin I. Angiotensin I is then converted to angiotensin II by angiotensin converting enzyme. ACE inhibitors also break down bradykinin (a vasodilator substance). Therefore, ACE inhibitors, by blocking the breakdown of bradykinin, increase bradykinin levels, which can contribute to the vasodilator action of ACE inhibitors. ACE inhibitors are used primarily to treat hypertension, they may also be prescribed for cardiac failure, diabetic nephropathy, renal disease, systemic sclerosis, left ventricular hypertrophy and other disorders. ACE inhibitors are often used in conjunction with a diuretic in treating hypertension and heart failure.

Angiotensin II receptor antagonists, also known as angiotensin receptor blockers (ARBs), AT1-receptor antagonists or sartans, are a group of pharmaceuticals which modulate the renin-angiotensin-aldosterone system. Their main use is in hypertension (high blood pressure), diabetic nephropathy (kidney damage due to diabetes), congestive heart failure, proteinuria, and prevention of cardiac remodeling after myocardial infarction. ARBs are receptor antagonists that block type 1 angiotensin II ($AT_1$) receptors on bloods vessels and also in other tissues as arterial wall and heart muscle. ARBs act on the surface and inside arterial wall.

HMG-CoA reductase inhibitors also known as statins are a class of drug used to lower cholesterol levels by inhibiting the enzyme HMG-CoA reductase that is the rate-controlling enzyme (EC 1.1.1.88) of the mevalonate pathway, the metabolic pathway that produces cholesterol and other isoprenoids. HMG-CoA reductase enzyme plays a central role in the production of cholesterol in the liver. Statins are among the most commonly prescribed drugs in medicine. Clinical studies have shown that statins significantly reduce the risk of heart attack and death in patients with proven coronary artery disease (CAD), and can also reduce cardiac events in patients with high cholesterol levels who are at increased risk for heart disease.

It is known that angiotensin II receptor antagonists and HMG-CoA reductase inhibitors posses the so called pleiotropic effects, this means effects beyond their primary action. Pleiotropic effects of a drug are actions other than those for which the agent was specifically developed. These effects may be related to or unrelated to the primary mechanism of action of the drug, and they are usually unexpected. As arterial-associated pleiotropic effects, both, angiotensin II receptor antagonists and HMG-CoA reductase inhibitors, could possibly improve endothelial function, they could act as antioxidants, they could have immunomodulatory effects, they could have anti-proliferative and anti-remodeling effects and similar beneficial vascular pleiotropic effects (Blum A et al. Atherosclerosis 2009; 203:325-30 and Jankowski P et al. Curr Pharm Des 2009; 15: 571-84).

Coronary heart disease (CHD) resulting from atherosclerosis is the single largest cause of death and approximately 40% of patients with hypertension have hypercholesterolemia, which is central to the pathogenesis of atherosclerosis and cardiovascular disease (CVD) (Kannel W B et al, Am J Hypertens 2000; 1:3; S-10S). Conversely, hypertension is a significant risk factor in patients with elevated cholesterol and there is a strong synergy between hypertension and hypercholesterolemia in terms of risk factors for the development of CVD (Sander G E, et al, Curr Hypertens Rep 2002; 4:458-463). Nickenig George, Circulation 2004, 110: 1013-1020 teaches on theoretical level that combination therapy of an ARB and an HMG-CoA reductase inhibitor would find utilization in people with cardiovascular risk factors and provocatively, also in people without symptomatic disease, but who are more than 55 years old, as age also becomes a risk factor for CVDs. Moreover, patients with two or more linked risk factors for CVD (such as for example type 2 diabetes mellitus, stroke, heart failure, metabolic syndrome and similar) would benefit from the combination of cholesterol lowering and antihypertensive drug therapy as well. The author concluded that further studies and combination in one pill would be appealing with respect to the efficient prevention of cardiovascular end points and would potentially increase treatment adherence in patients who have been prescribed long term poly-medication therapy.

Investigations carried by Zhen Li et al, Hypertension 2004; 44:758-763 suggested that concomitant $AT_1$ receptor and cholesterol biosynthesis blockade blunts oxidative stress and inflammation independent of blood pressure or cholesterol-related effects. They examined the possibility that statins may enhance the beneficial effects of an ARB on atherosclerosis. The study demonstrated that the combination of fluvastatin (well known representative of HMG-CoA reductase inhibitor) with valsartan (well known representative of ARB) has a preventive function regarding the development of atherosclerotic lesions. When 'knockout' mice that were fed with high caloric diet and that were consequently very susceptible to development of atherosclerosis received fluvastatin and valsartan at the beginning of parallel feeding, a decrease in observed atherosclerosis lesions size was found in comparison to the animals that did not receive the combination of fluvastatin and valsartan. These observations showed that the combination of fluvastatin and valsartan could prevent to the some degree development of atherosclerosis, but did not show that it might induce the reversal of already present atherosclerotic plaques. Therefore, the authors showed the possible protective effect of the combination but not the reversal effect of the same combination. From the clinical perspective it could be concluded that the authors showed only protective effects of the combination which could be applied only to subjects without any pathological changes whereas they did not show that the combination could induce the reversal of already present pathological changes.

Eiichiro Yamamoto et al, Arterioscler Thromb Vasc Biol 2007, 27:556-563 report that the combination of an ARB with an HMG-CoA reductase inhibitor may be the potential therapeutic strategy for vascular diseases of salt-sensitive hypertension. Their studies show that the combination of olmesartan (well known representative of ARB) and pravastatin (well known representative of HMG-CoA reductase inhibitor) exerts beneficial vascular effects in salt-sensitive hypertension, via differential pleiotropic effects and that pravastatin enhances vascular protective effects of olmesartan.

The report of Suzuki, Takayuki et al, Coronary Artery Disease: August 2011—Volume 22—Issue 5—p 352-358 discloses that the combination therapy of candesartan (well known representative of ARB) with an HMG-CoA reductase inhibitor inhibits progression of atherosclerosis more than HMG-CoA reductase inhibitor alone in patients with coronary artery disease.

From Yoshikawa M. et al, J Cardiovasc Pharmacol. 2009 February; 53(2):179-86 it is known that the combined treatment with an ARB and an HMG-CoA reductase inhibitor after stenting is useful for preventing stent restenosis.

G. B. John Mancini, et al, J Am Coll Cardiol, 2006; 47:2554-2560 report that the combination of ARBs and HMG-CoA reductase inhibitors reduced both cardiovascular (CV) and pulmonary outcomes. This combination was associated with a reduction in chronic obstructive pulmonary disease (COPD) hospitalization and total mortality not only in the high CV risk cohort but also in the low CV risk cohort. The combination also reduced myocardial infarction (MI) in the high CV risk cohort.

Atsuro Ichihara et al, Nephrol Dial Transplant (2002) 17: 1513-1517 in their study show on a relatively small number of patients (22 patients) in an observation period of 6 months that fluvastatin therapy (20 mg/day) reduces arterial stiffness, as measured by PWV (pulse-wave velocity), in haemodialysis patients with type 2 diabetes mellitus even if their serum lipid levels are within the normal ranges. The authors concluded that long-term administration of fluvastatin prevents further worsening of arterial biomechanics in haemodialysis patients with type 2 diabetes mellitus even in the presence of serum lipid levels in the normal range.

The first report on improvement in artery elasticity with an ARB was prepared by Janaka Karalliedde et al, Hypertension 2008, 51:1617-1623. The authors examined whether the ARB valsartan combined with hydrochlorothiazide (HCTZ) would improve arterial stiffness to a greater extent than an equivalent antihypertensive drug, the calcium channel blocker amlodipine in patients having type 2 diabetes mellitus with systolic hypertension and albuminuria. The 24-week single center, randomized, double-blind study (after a 4-week washout phase HCTZ 25 mg/daily was added to valsartan 160 mg—the maximum dose licensed for use in the UK) shows that the combination valsartan and hydrochlorothiazide improves arterial stiffness (measured by aortic PWV) and albumin excretion rate (marker of kidney disease) to a significantly greater extent than amlodipine.

A multi-centre, open label, controlled study performed by Ji Hyun Kim et al, (Diabetes Metab J. 2011 June; 35(3): 236-242) shows that 12 weeks treatment with angiotensin receptor blocker such as for example valsartan (an initial daily dose of 80 mg of valsartan was increased after 4 weeks to 160 mg/day for remaining 8 weeks) improves arterial stiffness (measured by pulse wave analysis) in patients with type 2 diabetes and hypertension, and that the glucose status at baseline is associated with this effect. The authors concluded that valsartan may be useful for delaying and reducing the influence of cardiovascular risk factors on arterial stiffness in high-risk patients such as those with both type 2 diabetes and hypertension.

Horiuchi et al, Circulation, 2003; 107: 106-112 demonstrates that a combination of low dose valsartan and low-dose fluvastatin acted synergistically to attenuate vascular neointimal formation at doses that were without effect when administered alone and were devoid of any effects on blood pressure or cholesterol levels.

Recent $3^{rd}$ International Conference on Fixed Combination in the Treatment of Hypertension, Dyslipidemia and Diabetes Mellitus (November 2010) taught about several fixed combination products for the treatment of hypertension or hyperlipidemia, that have already been successfully placed on the market. None of the marketed combination product comprises RAAS inhibitor and HMG-CoA reductase inhibitor despite many literature providing beneficial effects of said combination. In addition, it was presented that of 1200 combinations reported in different studies only 45 were rated 'effective', what represents only 3.75%.

Therefore, the usefulness and effectiveness of combination of RAAS inhibitor and an HMG-CoA reductase inhibitor in the treatment of coronary and cardiovascular disorders has already been demonstrated in the studies of prior art. However, none of the studies teaches or describes or even gives any hint that a pharmaceutical composition comprising at least one RAAS inhibitor and at least one HMG-CoA reductase inhibitor, wherein the RAAS inhibitor and the HMG-CoA reductase inhibitor are each only present in a subtherapeutic daily dose, could be used for achieving a positive effect on functional and morphological properties of the arterial wall in a subject having at least one cardiovascular disorder or having at least one risk factor for cardiovascular disorder. Moreover, none of the studies describes or teaches or even gives any hint that a pharmaceutical composition comprising at least one RAAS inhibitor in a subtherapeutic daily dose and at least one HMG-CoA reductase inhibitor in a subtherapeutic daily dose could be used for the prevention, reduction and/or reversal of arterial aging and/or in decreasing the worsening or the occurrence of cardiovascular disorders in a subject having at least one cardiovascular disorder or having at least one risk factor for cardiovascular disorder. Moreover, the prior art literature does not relate to the dose dependent (dose-response) effect on arterial wall properties.

At the time being there is a general belief that the main strategy in treating or preventing cardiovascular disorders is to reduce the risk factors such as for example hypertension, hyperlipidemia, diabetes, smoking, but not to treat arterial wall directly in order to achieve the decrease of further impairment of arterial wall changes. Therefore, until now there is no treatment available which could reverse pathological arterial wall changes in subjects having at least one cardiovascular disorder or having at least one risk factor for cardiovascular disorder while there is a general belief that the above mentioned arterial wall changes are definitely irreversible and that the aim of treatment could be only the decrease of rate of further impairment. Therefore, novel approaches for maintaining or improving the functional and morphological properties of the arterial wall in subjects having at least one cardiovascular disorder or having at least one risk factor for a cardiovascular disorder are of great interest. Since the arterial wall properties are often also correlated with arterial age, there is also a need for a novel approach for preventing, reducing or reversing arterial aging in these subjects.

Apparently, novel approaches and strategies in treating cardiovascular disorders are of great interest. Therefore, the approach that is focused on the properties of arterial walls, particularly on functional and morphological properties and on arterial aging, that allows the preventing, reducing, or reversal of arterial changes would be a significant contribution to the art.

Furthermore, in view of the fact that active agents in pharmaceutical compositions may also cause negative side-effects, it is advantageous to use rather low doses of active agents in pharmaceutical compositions for the purpose of the invention.

In addition, due to long term persistence of beneficial arterial properties it is advantageous to use rest-period between two treatments for the purpose of the invention in order to prevent the occurrence of 'resistance'. Moreover, there is no data in literature about possible prolonged effect in arterial functions after discontinuation of the treatment.

It is well-known that diabetes type I and type II induce accelerated and progressive impairment of functional and morphological properties of arterial wall and accelerate arterial aging. As the consequence, the occurrence or worsening of cardiovascular disorders in diabetic patients is facilitated leading to increased cardiovascular morbidity/mortality. The author of the present invention has clearly shown that a subtherapeutic daily dose combination of at least one renin-angiotensin-aldosterone system inhibitor and at least one HMG-CoA reductase inhibitor successfully improves (impaired) functional and morphological properties of the arterial wall, reduces or reverses the arterial aging and decreases the worsening or the occurrence of cardiovascular disorders in diabetic patients. It is important to emphasize that a subtherapeutic daily dose combination of at least one renin-angiotensin-aldosterone system inhibitor and at least one HMG-CoA reductase inhibitor treats the complication of diabetes (injured arterial wall), but not diabetes itself.

SUMMARY OF THE INVENTION

The above mentioned objects of the present invention are surprisingly achieved by providing a pharmaceutical composition comprising at least one renin-angiotensin-aldosterone system inhibitor in a subtherapeutic daily dose and at least one HMG-CoA reductase inhibitor in a subtherapeutic daily dose. Since the composition is suitable for use in maintaining or improving the functional and morphological properties of the arterial wall and in the prevention, reduction or reversal of arterial aging, it is also suitable for use in decreasing the worsening or the occurrence of cardiovascular disorders. Surprisingly, all the above mentioned effects are achieved in a substantial amount in unhealthy subjects, i.e. subjects having a risk for a coronary heart disease (CHD risk factor, 10 year) according to the Framingham Risk Score of more than 10%, in subjects already having at least one cardiovascular disorder and/or in subjects having at least one risk factor for the development of a cardiovascular disorder.

In one aspect, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in maintaining or improving the functional and morphological properties of the arterial wall in unhealthy subjects.

In another aspect, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in the prevention, reduction or reversal of arterial aging in unhealthy subjects.

In another aspect, the present invention is directed to pharmaceutical composition comprising at least one renin-angiotensin-aldosterone system inhibitor in a subtherapeutic daily dose, and at least one HMG-CoA reductase inhibitor in a subtherapeutic daily dose, for use in decreasing the worsening or the occurrence of cardiovascular disorders in unhealthy subjects.

In another aspect, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in maintaining or improving the functional and morphological properties of the arterial wall in subjects having at least one cardiovascular disorder.

In another aspect, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in the prevention, reduction or reversal of arterial aging in subjects having at least one cardiovascular disorder.

In another aspect, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in decreasing the worsening or the occurrence of cardiovascular disorders in subjects having at least one cardiovascular disorder.

In another aspect, the present invention is directed to pharmaceutical composition comprising at least one renin-angiotensin-aldosterone system inhibitor in a subtherapeutic daily dose, and at least one HMG-CoA reductase inhibitor in a subtherapeutic daily dose, for use in maintaining or improving the functional and morphological properties of the arterial wall in subjects having at least one risk factor for a cardiovascular disorder.

In another aspect, the present invention is directed to a pharmaceutical composition comprising at least one reninangiotensin-aldosterone system inhibitor in a subtherapeutic daily dose, and at least one HMG-CoA reductase inhibitor in a subtherapeutic daily dose, for use in the prevention, reduction or reversal of arterial aging in subjects having at least one risk factor for a cardiovascular disorder.

In another aspect, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in decreasing the worsening or the occurrence of cardiovascular disorders in subjects having at least one risk factor for a cardiovascular disorder.

In yet another aspect, the present invention is directed to a pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having at least one cardiovascular disorder or having at least one risk factor for cardiovascular disorder.

In yet another aspect, the present invention is directed to a pharmaceutical composition comprising at least one renin-angiotensin-aldosterone system inhibitor in a subtherapeutic daily dose and at least one HMG-CoA reductase inhibitor in a subtherapeutic daily dose for use in the prevention, reduction and/or reversal of arterial aging in a subject having at least one cardiovascular disorder or having at least one risk factor for cardiovascular disorder.

In yet another aspect, the present invention is directed to a pharmaceutical composition comprising at least one renin-angiotensin-aldosterone system inhibitor in a subtherapeutic daily dose and at least one HMG-CoA reductase inhibitor in a subtherapeutic daily dose for use in decreasing worsening or occurrence of cardiovascular disorders in a subject having at least one cardiovascular disorder or having at least one risk factor for cardiovascular disorder.

In yet another aspect, the present invention relates to a pharmaceutical composition comprising at least one renin-angiotensin-aldosterone system inhibitor in a subtherapeutic daily dose and at least one HMG-CoA reductase inhibitor in a subtherapeutic daily dose wherein one intervention-cycle consists of one treatment-period lasting between about 1 month to about 9 months, preferably between about 1 month to about 9 months and one rest-period lasting 12 months, preferably between 1 and 12 months or between 1 and 6 months or between 1 and 3 months and wherein one intervention-cycle can be repeated unlimited times.

In yet another aspect, the present invention relates to a pharmaceutical composition comprising at least one renin-angiotensin-aldosterone system inhibitor in a subtherapeutic daily dose and at least one HMG-CoA reductase inhibitor in a subtherapeutic daily dose wherein the cardiovascular disorder or the risk for a cardiovascular disorder is selected from:

a) a cardiovascular disorder selected from the group consisting of ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In yet another aspect, the present invention relates to a pharmaceutical composition comprising at least one renin-angiotensin-aldosterone system inhibitor in a subtherapeutic daily dose and at least one HMG-CoA reductase inhibitor in a subtherapeutic daily dose, wherein the renin-angiotensin-aldosterone system inhibitor is an angiotensin II receptor antagonist, selected from the group consisting of, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, and wherein the HMG-CoA reductase inhibitor is selected from the group consisting of mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof.

In yet another aspect, the present invention relates to a pharmaceutical composition comprising valsartan or any pharmaceutically acceptable salts thereof in a daily dose between 1 and 40 mg and fluvastatin or any pharmaceutically acceptable salts thereof in a daily dose between 1 and 10 mg for use in maintaining or improving the functional and morphological properties of the arterial wall in a subject having at least one cardiovascular disorder or having at least one risk factor for cardiovascular disorder.

In yet another aspect, the present invention relates to a pharmaceutical composition comprising valsartan or any pharmaceutically acceptable salts thereof in a daily dose between 1 and 40 mg and fluvastatin or any pharmaceutically acceptable salts thereof in a daily dose between 1 and 10 mg for use in the prevention, reduction and/or reversal of arterial aging in a subject having at least one cardiovascular disorder or having at least one risk factor for a cardiovascular disorder.

In yet another aspect, the present invention relates to a pharmaceutical composition comprising valsartan or any pharmaceutically acceptable salts thereof in a daily dose between 1 and 40 mg and fluvastatin or any pharmaceutically acceptable salts thereof in a daily dose between 1 and 10 mg for use in decreasing worsening or occurrence of cardiovascular disorders in a subject having at least one cardiovascular disorder or having at least one risk factor for a cardiovascular disorder.

In a further aspect, the present invention relates to the pharmaceutical composition further comprising one or more pharmaceutically acceptable excipients.

As used herein, the morphological properties of the arterial wall are preferably to be understood as the stiffness properties of arteries. Preferably, arterial stiffness can be determined on the basis of the parameters pulse wave velocity (PWV) and β-stiffness.

Arterial stiffness is presently most adequately described by the parameter pulse wave velocity (PWV). The PWV is calculated from measurements of pulse transit time and the distance traveled by the pulse between two recording sites. Preferably, the PWV is measured on elastic arteries such as aorta, carotid artery, iliac artery, femoral artery. Thus, PWV represents the speed of pulse transmission through the arterial three. The stiffer the arteries are, the faster is the pulse transmission and consequently the higher is the PWV. The PWV can be easily and reproducibly measured using an ultrasound apparatus such as Aloka ProSound Alpha 10 apparatus with a high resolution eTracking system. Preferably the ultrasound apparatus is equipped with software for automatic determination of arterial stiffness parameters through the analysis of pulse waves. Other widely-used devices as Sphygmocor®, Compylor® and similar can be also used for PWV calculation.

The β-stiffness is also a parameter being a measure for arterial stiffness. It describes the local arterial stiffness. Accordingly, the determination of β-stiffness is a method for measuring stiffness from artery diameter and mutation width by the beating and blood pressure. Preferably β-stiffness is measured using a common carotid artery using an ultrasound apparatus such as Aloka ProSound Alpha 10 apparatus with a high resolution eTracking system. Preferably the ultrasound apparatus is equipped with software for automatic determination of arterial stiffness parameters through the analysis of pulse waves.

As used herein, the functional properties of the arterial wall are preferably characterized by the endothelial function of the arterial wall.

Endothelial function can be assessed with a variety of methods. The most widely used method is the ultrasound measurement of flow mediated dilatation (FMD) of brachial artery after short-term ischemia induced by sphygmomanometer inflation. Consequently, reactive hyperemia, which is dependent on endothelial function, occurs and brachial artery dilates. The present difference between the diameter measured after hyperemia and the basal diameter is taken as FMD. Generally FMD is used invasively with high-resolution ultrasound machines/systems; the measurements could be performed manually or automatically (as in the case when Aloka ProSound Alpha 10 apparatus is used).

The functional and morphological properties of the arterial wall are mandatory for allowing appropriate function of the arteries. In this regard, the term "appropriate function of arteries" refers to the accommodation of arterial wall to a wide range of physiological conditions to which the arteries might be exposed during short and long term fluctuations of burden.

As used herein the term "arterial aging" refers to changes, in particular gradual changes of morphological (i.e. structural) and functional properties of the arterial wall. Preferably, "arterial aging" exclusively refers to changes, in particular gradual changes of the morphological properties of the arterial wall.

As used herein, "arterial aging" is preferably based on the structural change of the arteries with aging caused e.g. by longstanding arterial pulsation in the central artery, which has a direct effect on the structural matrix proteins, collagen and elastin in the arterial wall, disrupting muscular attachments and causing elastin fibers to fatigue and fracture. Further, accumulation of advanced glycation endproducts (AGE) on the proteins alters their physical properties and causes stiffness of the fibers. Still further, the calcium content in the arterial wall increases with age, which also contributes to arterial aging (H.-Y. Lee et al., Circulation Journal 2010; 94; 2258-2262).

In connection with the subjects of the invention, i.e. unhealthy subjects, subjects having at least one cardiovascular disorder and/or subjects having at least one risk factor for cardiovascular disorder, the expressions "impairment of functional and morphological properties of the arterial wall" and "arterial aging" are preferably to be interpreted in that these changes may be caused or accelerated by the state of health of the subject, in particular if the subject has at least one risk for coronary heart disease, has at least one cardiovascular disorder and/or has at least one risk factor for a cardiovascular disorder.

Preferably, "unhealthy subjects" have a risk for a coronary heart disease (10-year risk) according to the Framingham Risk Score of more than 10%, preferably more than 12%, more preferably more than 15%, most preferably more than 20%. In particular, "unhealthy subjects" may be classified as "unhealthy subjects with a moderate Framingham risk score" of from more than 10 to 20%, and "unhealthy subjects with a high Framingham risk score" of more than 20%. The Framingham Risk Score for the CHD is calculated on the basis described in "The Third Report of the National Cholesterol Education Program (NCEP) Expert Panel on Detection, Evaluation and Treatment of High Blood Cholesterol in Adults (Adult Treatment Panel III)", Circulation 2002; 106: 3143-3421. The calculation of the Framingham Risk Score for a coronary heart disease (CHD) (10-year risk) is based on the ATP III page of the NHLBI Web site (www.nhlbi.nih.gov/guidelines/cholesterol) referenced at page 3229 of said article. The algorithm underlying the calculation of the Framingham risk equation in these calculators has been described by Anderson K M et al. in "An updated coronary risk profile. A statement for health professionals", Circulation (1991), 83:356-362.

With the Framingham risk score for the CHD (10 years) the risk for coronary heart diseases such as myocardial infarction and death is assessed. The parameters included in the Framingham risk score for the CHD are as follows: gender, age, total cholesterol level, HDL cholesterol level, smoking, systolic blood pressure and untreated/treated hypertension.

The term "unhealthy subject" may also cover "subjects having at least one cardiovascular disorder" and "subjects having at least one risk factor for a cardiovascular disorder".

As used herein "subjects having at least one cardiovascular disorder" are preferably subjects having a manifested cardiovascular disorder. The term "cardiovascular disorder" (CVD) according to the present invention refers to a cardiovascular disorder or cardiovascular event such as for example ischemic heart disease, carotid and intracerebral artery disease, peripheral arterial disease, aortic aneurism and the like, and any combinations thereof. Preferably CVD refers to myocardial infarction, stroke, dementia, critical limb ischemia, aortic aneurism and any combinations thereof, more preferably to myocardial infarction, stroke, vascular dementia and any combinations thereof, most preferably post-myocardial infarction.

As used herein "subjects having a risk factor for a cardiovascular disorder" have e.g. a disorder or a risky life style, which may cause a cardiovascular disorder. Disorders, which represent a risk factor for a cardiovascular disorder, are e.g. diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof. A risky life style, which represents a risk factor for a cardiovascular disorder, is preferably smoking, obesity, physical inactivity, continuous stress, and any combinations thereof.

As used herein, the term "subtherapeutic daily dose" in the context of the at least one HMG-CoA reductase inhibitor relates to a dose, which does not substantially change the cholesterol level. In this regard, the term "substantially" means that no therapeutic effect for the primary indication can be observed regarding these cholesterol levels. In a preferred embodiment, the LDL cholesterol level is not changed by more than 15%, preferably not more than 10%, more preferably not more than 8%. Preferably, the LDL cholesterol level is not decreased by more than 15%, preferably not more than 10%, more preferably not more than 8%. In another preferred embodiment, the HDL cholesterol level is not changed by more than 15%, preferably not more than 12%, more preferably not more than 10%. Preferably, the HDL cholesterol level is not decreased by more than 15%, preferably not more than 12%, more preferably not more than 10%.

The recommended daily therapeutic dose for a HMG-CoA reductase inhibitor is typically in the range of 10 mg to 80 mg. For example for the active Fluvastatin the recommended therapeutic daily dose is in the range of 40 mg to 80 mg. For atorvastatin the recommended therapeutic daily dose is in the range of 10 mg to 40 mg.

As used herein, the term "subtherapeutic daily dose" in the context of the at least one renin-angiotensin-aldosterone system inhibitor relates to a dose, which does not substantially change the blood pressure. Preferably, the systolic blood pressure is not changed by more than 15%, preferably not more than 10%. In another preferred embodiment, the diastolic blood pressure is not changed by more than 15%, preferably not more than 10%.

The recommended daily therapeutic dose for an angiotension II receptor antagonist is usually in the range of 20 mg to 320 mg. For example for the active Valsartan the recommended therapeutic daily dose is in the range of 40 mg to 320 mg. For Losartan the recommended therapeutic daily dose is in the range of 25 mg to 100 mg. For Telmisartan the recommended therapeutic daily dose is in the range of 40 mg to 320 mg.

The term "pharmaceutically acceptable salts" includes any and all non-toxic salts of the disclosed compounds. Examples of pharmaceutically acceptable salts include inorganic and organic acid addition salts and basic salt. The pharmaceutically acceptable salts include, but are not limited to metal salts, such as sodium salt, potassium salt, cesium salt, and the like; alkaline earth metals, such as calcium salt, magnesium salt and the like, organic amine salts such as triethylamine salt, pyridine salt, picoline salt, ethanolamine salt, triethanolamine salt, dicyclohexylamine salt, N,N'-dibenzylethylenediamine salt and the like, inorganic acid salts, such as hydrochloride, hydrobromide, phosphate, sulphate and the like, organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like, and amino acid salts such as arginate, glutamate, and the like. Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

The term "daily dose" of the pharmaceutically active ingredient(s) corresponds to the total amount of said active/the actives that is/are administered to a subject per day. The daily dose can be administered in any suitable frequency such as in a once-a-day dosage or alternatively in a divided dosage, e.g. twice-a-day dosage or dosages which have to be administered 3 or 4 times a day.

The term "residual improvement" refers to a change in the improvement of a parameter as measured after a certain time period (e.g. a rest period) in relation to the improvement achieved after a treatment period. The residual improvement after said time period is given as a percentage of the initial improvement (measured e.g. after determination of the treatment). As an example, the FMD at beginning of the treatment was 2%. The FMD measured after a treatment period was 4% (improvement 100%) and the FMD measured after a rest period following the treatment period was 3%, leading to a residual improvement of 50%.

The term "substantially", if not defined otherwise in the context it is used, means that the value following the term may deviate ±10%, preferably ±5%.

The term "treatment period" as used herein is defined as the time period in which a subject is administered the daily doses of the pharmaceutical composition according to the present invention. The treatment period is preferably at least one week, more preferably at least 10 days, even more preferably at least two weeks, or more preferably at least one month.

The term "rest period" as used herein is defined as the time period in which a subject is not administered the pharmaceutical composition of the present invention.

"Anti-inflammatory" refers to the property of a substance or treatment that reduces inflammation. Anti-inflammatory substances should suppress the expression induction of inflammatory functional proteins such as enzyme participating in the production of chemical mediator of various cytokines and inflammation, as well as suppress information transfer in cells participating in activation, and/or suppress the action expression by chemical mediator of various cytokines and inflammation.

An "antioxidant" is known as a molecule that can neutralize free radicals by accepting or donating an electron to eliminate the unpaired condition. Typically this means that the antioxidant molecule becomes a free radical in the process of neutralizing a free radical molecule to a non-free-radical molecule. But the antioxidant molecule will usually be a much less reactive free radical than the free radical neutralized. Therefore, an antioxidant inhibits the oxidation of other molecules. Oxidation is a chemical reaction that transfers electrons from a substance to an oxidizing agent. Oxidation reactions can produce free radicals. In turn, these radicals can start chain reactions that damage cells. Antioxidants terminate oxidation chain reactions by removing free radical intermediates, and inhibit other oxidation reactions.

FIGURES

FIG. 1: Improvements in functional and morphological properties of arterial wall in patients with moderate CHD Framingham Risk score (10 year) (more than 10-20%): A) flow mediated dilation (FMD) and B) pulse wave velocity (PWV) and C) β-stiffness of carotid artery before and after 30 days of treatment with pharmaceutical composition according to present invention (Example 1)

Figure 2:
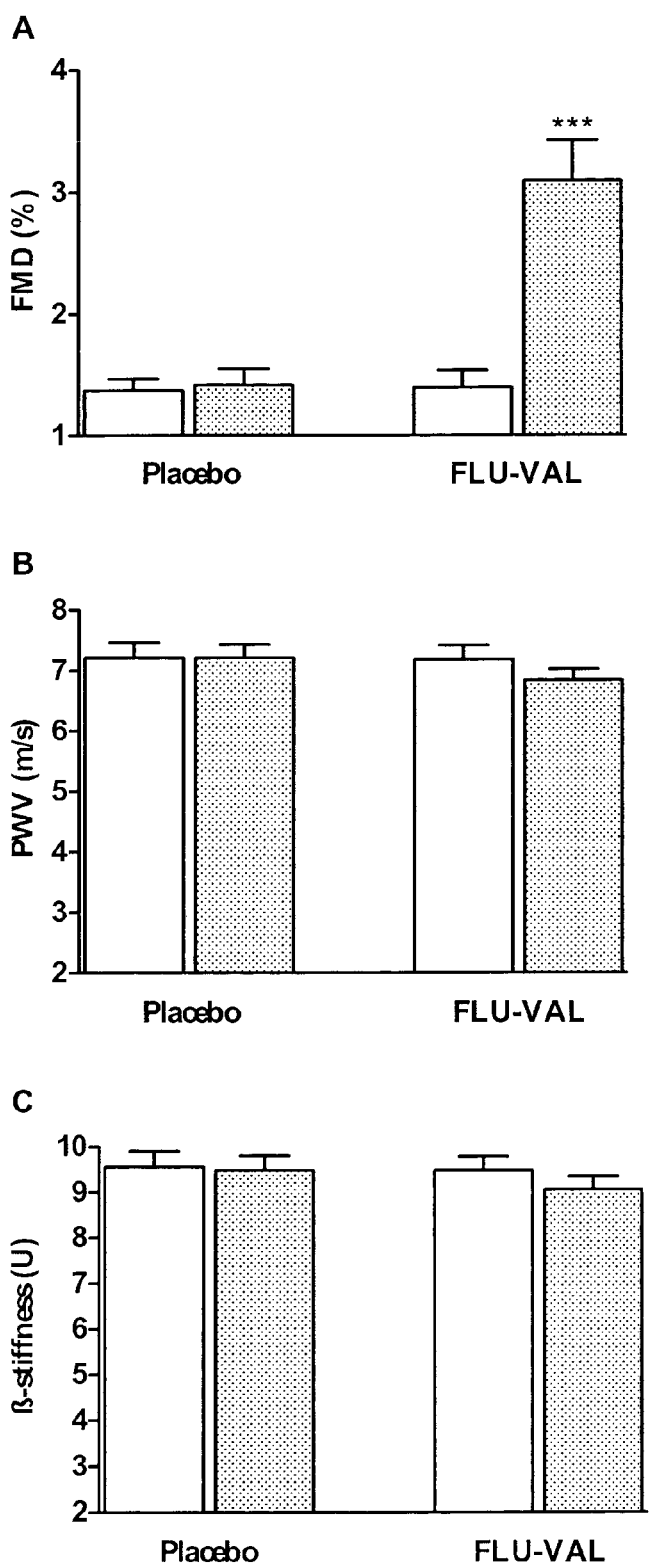

FIG. 2: Improvements in functional and morphological properties of arterial wall in patients with high Framingham Risk score (>20%): A) flow mediated dilation (FMD) and B) pulse wave velocity (PWV) and C) β-stiffness of carotid artery before and after 30 days of treatment with pharmaceutical composition according to present invention (Example 2)

Figure 3:
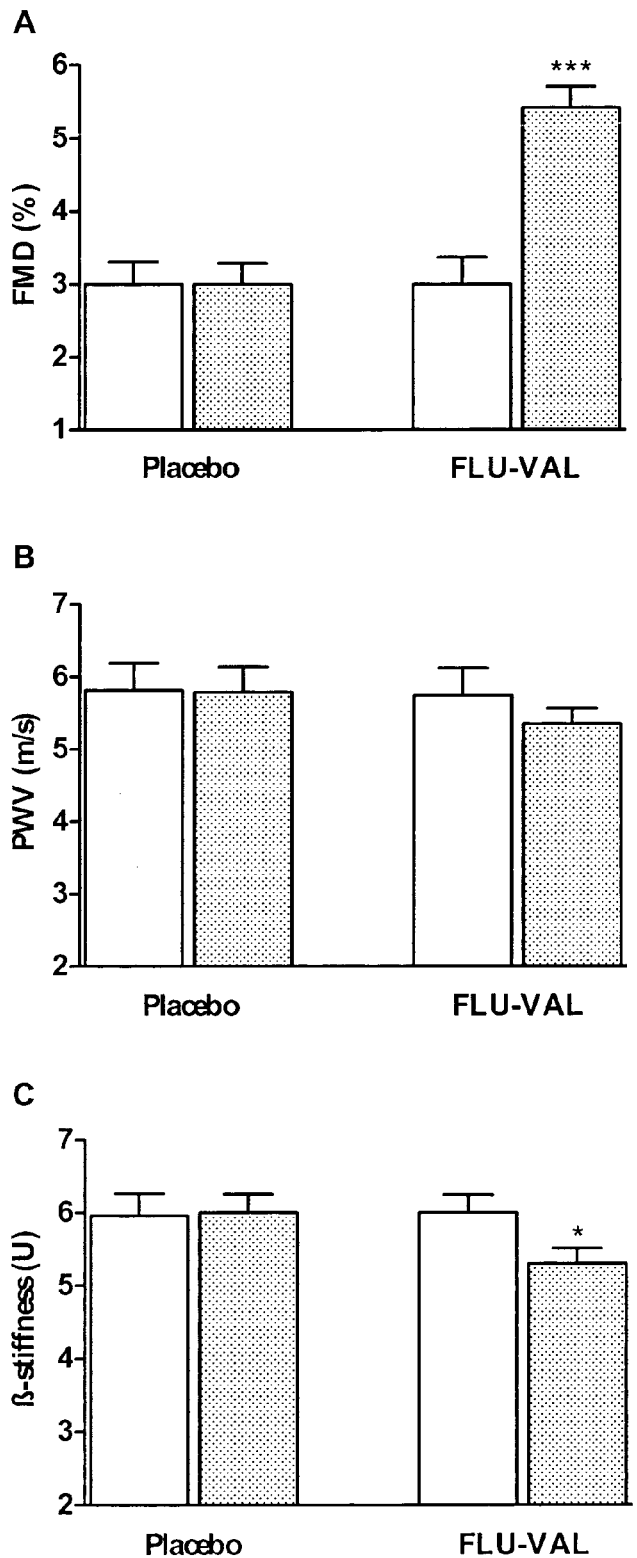

FIG. 3: Improvements in functional and morphological properties of arterial wall in patients with diabetes mellitus type 1: A) flow mediated dilation (FMD) and B) pulse wave velocity (PWV) and C) β-stiffness of carotid artery before and after 30 days of treatment with pharmaceutical composition according to present invention (Example 3, Study II)

Figure 4:
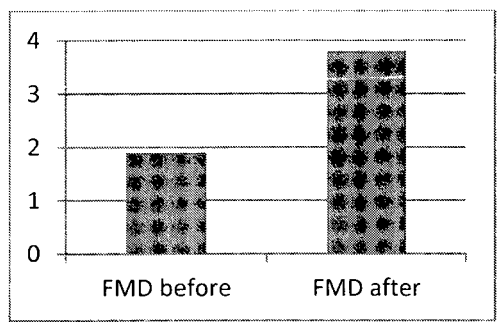
Figure 4:
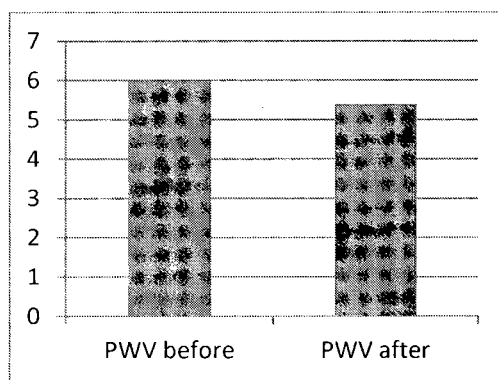
Figure 4:
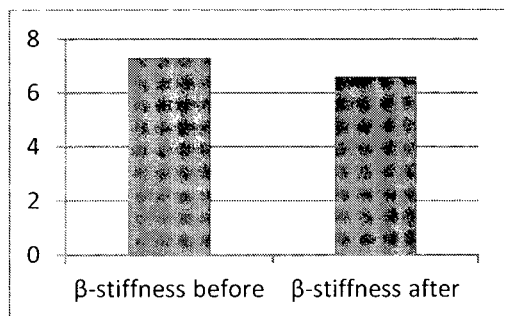

FIG. 4: Improvements in functional and morphological properties of arterial wall in patients with diabetes mellitus type 1: A) flow mediated dilation (FMD) and B) pulse wave velocity (PWV) and C) β-stiffness of carotid artery before and after 30 days of treatment with pharmaceutical composition according to present invention (Example 3, Study I)

Figure 5:
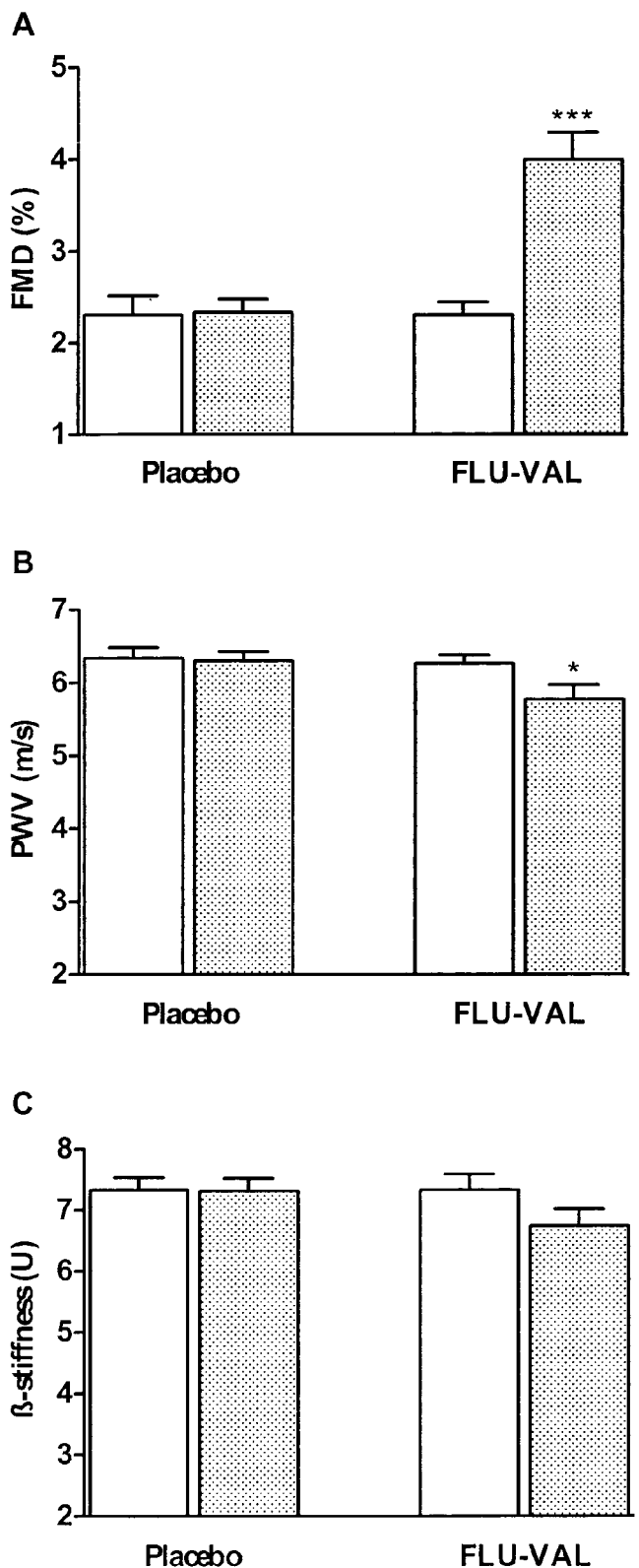

FIG. 5: Improvements in functional and morphological properties of arterial wall in patients with diabetes mellitus type 2: A) flow mediated dilation (FMD) and B) pulse wave velocity (PWV) and C) β-stiffness of carotid artery before and after 30 days of treatment with pharmaceutical composition according to present invention (Example 4, Study II)

Figure 6:
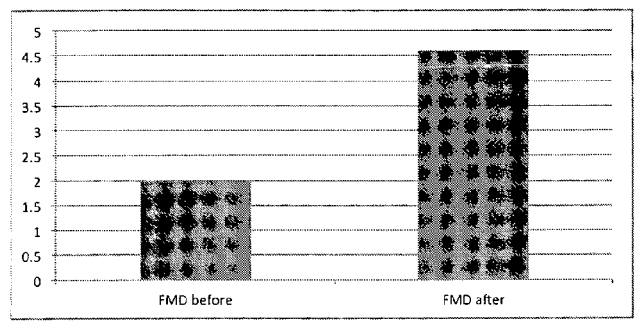
Figure 6:
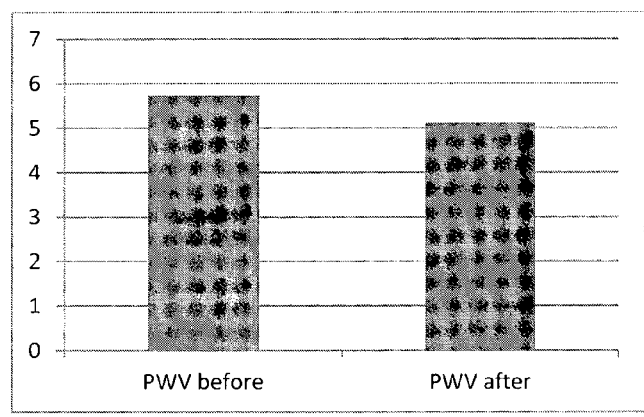
Figure 6:
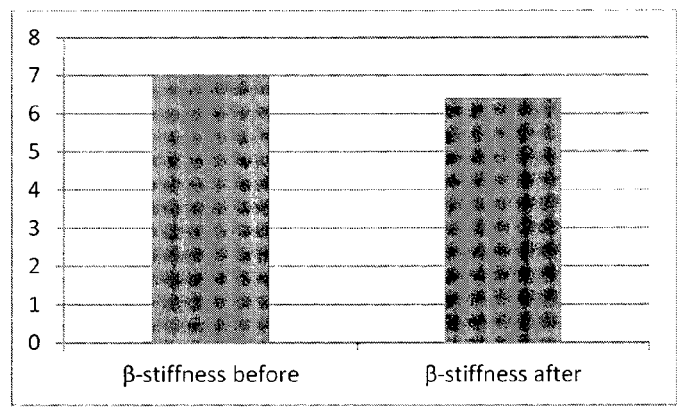

FIG. 6: Improvements in functional and morphological properties of arterial wall in patients with diabetes mellitus type 2: A) flow mediated dilation (FMD) and B) pulse wave velocity (PWV) and C) β-stiffness of carotid artery before and after 30 days of treatment with pharmaceutical composition according to present invention (Example 4, Study I)

Figure 7:
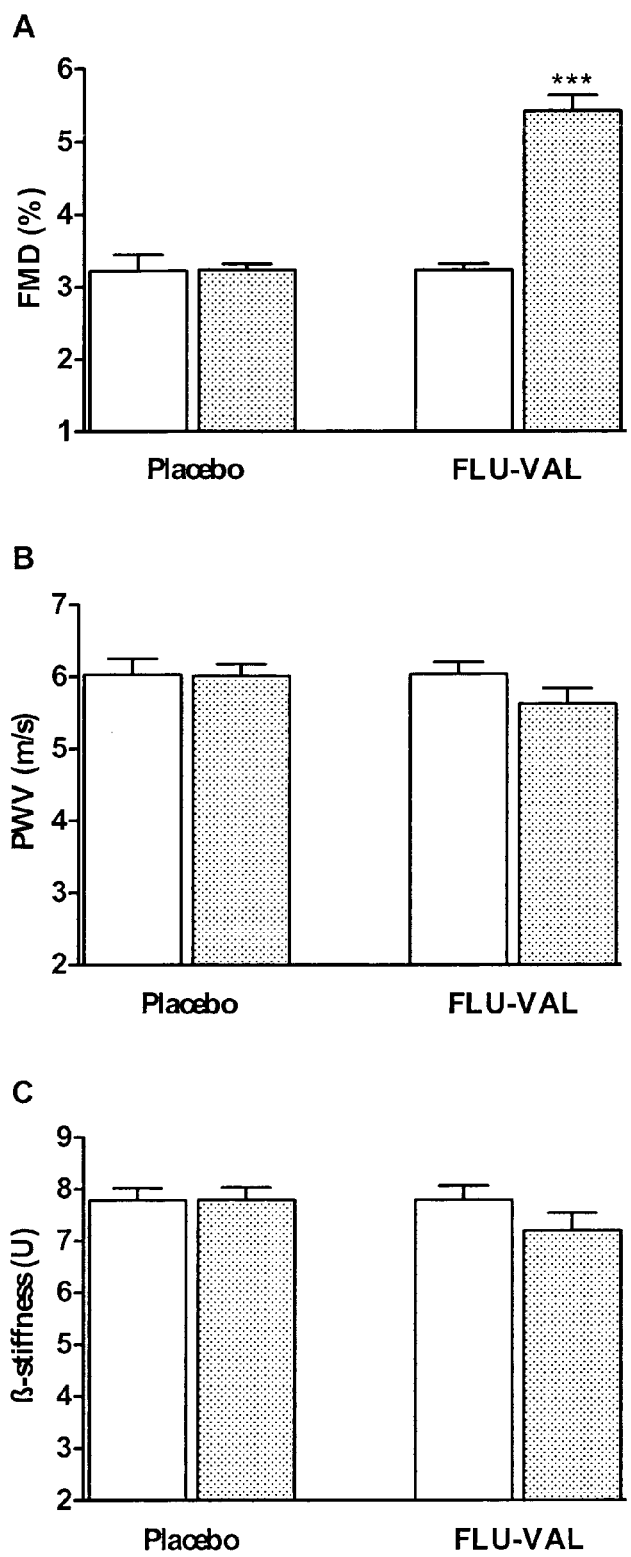

FIG. 7: Improvements in functional and morphological properties of arterial wall in post-myocardial infarction patients (patients with coronary artery disease): A) flow mediated dilation (FMD) and B) pulse wave velocity (PWV) and C) β-stiffness of carotid artery before and after 30 days of treatment with pharmaceutical composition according to present invention (Example 5, Study II)

Figure 8:
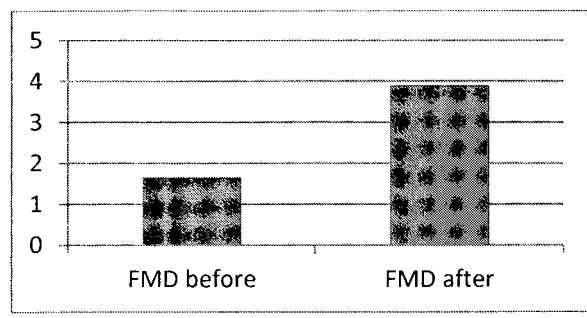
Figure 8:
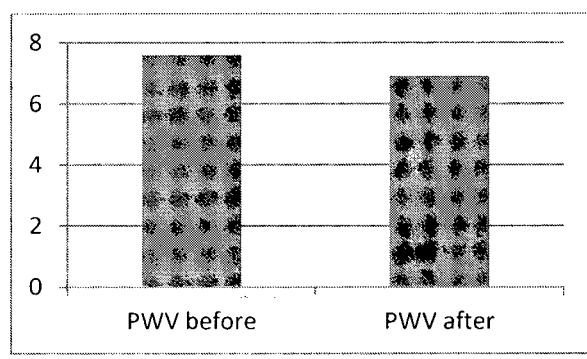
Figure 8:
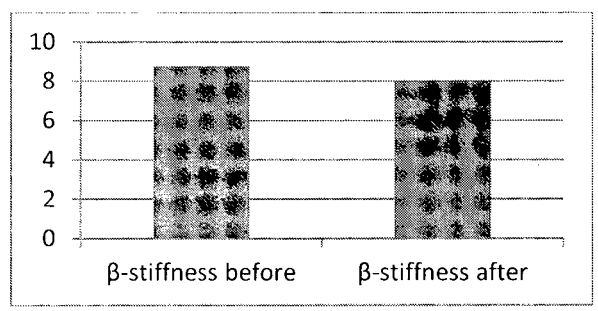

FIG. 8: Improvements in functional and morphological properties of arterial wall in patients with post-myocardial infarction: A) flow mediated dilation (FMD) and B) pulse wave velocity (PWV) and C) β-stiffness of carotid artery before and after 30 days of treatment with pharmaceutical composition according to present invention (Example 5, Study I)

Figure 9:
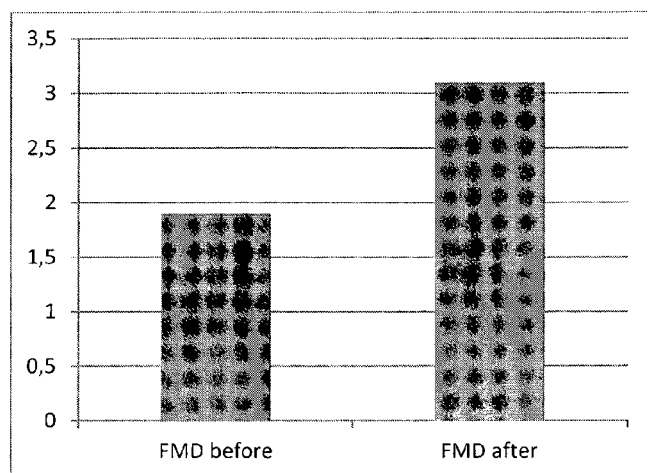
Figure 9:
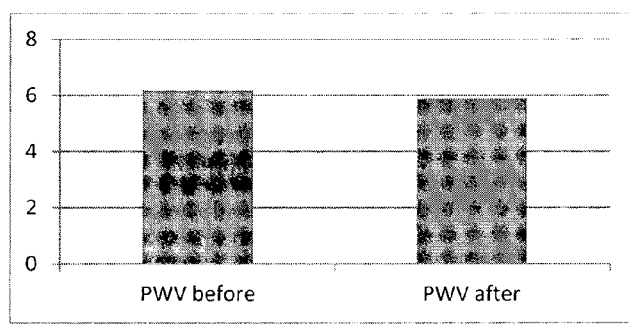
Figure 9:
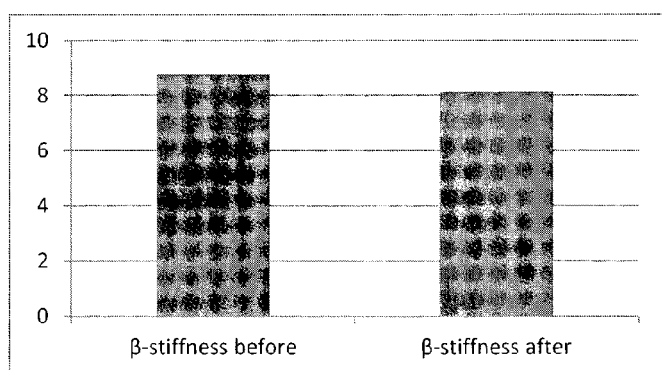

FIG. 9: Improvements in functional and morphological properties of arterial wall in patients with arterial hypertension: A) flow mediated dilation (FMD) and B) pulse wave velocity (PWV) and C) β-stiffness of carotid artery before and after 30 days of treatment with pharmaceutical composition according to present invention (Example 6, Study I)

Figure 10:
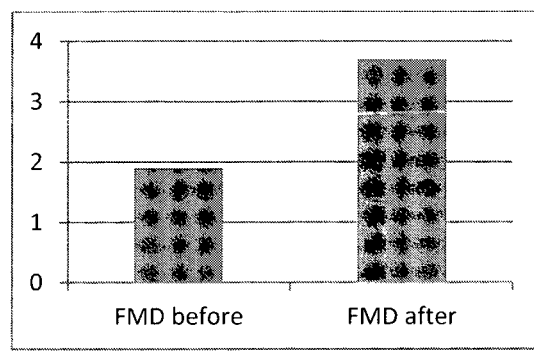
Figure 10:
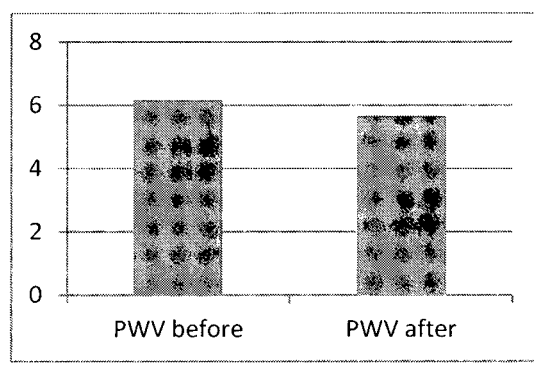
Figure 10:
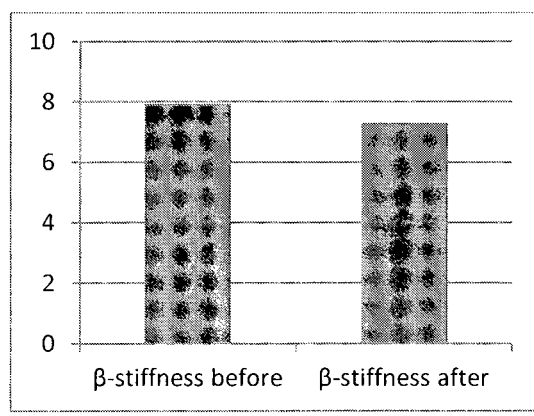

FIG. 10: Improvements in functional and morphological properties of arterial wall in patients with hypercholesterolemia: A) flow mediated dilation (FMD) and B) pulse wave velocity (PWV) and C) β-stiffness of carotid artery before and after 30 days of treatment with pharmaceutical composition according to present invention (Example 7, Study I)

Figure 11:
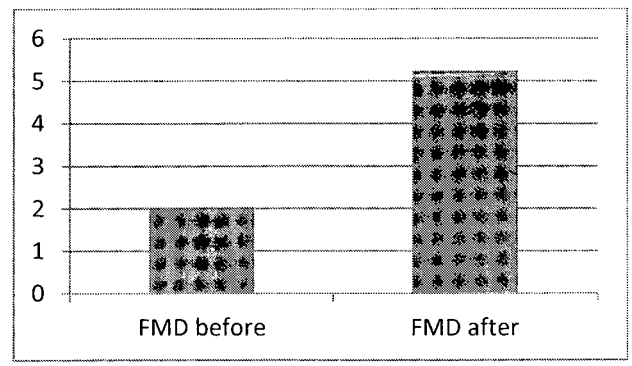
Figure 11:
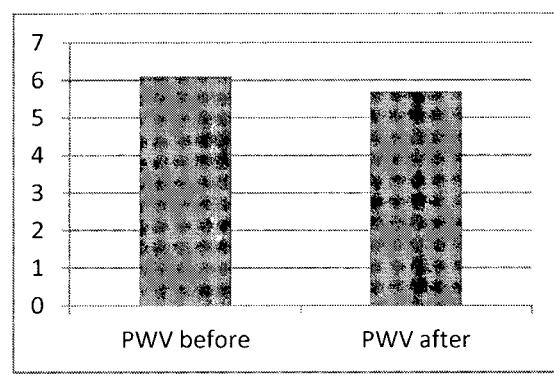
Figure 11:
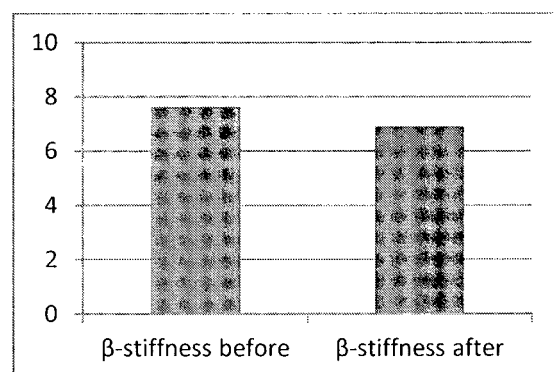

FIG. 11: Improvements in functional and morphological properties of arterial wall in participants with risk factor for cardiovascular disorder—smoking: A) flow mediated dilation (FMD) and B) pulse wave velocity (PWV) and C) β-stiffness of carotid artery before and after 30 days of treatment with pharmaceutical composition according to present invention (Example 8, Study I)

Figure 12:
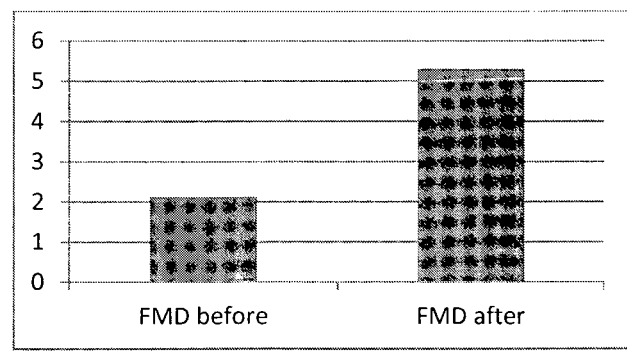
Figure 12:
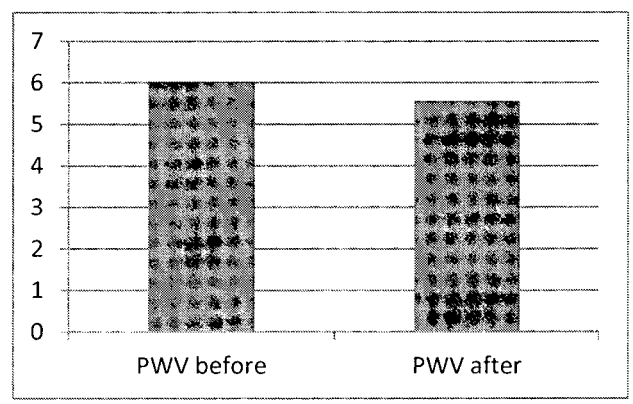
Figure 12:
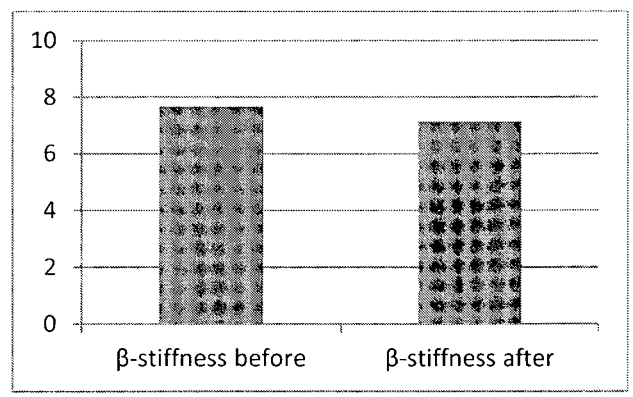

FIG. 12: Improvements in functional and morphological properties of arterial wall in participants with risk factor for cardiovascular disorder—obesity: A) flow mediated dilation (FMD) and B) pulse wave velocity (PWV) and C) β-stiffness of carotid artery before and after 30 days of treatment with pharmaceutical composition according to present invention (Example 9, Study I)

DETAILED DESCRIPTION OF INVENTION

In a first embodiment, the present invention is directed to pharmaceutical composition comprising at least one renin-angiotensin-aldosterone system inhibitor in a subtherapeutic daily dose, and at least one HMG-CoA reductase inhibitor in a subtherapeutic daily dose, for use in maintaining or improving the functional and morphological properties of the arterial wall in unhealthy subjects.

In a second embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in the prevention, reduction or reversal of arterial aging in unhealthy subjects.

In a third embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in decreasing the worsening or the occurrence of cardiovascular disorders in unhealthy subjects.

In a preferred embodiment of the first, second or third embodiment, the unhealthy subjects have a risk for a coronary heart disease (10-year risk) according to the Framingham Risk Score of more than 10%, preferably more than 12%, more preferably more than 15%, most preferably more than 20%.

In a fourth embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in maintaining or improving the functional and morphological properties of the arterial wall in subjects having at least one cardiovascular disorder.

In a fifth embodiment, the present invention is directed to pharmaceutical composition comprising at least one renin-angiotensin-aldosterone system inhibitor in a subtherapeutic daily dose, and at least one HMG-CoA reductase inhibitor in a subtherapeutic daily dose, for use in the prevention, reduction or reversal of arterial aging in subjects having at least one cardiovascular disorder.

In a sixth embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in decreasing the worsening or the occurrence of cardiovascular disorders in subjects having at least one cardiovascular disorder.

In a preferred embodiment of the fourth, fifth or sixth embodiment, the cardiovascular disorder is selected from the group consisting of ischemic heart disease, carotid and intracerebral artery disease, peripheral arterial disease, aortic aneurism, and any combinations thereof.

In another preferred embodiment of the fourth, fifth or sixth embodiment, the cardiovascular disorder is selected from the group consisting of myocardial infarction, stroke, dementia, critical limb ischemia, aortic aneurism, and any combinations thereof, preferably myocardial infarction, stroke, vascular dementia, and any combinations thereof, more preferably post-myocardial infarction.

In a seventh embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in maintaining or improving the functional and morphological properties of the arterial wall in subjects having at least one risk factor for a cardiovascular disorder.

In an eighth embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in the prevention, reduction or reversal of arterial aging in subjects having at least one risk factor for a cardiovascular disorder.

In a ninth embodiment, the present invention is directed to a pharmaceutical composition comprising at least one renin-angiotensin-aldosterone system inhibitor in a subtherapeutic daily dose, and at least one HMG-CoA reductase inhibitor in a subtherapeutic daily dose, for use in decreasing the worsening or the occurrence of cardiovascular disorders in subjects having at least one risk factor for a cardiovascular disorder.

In a preferred embodiment of the seventh, eighth or ninth embodiment, the risk factor for a cardiovascular disorder is a disorder selected form the group consisting of diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably, diabetes, metabolic syndrome, arterial hypertension, hypercholesterolemia, and any combinations thereof, still more preferably diabetes mellitus type 1, diabetes mellitus type 2, arterial hypertension or hypercholesterolemia, and any combinations thereof, most preferably diabetes mellitus type 1 or diabetes mellitus type 2.

In another preferred embodiment of the seventh, eighth or ninth embodiment, the risk factor for a cardiovascular disorder is a risky life style selected from the group consisting of smoking, obesity, physical inactivity, continuous stress, and any combinations thereof, preferably smoking, obesity, physical inactivity, continuous stress, and any combinations thereof, more preferably smoking, obesity, and any combinations thereof, most preferably smoking or obesity.

In one further embodiment, the present invention is directed to a pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having at least one cardiovascular disorder and/or having at least one risk factor for cardiovascular disorder.

According to the present invention, the term subtherapeutic daily dose relates to the dose that does not change cholesterol level and blood pressure, therefore the beneficial effects at this dose are attributed solely/purely to the pleotropic effects of angiotensin II receptor antagonist and HMG-CoA reductase inhibitor. Preferably, subtherapeutic daily dose is between 1 and 50%, more preferably between 1 and 25% of daily recommended therapeutic dose for particular active substance. Subtherapeutic daily dose does not produce side-effects which is an important limitation of therapeutic dosages particularly for long term usage during which known and still unknown complications or side-effects could occur. It is well known that side-effects are related to the dose of the used drug being more frequent at higher dosages.

Therefore, in a preferred embodiment, the present invention relates to a pharmaceutical composition comprising at least one renin-angiotensin-aldosterone system inhibitor in a daily dose between 1 and 50%, preferably between 1 and 25% of daily recommended therapeutic dose and at least one HMG-CoA reductase inhibitor in a daily dose between 1 and 50%, preferably between 1 and 25% of daily recommended therapeutic dose for use in maintaining or improving the functional and morphological properties of the arterial wall in a subject having at least one cardiovascular disorder or having at least one risk factor for cardiovascular disorder.

Preferably, the cardiovascular disorder (CVD) selected from the group consisting of ischemic heart disease, carotid and intracerebral artery disease, peripheral arterial disease, aortic aneurism and similar, and any combinations thereof. More preferably, the CVD is selected form the group consisting of myocardial infarction, stroke, dementia, critical limb ischemia, aortic aneurism and any combinations thereof, more preferably to myocardial infarction, stroke, vascular dementia and any combinations thereof.

Preferably, the risk factor for a CVD is a disorder which causes a high risk for CVD occurrence as for example diabetes, metabolic syndrome, hypercholesterolemia, hypertension, chronic inflammatory disorder such as for example rheumatoid arthritis, psoriasis, and similar, and any combinations thereof, or a risky life style which causes a high risk for CVD occurrence as for example smoking, obesity, physical inactivity, continuous stress, and similar, and any combinations thereof. More preferably, the risk factor for CVD is selected from the group consisting of diabetes, metabolic syndrome, hypercholesterolemia, hypertension, smoking, obesity, physical inactivity, continuous stress, and any combinations thereof, most preferably from diabetes, metabolic syndrome, arterial hypertension, hypercholesterolemia, smoking, obesity and any combinations thereof.

In another preferred embodiment, the present invention is therefore directed to a pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having
  a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or
  b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a more preferred embodiment, the present invention is directed to a pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having a) a cardiovascular disorder selected from the group consisting of, but not limited to, myocardial infarction, stroke, vascular dementia, and any combinations thereof, or b) a disorder which causes a high risk for cardiovascular disorder occurrence selected from the group consisting of but not limited to, diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, and any combinations thereof.

In a still more preferred embodiment, the pharmaceutical composition comprises at least one renin-angiotensin-aldosterone system inhibitor in a daily dose that is between 1 and 50%, preferably between 1 and 25% of daily recommended therapeutic dose and at least one HMG-CoA reductase inhibitor in a daily dose that is between 1 and 50%, preferably between 1 and 25% of daily recommended therapeutic dose, and is suitable for use in maintaining or improving the functional and morphological properties of the arterial wall in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a yet more preferred embodiment, the pharmaceutical composition comprises at least one renin-angiotensin-aldosterone system inhibitor in a daily dose that is between 1 and 50%, preferably between 1 and 25% of daily recommended therapeutic dose and at least one HMG-CoA reductase inhibitor in a daily dose that is between 1 and 50%, preferably between 1 and 25% of daily recommended therapeutic dose, and is suitable for use in maintaining or improving the functional and morphological properties of the arterial wall in a subject having a) a cardiovascular disorder selected from the group consisting of, but not limited to, myocardial infarction, stroke, vascular dementia and any combinations thereof or b) a disorder which causes a high risk for cardiovascular disorder occurrence selected from the group consisting of but not limited to, diabetes, metabolic syndrome, arterial hypertension, hypercholesterolemia, and any combinations thereof, or c) a risky life style which causes a high risk for cardiovascular occurrence selected from the group consisting of, but not limited to, smoking, obesity, and any combinations thereof.

The term renin-angiotensin-aldosterone system (RAAS) inhibitor as used in the present invention can include renin inhibitor, angiotensin-converting enzyme (ACE) inhibitor and angiotensin II receptor antagonist and any combinations thereof.

The renin inhibitor can e.g. be aliskiren.

The term ACE inhibitor as used in the present invention can include, but is not limited to, benazepril, captopril, enalapril, fosinopril, lisinopril, perindopril, trandolapril, moexipril, quinapril, ramipril and any pharmaceutically acceptable salts or esters thereof. Preferably ACE inhibitor can be selected from the group consisting of, but not limited to, perindopril, lisinopril, enalapril, moexipril, ramipril and any pharmaceutically acceptable salts or esters thereof, more preferably it can be selected from the group consisting of, but not limited to, perindopril and ramipril and any pharmaceutically acceptable salts or esters thereof.

The term angiotensin II receptor antagonist as used in the present invention can include, but is not limited to, azilsartan, losartan, eprosartan, irbesartan, olmesartan, candesartan, valsartan and telmisartan and any pharmaceutically acceptable salts or esters thereof. Preferably angiotensin II receptor antagonist can be selected from the group consisting of, but not limited to, azilsartan, losartan, telmisartan, olmesartan, candesartan and valsartan and any pharmaceutically acceptable salts or esters thereof, more preferably it can be selected from the group consisting of, but not limited to, losartan, telmisartan, azilsartan, candesartan and valsartan and any pharmaceutically acceptable salts or esters thereof and even more preferably angiotensin II receptor antagonist is valsartan and telmisartan and any pharmaceutically acceptable salts or esters thereof.

Moreover, the term RAAS inhibitor as used in the present invention can further include one or more combinations with other active substance such as for example, but not limited to, combination with diuretic, such as for example thiazide such as for example chlorothiazide, chlorthalidone, hydrochlorothiazide, hydroflumethiazide, indapamide, methyclothiazide, metolazone, polythiazide, preferably hydrochlorothiazide and indapamide; loop diuretic such as for example bumetanide, ethacrynic acid, furosemide, torsemide, preferably furosemide and torsemide; K+-sparing diuretic such as for example amioloride, eplerenone, spironolactone, triamterene, preferably eplerenone and spironolactone; and Ca-inhibitors such as for example acetazolamide, dichlorphenamide, methazolamide; more preferably hydrochlorothiazide; combination with calcium channel blockers such as for example dihydropiridine calcium channel blockers that can be selected from the group consisting of, but not limited to, amlodipine, aranidipine, azelnidipine, barnidipine, benidipine, felodipine, lacidipine, lercanidipine, manidipine, nicardipine, nifedipine, nilvadipine, nimodipine, nisoldipine, nitrendipine, pranidipine, preferably amlodipine, and any pharmaceutically acceptable salts or esters thereof and any combinations thereof.

In a preferred embodiment of the present invention, the at least one renin-angiotensin-aldosterone inhibitor in the pharmaceutical composition of the present invention is selected from the group consisting of renin inhibitor, angiotensin converting enzyme inhibitor, angiotensin II receptor antagonist and combinations thereof. Preferably, the renin-angiotensin-aldosterone system inhibitor is an angiotensin II receptor antagonist.

In a more preferred embodiment, the angiotensin II receptor antagonist is selected from the group consisting of azilsartan, losartan, eprosartan, irbesartan, olmesartan, candesartan, valsartan, telmisartan, and any pharmaceutically acceptable salts or esters and any combinations thereof. Preferably, the angiotensin II receptor antagonist is selected from the group consisting of azilsartan, losartan, olmesartan, candesartan, valsartan, telmisartan, and any pharmaceutically acceptable salts or esters, and combinations thereof. More preferably, the angiotensin II receptor antagonist is selected from the group consisting of azilsartan, losartan, candesartan, valsartan, telmisartan, and any pharmaceutically acceptable salts or esters, and combinations thereof. Still more preferably, the angiotensin II receptor antagonist is selected from the group consisting of losartan, valsartan, telmisartan, olmesartan, irbesartan and any pharmaceutically acceptable salts or esters, and combinations thereof. Most preferably, the angiotensin II receptor antagonist is selected from the group consisting of, valsartan, telmisartan, olmesartan, irbesartan and any pharmaceutically acceptable salts or esters, and combinations thereof.

In one particularly preferred embodiment, the angiotensin II receptor antagonist in the pharmaceutical composition of the invention is valsartan or any pharmaceutically acceptable salt thereof, preferably valsartan.

In another particularly preferred embodiment, the angiotensin II receptor antagonist in the pharmaceutical composition of the invention is telmisartan or any pharmaceutically acceptable salt thereof.

In another particularly preferred embodiment, the angiotensin II receptor antagonist in the pharmaceutical composition of the invention is olmesartan or any pharmaceutically acceptable salt thereof, preferably olmesartan medoxomil.

In another particularly preferred embodiment, the angiotensin II receptor antagonist in the pharmaceutical composition of the invention is irbesartan or any pharmaceutically acceptable salt thereof.

The term HMG-CoA reductase inhibitor as used in the present invention can include, but is not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin, rosuvastatin and atorvastatin and any pharmaceutically acceptable salts or esters thereof.

Moreover, the term HMG-CoA reductase inhibitor as used in the present invention can further include one or more combination with other active substance such as for example, but not limited to, combination with cholesterol absorption inhibitor such as ezetimibe, combination with calcium channel blockers, such as for example dihydropiridine calcium channel blockers that can be selected from the group consisting of, but not limited to, amlodipine, aranidipine, azelnidipine, barnidipine, benidipine, felodipine, lacidipine, lercanidipine, manidipine, nicardipine, nifedipine, nilvadipine, nimodipine, nisoldipine, nitrendipine, pranidipine, preferably amlodipine, and any pharmaceutically acceptable salts or esters thereof and any combinations thereof.

In a preferred embodiment of the present invention, the at least one HMG-CoA reductase inhibitor in the pharmaceutical composition of the present invention is selected from the group consisting of mevastatin, pitavastatin, lovastatin, simvastatin, pravastatin, fluvastatin, atorvastatin, cerivastatin, rosuvastatin, and any pharmaceutically acceptable salts or esters, and combinations thereof. Preferably, the HMG-CoA reductase inhibitor is selected from the group consisting of simvastatin, fluvastatin, atorvastatin, rosuvastatin, and any pharmaceutically acceptable salts or esters, and combinations thereof. More preferably, the HMG-CoA reductase inhibitor is selected from the group consisting of fluvastatin, atorvastatin, rosuvastatin, and any pharmaceutically acceptable salts or esters, and combinations thereof.

In one particularly preferred embodiment, the HMG-CoA reductase inhibitor in the pharmaceutical composition of the present invention is fluvastatin or any pharmaceutically acceptable salt thereof, and preferably is fluvastatin sodium.

In another particularly preferred embodiment, the HMG-CoA reductase inhibitor in the pharmaceutical composition of the present invention is atorvastatin or any pharmaceutically acceptable salt thereof, and preferably is atorvastatin calcium.

In another particularly preferred embodiment, the HMG-CoA reductase inhibitor in the pharmaceutical composition of the present invention is rosuvastatin or any pharmaceutically acceptable salt thereof, and preferably is rosuvastatin calcium.

In a preferred embodiment, the pharmaceutical compositions of the present invention are characterized in that the renin-angiotensin-aldosterone system inhibitor is an angiotensin II receptor antagonist selected from the group consisting of valsartan, telmisartan, olmesartan, irbesartan and any pharmaceutically acceptable salts or esters thereof, and the HMG-CoA reductase inhibitor is selected from the group consisting of fluvastatin, rosuvastatin and atorvastatin and any pharmaceutically acceptable salts or esters thereof. Preferably, the angiotensin II receptor antagonist and the HMG-CoA reductase inhibitor are present in the pharmaceutical composition of the invention in a weight ratio of from 20:1 to 1:20, preferably in a weight ratio of from 10:1 to 1:10, more preferably in a weight ratio of from 5:1 to 1:5.

In another preferred embodiment, the renin-angiotensin-aldosterone system inhibitor is valsartan or a pharmaceutically acceptable salt or ester thereof and the HMG-CoA reductase inhibitor is fluvastatin or a pharmaceutically acceptable salt or ester thereof.

In a particularly preferred embodiment, the renin-angiotensin-aldosterone system inhibitor is valsartan and the HMG-CoA reductase inhibitor is fluvastatin sodium. Preferably, valsartan and fluvastatin sodium are present in the composition in a weight ratio of from 9:1 to 1:9, preferably in a weight ratio of from 5:1 to 1:1, more preferably in a weight ratio of from 3:1 to 1:1, still more preferably in a weight ratio of from 2.5:1 to 1.6:1, most preferably in a weight ratio of 2:1. In another more preferred embodiment, valsartan and fluvastatin sodium are present in the composition in a weight ratio of from 9:1 to 1:9, preferably in a weight ratio of from 1:1 to 1:5, more preferably in a weight ratio of from 1:1 to 1:3, still more preferably in a weight ratio of from 1:1.6 to 1:2.5, most preferably in a weight ratio of 1:2.

In another preferred embodiment, the renin-angiotensin-aldosterone system inhibitor is valsartan or a pharmaceutically acceptable salt or ester thereof and the HMG-CoA reductase inhibitor is atorvastatin or a pharmaceutically acceptable salt or ester thereof.

In a particularly preferred embodiment, the renin-angiotensin-aldosterone system inhibitor is valsartan and the HMG-CoA reductase inhibitor is atorvastatin calcium. Preferably, valsartan and atorvastatin calcium are present in the composition in a weight ratio of from 9:1 to 1:9, preferably in a weight ratio of from 5:1 to 1:1, more preferably in a weight ratio of from 3.5:1 to 1.5:1, still more preferably in a weight ratio of from 3:1 to 2:1, most preferably in a weight ratio of 2.5:1. In another more preferred embodiment, valsartan and atorvastatin calcium are present in the composition in a weight ratio of from 20:1 to 1:1, preferably in a weight ratio of from 12:1 to 5:1, more preferably in a weight ratio of from 10:1 to 6:1, still more preferably in a weight ratio of from 9:1 to 7:1, most preferably in a weight ratio of 8:1.

In a preferred embodiment, the subtherapeutic daily dose of the HMG-CoA reductase inhibitor does not substantially change the cholesterol level.

In a more preferred embodiment, the subtherapeutic daily dose of the HMG-CoA reductase inhibitor does not change the LDL cholesterol level in a subject by more than 15%, preferably more than 10%, more preferably more than 8%. Still more preferably, the subtherapeutic daily dose of the HMG-CoA reductase inhibitor does not change the LDL cholesterol level in a subject by more than 15%, preferably more than 10%, more preferably more than 8%, when administered for at least 10 days, preferably at least 14 days, more preferably at least 1 month.

In another more preferred embodiment, the subtherapeutic daily dose of the HMG-CoA reductase inhibitor does not change the HDL cholesterol level in a subject by more than 15%, preferably more than 12%, more preferably more than 10%. Still more preferably, the subtherapeutic daily dose of the HMG-CoA reductase inhibitor does not change the HDL cholesterol level in a subject by more than 15%, preferably more than 12%, more preferably 10%, when administered for at least 10 days, preferably at least 14 days, more preferably at least 1 month.

In a preferred embodiment, the subtherapeutic daily dose of the renin-angiotensin-aldosterone system inhibitor does not substantially change the systolic blood pressure. In another preferred embodiment, the subtherapeutic daily dose of the renin-angiotensin-aldosterone system inhibitor does not substantially change the diastolic blood pressure.

In a more preferred embodiment, the subtherapeutic daily dose of the renin-angiotensin-aldosterone system inhibitor does not change the systolic blood pressure in a subject by more than 10%, preferably more than 8%, more preferably more than 6%, most preferably more than 4%. Still more preferably, the subtherapeutic daily dose of the renin-angiotensin-aldosterone system inhibitor does not change the systolic blood pressure in a subject by more than 10%, preferably more than 8%, more preferably more than 6%, most preferably more than 4%, when administered for at least 10 days, preferably at least 14 days, more preferably at least 1 month.

In another more preferred embodiment, the subtherapeutic daily dose of the renin-angiotensin-aldosterone system inhibitor does not change the diastolic blood pressure in a subject by more than 10%, preferably more than 8%, more preferably more than 6%, most preferably more than 5%. Still more preferably, the subtherapeutic daily dose of the renin-angiotensin-aldosterone system inhibitor does not change the diastolic blood pressure in a subject by more than 10%, preferably more than 8%, more preferably more than 6%, most preferably more than 5%, when administered for at least 10 days, preferably at least 14 days, more preferably at least 1 month.

In a preferred embodiment, the subtherapeutic daily dose of the renin-angiotensin-aldosterone system inhibitor and the subtherapeutic daily dose of the HMG-CoA reductase inhibitor together do not change the LDL cholesterol level by more than 15%, preferably more than 10%, more preferably more than 8%. Preferably, the subtherapeutic daily dose of the renin-angiotensin-aldosterone system inhibitor and the subtherapeutic daily dose of the HMG-CoA reductase inhibitor together do not change the LDL cholesterol level by more than 15%, preferably more than 10%, more preferably more than 8%, when administered for at least 10 days, preferably at least 14 days, more preferably at least 1 month.

In another preferred embodiment, the subtherapeutic daily dose of the renin-angiotensin-aldosterone system inhibitor and the subtherapeutic daily dose of the HMG-CoA reductase inhibitor together do not change the HDL cholesterol level by more than 15%, preferably more than 12%, more preferably more than 10%. Preferably, the subtherapeutic daily dose of the renin-angiotensin-aldosterone system inhibitor and the subtherapeutic daily dose of the HMG-CoA reductase inhibitor together do not change the HDL cholesterol level by more than 15%, preferably more than 12%, most preferably more than 10%, when administered for at least 10 days, preferably at least 14 days, more preferably at least 1 month.

In yet another preferred embodiment, the subtherapeutic daily dose of the renin-angiotensin-aldosterone system inhibitor and the subtherapeutic daily dose of the HMG-CoA reductase inhibitor together do not change the systolic blood pressure in a subject by more than 10%, preferably more than 8%, more preferably more than 6%, most preferably more than 4%. Preferably, the subtherapeutic daily dose of the renin-angiotensin-aldosterone system inhibitor and the subtherapeutic daily dose of the HMG-CoA reductase inhibitor together do not change the systolic blood pressure in a subject by more than 10%, preferably more than 8%, more preferably more than 6%, most preferably more than 4%, when administered for at least 10 days, preferably at least 14 days, more preferably at least 1 month.

In yet another preferred embodiment, the subtherapeutic daily dose of the renin-angiotensin-aldosterone system inhibitor and the subtherapeutic daily dose of the HMG-CoA reductase inhibitor together do not change the diastolic blood pressure in a subject by more than 10%, preferably more than 8%, more preferably more than 6%, most preferably more than 5%. Preferably, the subtherapeutic daily dose of the renin-angiotensin-aldosterone system inhibitor and the subtherapeutic daily dose of the HMG-CoA reductase inhibitor together do not change the diastolic blood pressure in a subject by more than 10%, preferably more than 8%, more preferably more than 6%, most preferably more than 5%, when administered for at least 10 days, preferably at least 14 days, more preferably at least 1 month.

In a preferred embodiment, the subtherapeutic daily dose of the renin-angiotensin-aldosterone inhibitor in the pharmaceutical compositions according to the present invention is between 1 and 50%, preferably between 1 and 25% of the daily recommended therapeutic dose. Preferably, the subtherapeutic daily dose of the renin-angiotensin-aldosterone inhibitor is between 1 and 75 mg, between 1 and 60 mg, between 1 and 50 mg, between 1 and 45 mg, between 1 and 40 mg, and/or between 1 and 25 mg.

In one more preferred embodiment, the renin-angiotensin-aldosterone is valsartan or any pharmaceutically acceptable salts or esters thereof, and the subtherapeutic daily dose is between 1 and 75 mg, preferably between 1 and 60 mg, more preferably between 1 and 50 mg, still more preferably between 1 to 40 mg, most preferably between 10 to 30 mg, particularly preferably 20 mg.

In another more preferred embodiment, the renin-angiotensin-aldosterone is telmisartanor any pharmaceutically acceptable salts or esters thereof, and the subtherapeutical dose thereof is between 1 to 20 mg, preferably between 1 to 10 mg, most preferably 5 mg.

In a preferred embodiment, the subtherapeutic daily dose of the HMG-CoA reductase inhibitor is between 1 to 40 mg, preferably between 1 to 30 mg, more preferably between 1 and 25 mg, still more preferably between 1 and 20 mg, most preferably between 1 and 15 mg, particularly preferably between 1 and 12 mg.

In one more preferred embodiment, the HMG-CoA reductase inhibitor is fluvastatin or any pharmaceutically acceptable salts or esters thereof, and the subtherapeutical dose thereof is between 1 to 20 mg, preferably between 1 to 10 mg, most preferably 10 mg.

In another more preferred embodiment, the HMG-CoA reductase inhibitor is atorvastatin or any pharmaceutically acceptable salts or esters thereof, and the subtherapeutical dose thereof is between 1 to 10 mg, preferably between 1 to 5 mg, most preferably 5 mg.

In one embodiment of the present invention, the pharmaceutical composition comprises at least one renin-angiotensin-aldosterone system inhibitor selected from the group consisting of, but not limited to, renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose, and is suitable for use in maintaining or improving the functional and morphological properties of the arterial wall in a subject having at least one cardiovascular disorder or having at least one risk factor for cardiovascular disorder In preferred embodiment, the pharmaceutical composition comprises at least one angiotensin II receptor antagonist, selected from the group consisting of, but not limited to, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, in a subtherapeutic daily dose and at least one HMG-CoA reductase inhibitor, selected from the group consisting of, but not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof, in a subtherapeutic daily dose, and is suitable for use in maintaining or improving the functional and morphological properties of the arterial wall in a subject having at least one cardiovascular disorder or having at least one risk factor for cardiovascular disorder.

In a more preferred embodiment, the pharmaceutical composition comprises valsartan or any pharmaceutically acceptable salts thereof in a subtherapeutic daily dose and fluvastatin or any pharmaceutically acceptable salts thereof in a subtherapeutic daily dose, and is suitable for use in maintaining or improving the functional and morphological properties of the arterial wall in a subject having at least one cardiovascular disorder or having at least one risk factor for cardiovascular disorder.

In a still more preferred embodiment, the pharmaceutical composition comprises valsartan or any pharmaceutically acceptable salts thereof in a daily dose between 1 and 50%, preferably between 1 and 25% of the daily recommended therapeutic dose and fluvastatin or any pharmaceutically acceptable salts thereof in a daily dose between 1 and 50%, preferably between 1 and 25% of daily recommended therapeutic dose, and is suitable for use in maintaining or improving the functional and morphological properties of the arterial wall in a subject having at least one cardiovascular disorder or having at least one risk factor for cardiovascular disorder.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having at least one cardiovascular disorder or having at least one risk factor for cardiovascular disorder.

In one embodiment, the pharmaceutical composition comprises at least one renin-angiotensin-aldosterone system inhibitor selected from the group consisting of, but not limited to, renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose, and is suitable for use in maintaining or improving the functional and morphological properties of the arterial wall in a subject having
   a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a preferred embodiment, the pharmaceutical composition comprises at least one at least one angiotensin II receptor antagonist, selected from the group consisting of, but not limited to, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, in a subtherapeutic daily dose and at least one HMG-CoA reductase inhibitor, selected from the group consisting of, but not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof, and is suitable for use in maintaining or improving the functional and morphological properties of the arterial wall in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a more preferred embodiment, the pharmaceutical composition comprises valsartan or any pharmaceutically acceptable salts thereof in a subtherapeutic daily dose and fluvastatin or any pharmaceutically acceptable salts thereof in a subtherapeutic daily dose, and is suitable for use in maintaining or improving the functional and morphological properties of the arterial wall in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a still more preferred embodiment, the pharmaceutical composition comprises valsartan or any pharmaceutically acceptable salts thereof in a daily dose that is between 1 and 40 mg and fluvastatin or any pharmaceutically acceptable salts thereof in a daily dose that is between 1 and 10 mg, and is suitable for use in maintaining or improving the functional and morphological properties of the arterial wall in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a yet more preferred embodiment, the pharmaceutical composition comprises valsartan or any pharmaceutically acceptable salts thereof in a daily dose that is between 1 and 40 mg and fluvastatin or any pharmaceutically acceptable salts thereof in a daily dose that is between 1 and 10 mg, and is suitable for use in maintaining or improving the functional and morphological properties of the arterial wall in a subject having
  a) a cardiovascular disorder selected from the group consisting of, but not limited to, myocardial infarction, stroke, vascular dementia and any combinations thereof, or
  b) a disorder which causes a high risk for cardiovascular disorder occurrence selected from the group consisting of, but not limited to, diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, and any combinations thereof.

In a further embodiment, the pharmaceutical composition according to the present invention can be used continuously for the whole life without any break.

It was unexpectedly found out that the effect of maintaining or improving the functional and morphological properties of the arterial wall in a subject having at least one cardiovascular disorder or having at least one risk factor for cardiovascular disorder, when using the pharmaceutical combination composition according to the present invention is surprisingly achieved after treatment defined as a treatment-period, that can last between about 1 week and about 9 months, about 10 days and 9 months, about 2 weeks and 9 months, about 1 month to about 9 months, preferably between about 1 month to about 6 months.

Therefore, in one further embodiment, the present invention relates to a pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having at least one cardiovascular disorder or having at least one risk factor for cardiovascular disorder in a treatment-period lasting between about 1 week and about 9 months, about 10 days and 9 months, about 2 weeks and 9 months, about 1 month to about 9 months, preferably between about 1 month to about 6 months.

In a preferred embodiment, the pharmaceutical composition comprises at least one renin-angiotensin-aldosterone system inhibitor in a subtherapeutic daily dose and at least one HMG-CoA reductase inhibitor in a subtherapeutic daily dose, and is suitable for use in maintaining or improving the functional and morphological properties of the arterial wall in a subject having
  a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or
  b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof, in a treatment-period lasting between about 1 week and about 9 months, about 10 days and 9 months, about 2 weeks and 9 months, about 1 month to about 9 months, preferably between about 1 month to about 6 months.

In another preferred embodiment, the pharmaceutical composition comprises at least one renin-angiotensin-aldosterone system inhibitor in a daily dose between 1 and 50%, preferably between 1 and 25% of daily recommended therapeutic dose and at least one HMG-CoA reductase inhibitor in a daily dose between 1 and 50%, preferably between 1 and 25% of daily recommended therapeutic dose, and is suitable for use in maintaining or improving the functional and morphological properties of the arterial wall in a subject having at least one cardiovascular disorder or having at least one risk factor for cardiovascular disorder in a treatment-period lasting between about 1 month to about 9 months, preferably between about 1 month to about 6 months.

In another preferred embodiment, the pharmaceutical composition comprises at least one renin-angiotensin-aldosterone system inhibitor selected from the group consisting of, but not limited to, renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose, and is suitable for use in maintaining or improving the functional and morphological properties of the arterial wall in a subject having at least one cardiovascular disorder or having at least one risk factor for cardiovascular disorder in a treatment-period lasting between about 1 month to about 9 months, preferably between about 1 month to about 6 months.

In a more preferred embodiment, the pharmaceutical composition comprises at least one angiotensin II receptor antagonist, selected from the group consisting of, but not limited to, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, in a subtherapeutic daily dose and at least one HMG-CoA reductase inhibitor, selected from the group consisting of, but not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof, in a subtherapeutic daily dose, and is suitable for use in maintaining or improving the functional and morphological properties of the arterial wall in a subject having at least one cardiovascular disorder or having at least one risk factor for cardiovascular disorder in a treatment-period lasting between about 1 month to about 9 months, preferably between about 1 month to about 6 months.

In a still more preferred embodiment, the pharmaceutical composition comprises valsartan or any pharmaceutically acceptable salts thereof in a subtherapeutic daily dose and fluvastatin or any pharmaceutically acceptable salts thereof in a subtherapeutic daily dose, and is suitable for use in maintaining or improving the functional and morphological properties of the arterial wall in a subject having at least one cardiovascular disorder or having at least one risk factor for cardiovascular disorder in a treatment-period lasting between about 1 month to about 9 months, preferably between about 1 month to about 6 months.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having at least one cardiovascular disorder or having at least one risk factor for cardiovascular disorder in a treatment-period lasting between about 1 month to about 9 months, preferably between about 1 month to about 6 months.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having
  a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or
  b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof, in a treatment-period lasting between about 1 month to about 9 months, preferably between about 1 month to about 6 months.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having
  a) a cardiovascular disorder selected from the group consisting of, but not limited to, myocardial infarction, stroke, vascular dementia and any combinations thereof, or
  b) a disorder which causes a high risk for cardiovascular disorder occurrence selected from the group consisting of, but not limited to, diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, and any combinations thereof,
  in a treatment-period lasting between about 1 week and about 9 months, about 10 days and 9 months, about 2 weeks and 9 months, about 1 month to about 9 months, preferably between about 1 month to about 6 months.

The inventors observed substantial long term persistence of beneficial arterial characteristics mentioned above. Thus, it was unexpectedly found out that beneficial arterial characteristics when administering the pharmaceutical composition according to the present invention surprisingly persisted in a substantial amount even approximately 12 months, preferably between 1 and 12 months or between 1 and 6 months or between 1 and 3 months after discontinuation of treatment. The period without any treatment according to the present invention and wherein the beneficial arterial characteristics are still present is named as the rest-period. One of the aims of the rest-period is to prevent the occurrence of 'resistance' to therapy leading to decreased efficacy after certain time. If any inhibitory process is induced by treatment which seems to be logical it would be diminished during the rest period. That means that repeating of treatment would not result in a decreased efficacy but rather in a similar or even higher efficacy. Based on that assumption it can be predicted that a very long term of use (decades) could be possible without significantly lost efficacy of treatment. Another important aim of the rest-period is a higher compliance of patients and fewer side effects.

Therefore, in one further embodiment, the present invention relates to the pharmaceutical composition comprising at least one renin-angiotensin-aldosterone system inhibitor in a subtherapeutic daily dose and at least one HMG-CoA reductase inhibitor in a subtherapeutic daily dose for use in maintaining or improving the functional and morphological properties of the arterial wall in a subject having at least one cardiovascular disorder or having at least one risk factor for cardiovascular disorder characterized in that the rest-period is approximately 12 months, preferably between 1 and 12 months or between 1 and 6 months or between 1 and 3 months after discontinuation of the treatment.

In a preferred embodiment, the pharmaceutical composition comprises at least one renin-angiotensin-aldosterone system inhibitor in a subtherapeutic daily dose and at least one HMG-CoA reductase inhibitor in a subtherapeutic daily dose, and is suitable for use in maintaining or improving the functional and morphological properties of the arterial wall in a subject having
  a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof; more preferably myocardial infarction, stroke, vascular dementia and any combinations thereof, or
  b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof,
characterized in that the rest-period is approximately 12 months, preferably between 1 and 12 months or between 1 and 6 months or between 1 and 3 months after discontinuation of the treatment.

In another preferred embodiment, the pharmaceutical composition comprises at least one renin-angiotensin-aldosterone system inhibitor in a daily dose between 1 and 50%, preferably between 1 and 25% of daily recommended therapeutic dose and at least one HMG-CoA reductase inhibitor in a daily dose between 1 and 50%, preferably between 1 and 25% of daily recommended therapeutic dose, and is suitable for use in maintaining or improving the functional and morphological properties of the arterial wall in a subject having at least one cardiovascular disorder or having at least one risk factor for cardiovascular disorder characterized in that the rest-period is approximately 12 months, preferably between 1 and 12 months or between 1 and 6 months or between 1 and 3 months after discontinuation of the treatment.

In another preferred embodiment, the pharmaceutical composition comprises at least one renin-angiotensin-aldosterone system inhibitor selected from the group consisting of, but not limited to, renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose, and is suitable for use in maintaining or improving the functional and morphological properties of the arterial wall in a subject having at least one cardiovascular disorder or having at least one risk factor for cardiovascular disorder characterized in that the rest-period is approximately 12 months, preferably between 1 and 12 months or between 1 and 6 months or between 1 and 3 months after discontinuation of the treatment.

In a more preferred embodiment, the pharmaceutical composition comprises at least one angiotensin II receptor antagonist, selected from the group consisting of but not limited to, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, in a subtherapeutic daily dose and at least one HMG-CoA reductase inhibitor, selected from the group consisting of, but not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof, in a subtherapeutic daily dose, and is suitable for use in maintaining or improving the functional and morphological properties of the arterial wall in a subject having at least one cardiovascular disorder or having at least one risk factor for cardiovascular disorder characterized in that the rest-period is approximately 12 months, preferably between 1 and 12 months or between 1 and 6 months or between 1 and 3 months after discontinuation of the treatment.

In a still more preferred embodiment, the pharmaceutical composition comprises valsartan or any pharmaceutically acceptable salts thereof in a subtherapeutic daily dose and fluvastatin or any pharmaceutically acceptable salts thereof in a subtherapeutic daily dose, and is suitable for use in maintaining or improving the functional and morphological properties of the arterial wall in a subject having at least one cardiovascular disorder or having at least one risk factor for cardiovascular disorder characterized in that the rest-period is approximately 12 months, preferably between 1 and 12 months or between 1 and 6 months or between 1 and 3 months after discontinuation of the treatment.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having at least one cardiovascular disorder or having at least one risk factor for cardiovascular disorder characterized in that the rest-period is approximately 12 months, preferably between 1 and 12 months or between 1 and 6 months or between 1 and 3 months after discontinuation of the treatment.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having
  a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or
  b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof,
characterized in that the rest-period is approximately 12 months, preferably between 1 and 12 months or between 1 and 6 months or between 1 and 3 months after discontinuation of the treatment.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in maintaining or improving the functional and morphological properties of the arterial wall in a subject having
  a) a cardiovascular disorder selected from the group consisting of, but not limited to, myocardial infarction, stroke, vascular dementia and any combinations thereof, or
  b) a disorder which causes a high risk for cardiovascular disorder occurrence selected from the group consisting of, but not limited to, diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, and any combinations thereof,
characterized in that the rest-period is approximately 12 months, preferably between 1 and 12 months or between 1 and 6 months or between 1 and 3 months after discontinuation of the treatment.

Another concept of the present invention relates to a specific, original approach for implementation of the above mentioned obtained beneficial arterial characteristics by the following treatment regime: one treatment-period followed by one rest-period represents one intervention-cycle that can be repeated unrestricted times through years or decades.

It is well known from the state of the art that functional and morphological properties of arterial wall have high predictive values and have important casually role on worsening or occurrence of cardiovascular disorders. At the same time, it is well known that age (chronological or biological age) is one of the most important risk factor for the worsening or occurrence of cardiovascular disorders. On the other hand, it is also well known that cardiovascular disorders themselves simultaneously accelerate the arterial aging and biological aging. Hence, it is clear from the mentioned above that arterial age is a risk factor for cardiovascular disorders. Therefore, the prevention, reduction and/or reversal of arterial aging results in decreased risk for cardiovascular disorders. Putting all these facts together, it can be concluded that improvement in arterial wall properties should be a pivotal aim in decreasing both arterial age and risk for cardiovascular disorder. By said approach simultaneous achievement of two tremendously important aims:
  decreasing arterial age, and
  decreasing worsening or occurrence of cardiovascular disorders
is assured, thereby extending the duration and quality of life.

Therefore, in one further embodiment, the present invention is relates to a pharmaceutical composition comprising at least one renin-angiotensin-aldosterone system inhibitor in a subtherapeutic daily dose and at least one HMG-CoA reductase inhibitor in a subtherapeutic daily dose for use in the prevention, reduction and/or reversal of arterial aging in a subject having at least one cardiovascular disorder or having at least one risk factor for cardiovascular disorder.

In a preferred embodiment, the pharmaceutical composition comprises at least one renin-angiotensin-aldosterone system inhibitor in a subtherapeutic daily dose and at least one HMG-CoA reductase inhibitor in a subtherapeutic daily dose, and is suitable for use in the prevention, reduction and/or reversal of arterial aging in a subject having
  a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or
  b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof; preferably diabetes, metabolic syndrome, hypercholesterolemia, hypertension, and any combinations thereof, more preferably diabetes, metabolic syndrome, arterial hypertension, hypercholesterolemia, and any combinations thereof, or
  c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In another preferred embodiment, the pharmaceutical composition comprises at least one renin-angiotensin-aldosterone system inhibitor in a daily dose between 1 and 50%, preferably between 1 and 25% of daily recommended therapeutic dose and at least one HMG-CoA reductase inhibitor in a daily dose between 1 and 50%, preferably between 1 and 25% of daily recommended therapeutic dose, and is suitable for use in prevention, reduction and/or reversal of arterial aging in a subject having at least one cardiovascular disorder or having at least one risk factor for cardiovascular disorder.

In another preferred embodiment, the pharmaceutical composition comprises at least one renin-angiotensin-aldosterone system inhibitor selected from the group consisting of, but not limited to, renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose, and is suitable for use in the prevention, reduction and reversal of the arterial age in a subject having at least one cardiovascular disorder or having at least one risk factor for cardiovascular disorder.

In a more preferred embodiment, the pharmaceutical composition comprises at least one angiotensin II receptor antagonist, selected from the group consisting of; but not limited to, azilsartan, losartan, eprosartan, irbesartan, olmesartan, candesartan, valsartan and telmisartan and any pharmaceutically acceptable salts or esters thereof; preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, in a subtherapeutic daily dose and at least one HMG-CoA reductase inhibitor, selected from the group consisting of, but not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof, in a subtherapeutic daily dose, and is suitable for use in the prevention, reduction and reversal of arterial aging in a subject having at least one cardiovascular disorder or having at least one risk factor for cardiovascular disorder.

In a still more preferred embodiment, the pharmaceutical composition comprises valsartan or any pharmaceutically acceptable salts thereof in a subtherapeutic daily dose and fluvastatin or any pharmaceutically acceptable salts thereof in a subtherapeutic daily dose, and is suitable for use in the prevention, reduction and/or reversal of arterial aging in a subject having at least one cardiovascular disorder or having at least one risk factor for cardiovascular disorder.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in the prevention, reduction and/or reversal of arterial aging in a subject having at least one cardiovascular disorder or having at least one risk factor for cardiovascular disorder.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose less between 1 and 10 mg, and is suitable for use in the prevention, reduction and/or reversal of arterial aging in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg, and is suitable for use in the prevention, reduction and/or reversal of arterial aging in a subject having a) a cardiovascular disorder selected from the group consisting of, but not limited to, myocardial infarction, stroke, vascular dementia and any combinations thereof, or b) a disorder which causes a high risk for cardiovascular disorder occurrence selected from the group consisting of, but not limited to, diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, and any combinations thereof.

In one further embodiment, the present invention relates to a pharmaceutical composition comprising at least one renin-angiotensin-aldosterone system inhibitor in a subtherapeutic daily dose and at least one HMG-CoA reductase inhibitor in a subtherapeutic daily dose for use in decreasing worsening or occurrence of cardiovascular disorders in a subject having at least one cardiovascular disorder or having at least one risk factor for cardiovascular disorder.

In a preferred embodiment, the pharmaceutical composition comprises at least one renin-angiotensin-aldosterone system inhibitor in a subtherapeutic daily dose and at least one HMG-CoA reductase inhibitor in a subtherapeutic daily dose, and is suitable for use in decreasing worsening or occurrence of cardiovascular disorders in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In another preferred embodiment, the pharmaceutical composition comprises at least one renin-angiotensin-aldosterone system inhibitor in a daily dose between 1 and 50%, preferably between 1 and 25% of daily recommended therapeutic dose and at least one HMG-CoA reductase inhibitor in a daily dose between 1 and 50%, preferably between 1 and 25% of daily recommended therapeutic dose, and is suitable for use in decreasing worsening or occurrence of cardiovascular disorders in a subject having at least one cardiovascular disorder or having at least one risk factor for cardiovascular disorder.

In another preferred embodiment, the pharmaceutical composition comprises at least one renin-angiotensin-aldosterone system inhibitor selected from the group consisting of, but not limited to, renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose, and is suitable for use in decreasing worsening or occurrence of cardiovascular disorders in a subject having at least one cardiovascular disorder or having at least one risk factor for cardiovascular disorder.

In a more preferred embodiment, the pharmaceutical composition comprises at least one angiotensin II receptor antagonist, selected from the group consisting of, but not limited to, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof, in a subtherapeutic daily dose and at least one HMG-CoA reductase inhibitor, selected from the group consisting of, but not limited to, mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof, in a subtherapeutic daily dose, and is suitable for use in decreasing worsening or occurrence of cardiovascular disorders in a subject having at least one cardiovascular disorder or having at least one risk factor for cardiovascular disorder.

In a still more preferred embodiment, the pharmaceutical composition comprises valsartan or any pharmaceutically acceptable salts thereof in a subtherapeutic daily dose and fluvastatin or any pharmaceutically acceptable salts thereof in a subtherapeutic daily dose, and is suitable for use in decreasing worsening or occurrence of cardiovascular disorders in a subject having at least one cardiovascular disorder or having at least one risk factor for cardiovascular disorder.

In a yet more preferred embodiment, the pharmaceutical composition comprising valsartan or any pharmaceutically acceptable salts thereof in a daily dose between 1 and 40 mg and fluvastatin or any pharmaceutically acceptable salts thereof in a daily dose between 1 and 10 mg, and is suitable for use in decreasing worsening or occurrence of cardiovascular disorders in a subject having at least one cardiovascular disorder or having at least one risk factor for cardiovascular disorder.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg for use in decreasing worsening or occurrence of cardiovascular disorders in a subject having a) a cardiovascular disorder selected from the group consisting of, but not limited to, ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof, or b) a disorder which causes a high risk for cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or c) a risky life style which causes a high risk for cardiovascular disorder occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

In a yet more preferred embodiment, the pharmaceutical composition comprises valsartan or any pharmaceutically acceptable salts thereof in a daily dose between 1 and 40 mg and fluvastatin or any pharmaceutically acceptable salts thereof in a daily dose between 1 and 10 mg for use in decreasing worsening or occurrence of cardiovascular disorders in a subject having a) a cardiovascular disorder selected from the group consisting of, but not limited to, myocardial infarction, stroke, vascular dementia and any combinations thereof, or b) a disorder which causes a high risk for cardiovascular disorder occurrence selected from the group consisting of, but not limited to, diabetes, metabolic syndrome, arterial hypertension, hypercholesterolemia, and any combinations thereof, or c) a risky life style which causes a high risk for cardiovascular occurrence selected from the group consisting of, but not limited to, smoking, obesity, and any combinations thereof.

In a preferred embodiment, the subjects according to the present invention are mammals, preferably human subjects.

As already indicated above, the pharmaceutical composition according to the present invention is suitable for use in maintaining or improving the functional and morphological properties of the arterial wall, the prevention, reduction or reversal of arterial aging, and/or decreasing the worsening or the occurrence of cardiovascular disorders, in unhealthy subjects, subjects having at least one cardiovascular disorder, and/or subjects having at least one risk factor for a cardiovascular disorder.

In a preferred embodiment, maintaining or improving the functional and morphological properties of the arterial wall, the prevention, reduction or reversal of arterial aging, and/or decreasing the worsening or the occurrence of cardiovascular disorders, is achieved after treatment for at least 1 week, preferably for at least 10 days, preferably for at least 2 weeks, more preferably for at least 1 month.

The advantageous effects of the pharmaceutical compositions according to the invention can e.g. be determined by the changes of the FMD, the PWV and the beta-stiffness after treatment.

In one embodiment, the flow-mediated dilatation of brachial artery (FMD) after a period of treatment, preferably after 1 month of treatment, is increased compared to the beginning of the treatment.

In another embodiment, the pulse-wave velocity (PWV) after a period of treatment, preferably after 1 month of treatment, is decreased compared to the beginning of the treatment.

In yet another embodiment, the β-stiffness of carotid artery after a period of treatment, preferably after 1 month of treatment, is decreased compared to the beginning of the treatment.

In yet another embodiment, the pulse-wave velocity (PWV) and the β-stiffness of carotid artery after 1 month of treatment are decreased compared to the beginning of the treatment.

In a preferred embodiment of the invention, the FMD increases by at least 20%, preferably at least 35%, more preferably at least 50%, most preferably at least 60% after a treatment period, preferably 1 month of treatment.

In a more preferred embodiment, the FMD in a subject having a risk for a coronary heart disease (10-year risk) according to the Framingham Risk score of more than 10%, preferably from more than 10 to 20%, more preferably from 14 to 18%, increases by at least 60%, preferably at least 100%, more preferably at least 120%, most preferably at least 135% after a treatment period, preferably 1 month of treatment.

In another more preferred embodiment, the FMD in a subject having a risk for a coronary heart disease (10-year risk) according to the Framingham Risk score of more than 20%, preferably from 20 to 30%, more preferably from 25 to 29%, increases by at least 60%, preferably at least 90%, more preferably at least 110%, most preferably at least 120% after a treatment period, preferably 1 month of treatment.

In yet another more preferred embodiment, the FMD in a subject having at least one cardiovascular disorder, wherein the cardiovascular disorder is preferably post-myocardial infarction, increases by at least 30%, preferably at least 45%, more preferably at least 60%, most preferably at least 65% after a treatment period, preferably 1 month of treatment.

In yet another more preferred embodiment, the FMD in a subject having at least one risk factor for a cardiovascular disorder, wherein the risk factor is a disorder preferably selected from the group consisting of diabetes mellitus type 1, diabetes mellitus type 2, arterial hypertension, hypercholesterolemia and any combinations thereof, increases by at least 20%, preferably at least 35%, more preferably at least 50%, most preferably at least 60% after a treatment period, preferably 1 month of treatment. Preferably, the FMD in a subject having diabetes mellitus type 1 increases by at least 40%, preferably at least 60%, more preferably at least 70%, most preferably at least 75% after a treatment period, preferably 1 month of treatment. Preferably, the FMD in a subject having diabetes mellitus type 2 increases by at least 40%, preferably at least 55%, more preferably at least 65%, most preferably at least 70% after a treatment period, preferably 1 month of treatment.

In yet another more preferred embodiment, the FMD in a subject having at least one risk factor for a cardiovascular disorder, wherein the risk factor is a risky life style preferably selected from the group consisting of smoking, obesity and a combination thereof, increases by at least 100%, preferably at least 120%, more preferably at least 140%, most preferably at least 150% after a treatment period, preferably 1 month of treatment.

In another preferred embodiment of the invention, the PWV decreases by at least 2%, preferably at least 3%, more preferably at least 4%, most preferably at least 4.5% after a treatment period, preferably 1 month of treatment.

In a more preferred embodiment, the PWV in a subject having a risk for a coronary heart disease (10-year risk) according to the Framingham Risk score of more than 10%, preferably from 10 to 20%, more preferably from 14 to 18%, decreases by at least 2%, preferably at least 3%, more preferably at least 4%, most preferably at least 4.2% after a treatment period, preferably 1 month of treatment.

In another more preferred embodiment, the PWV in a subject having a risk for a coronary heart disease (10-year risk) according to the Framingham Risk score of more than 20%, preferably from 20 to 30%, more preferably from 25 to 29%, decreases by at least 2%, preferably at least 3%, more preferably at least 3.5%, most preferably at least 4% after a treatment period, preferably 1 month of treatment.

In yet another more preferred embodiment, the PWV in a subject having at least one cardiovascular disorder, wherein the cardiovascular disorder is preferably post-myocardial infarction, decreases by at least 3%, preferably at least 5%, more preferably at least 6%, most preferably at least 7% after a treatment period, preferably 1 month of treatment.

In yet another more preferred embodiment, the PWV in a subject having at least one risk factor for a cardiovascular disorder, wherein the risk factor is a disorder preferably selected from the group consisting of diabetes mellitus type 1, diabetes mellitus type 2, arterial hypertension, hypercholesterolemia, and any combinations thereof, decreases by at least 2%, preferably at least 3%, more preferably at least 4%, most preferably at least 4.2% after a treatment period, preferably 1 month of treatment. Preferably, the PWV in a subject having diabetes mellitus type 1 decreases by at least 3%, preferably at least 5%, more preferably at least 6%, most preferably at least 7% after a treatment period, preferably 1 month of treatment. Preferably, the PWV in a subject having diabetes mellitus type 2 decreases by at least 4%, preferably at least 6%, more preferably at least 8%, most preferably at least 8.2% after a treatment period, preferably 1 month of treatment.

In yet another more preferred embodiment, the PWV in a subject having at least one risk factor for a cardiovascular disorder, wherein the risk factor is a risky life style preferably selected from the group consisting of smoking, obesity and a combination thereof, decreases by at least 2%, preferably at least 4%, more preferably at least 5%, most preferably at least 6% after a treatment period, preferably 1 month of treatment.

In another preferred embodiment of the invention, the β-stiffness decreases by at least 2%, preferably at least 4%, more preferably at least 6%, most preferably at least 7.2% after a treatment period, preferably 1 month of treatment.

In a more preferred embodiment, the β-stiffness in a subject having a risk for a coronary heart disease (10-year risk) according to the Framingham Risk score of more than 10%, preferably from 10 to 20%, more preferably from 14 to 18%, decreases by at least 3%, preferably at least 5%, more preferably at least 6%, most preferably at least 6.5% after a treatment period, preferably 1 month of treatment.

In another more preferred embodiment, the β-stiffness in a subject having a risk for a coronary heart disease (10-year risk) according to the Framingham Risk score of more than 20%, preferably from 20 to 30%, more preferably from 25 to 29%, decreases by at least 2%, preferably at least 3%, more preferably at least 3.5%, most preferably at least 4% after a treatment period, preferably 1 month of treatment.

In yet another more preferred embodiment, the β-stiffness in a subject having at least one cardiovascular disorder, wherein the cardiovascular disorder is preferably post-myocardial infarction, decreases by at least 3%, preferably at least 5%, more preferably at least 6%, most preferably at least 6.5% after a treatment period, preferably 1 month of treatment.

In yet another more preferred embodiment, the β-stiffness in a subject having at least one risk factor for a cardiovascular disorder, wherein the risk factor is a disorder preferably selected from the group consisting of diabetes mellitus type 1, diabetes mellitus type 2, arterial hypertension or hypercholesterolemia, decreases by at least 2%, preferably at least 4%, more preferably at least 6%, most preferably at least 7% after a treatment period, preferably 1 month of treatment. Preferably, the β-stiffness in a subject having diabetes mellitus type 1 decreases by at least 4%, preferably at least 6%, more preferably at least 8%, most preferably at least 10% after a treatment period, preferably 1 month of treatment. Preferably, the β-stiffness in a subject having diabetes mellitus type 2 decreases by at least 3%, preferably at least 5%, more preferably at least 6%, most preferably at least 7% after a treatment period, preferably 1 month of treatment.

In yet another preferred embodiment, the β-stiffness in a subject having at least one risk factor for a cardiovascular disorder, wherein the risk factor is a risky life style preferably selected from the group consisting of smoking, obesity and a combination thereof, decreases by at least 2%, preferably at least 4%, more preferably at least 6%, most preferably at least 8% after a treatment period, preferably 1 month of treatment.

In one embodiment of the present invention, the pharmaceutical compositions are characterized in that after discontinuation of the treatment for at least 3 months, preferably at least 6 months, the residual improvement of the FMD is at least 20%, preferably at least 30%, more preferably at least 40%, most preferably at least 50% based on the increase of the FMD after a period of treatment.

In a preferred embodiment, after discontinuation of the treatment for at least 3 months, preferably at least 6 months, the residual improvement of the FMD in a subject having a risk for a coronary heart disease (10-year risk) according to the Framingham Risk score of more than 10%, preferably from 10 to 20%, more preferably from 14 to 18%, is at least 45%, preferably at least 55%, more preferably at least 65%, most preferably at least 75% based on the increase of the FMD after a period of treatment.

In another preferred embodiment, after discontinuation of the treatment for at least 3 months, preferably at least 6 months, the residual improvement of the FMD in a subject having a risk for a coronary heart disease (10-year risk) according to the Framingham Risk score of more than 20%, preferably from 20 to 30%, more preferably from 25 to 29%, is at least 40%, preferably at least 50%, more preferably at least 60%, most preferably at least 70% based on the increase of the FMD after a period of treatment.

In yet another preferred embodiment, after discontinuation of the treatment for at least 3 months, preferably at least 6 months, the residual improvement of the FMD in a subject having at least one cardiovascular disorder, wherein the cardiovascular disorder is preferably post-myocardial infarction, is at least 50%, preferably at least 60%, more preferably at least 70%, most preferably at least 80% based on the increase of the FMD after a period of treatment.

In yet another preferred embodiment, after discontinuation of the treatment for at least 3 months, preferably at least 6 months, the residual improvement of the FMD in a subject having at least one risk factor for a cardiovascular disorder, wherein the risk factor is a disorder preferably selected from the group consisting of diabetes mellitus type 1, diabetes mellitus type 2, arterial hypertension, hypercholesterolemia and any combinations thereof, is at least 20%, preferably at least 30%, more preferably at least 40%, most preferably at least 50% based on the increase of the FMD after a period of treatment. Preferably, after discontinuation of the treatment for at least 3 months, preferably at least 6 months, the residual improvement of the FMD in a subject having diabetes mellitus type 1 is at least 30%, preferably at least 40%, more preferably at least 50%, most preferably at least 60% based on the increase of the FMD after a period of treatment. Preferably, after discontinuation of the treatment for at least 3 months, preferably at least 6 months, the residual improvement of the FMD in a subject having diabetes mellitus type 2 is at least 50%, preferably at least 60%, more preferably at least 70%, most preferably at least 80% based on the increase of the FMD after a period of treatment.

In yet another preferred embodiment, after discontinuation of the treatment for at least 3 months, preferably at least 6 months, the residual improvement of the FMD in a subject having at least one risk factor for a cardiovascular disorder, wherein the risk factor is a risky life style preferably selected from the group consisting of smoking, obesity and a combination thereof, is at least 20%, preferably at least 30%, more preferably at least 40%, most preferably at least 50% based on the increase of the FMD after a period of treatment.

In one further embodiment of the present invention, the pharmaceutical compositions are characterized in that after discontinuation of the treatment for at least 3 months, preferably at least 6 months, the residual improvement of the PWV is at least 20%, preferably at least 30%, more preferably at least 40%, most preferably at least 50% based on the decrease of the PWV after a period of treatment.

In a preferred embodiment, after discontinuation of the treatment for at least 3 months, preferably at least 6 months, the residual improvement of the PWV in a subject having a risk for a coronary heart disease (10-year risk) (according to the Framingham Risk score of more than 10%, preferably from 10 to 20%, more preferably from 14 to 18%); is at least 35%, preferably at least 45%, more preferably at least 55%, most preferably at least 65% based on the decrease of the PWV after a period of treatment.

In another preferred embodiment, after discontinuation of the treatment for at least 3 months, preferably at least 6 months, the residual improvement of the PWV in a subject having a risk for a coronary heart disease (10-year risk) (according to the Framingham Risk score of more than 20%, preferably from 20 to 30%, more preferably from 25 to 29%) is at least 30%, preferably at least 40%, more preferably at least 50%, most preferably at least 60% based on the decrease of the PWV after a period of treatment.

In yet another preferred embodiment, after discontinuation of the treatment for at least 3 months, preferably at least 6 months, the residual improvement of the PWV in a subject having at least one cardiovascular disorder, wherein the cardiovascular disorder is preferably post-myocardial infarction, is at least 40%, preferably at least 50%, more preferably at least 60%, most preferably at least 70% based on the decrease of the PWV after a period of treatment.

In yet another preferred embodiment, after discontinuation of the treatment for at least 3 months, preferably at least 6 months, the residual improvement of the PWV in a subject having at least one risk factor for a cardiovascular disorder, wherein the risk factor is a disorder preferably selected from the group consisting of diabetes mellitus type 1, diabetes mellitus type 2, arterial hypertension, hypercholesterolemia and any combinations thereof, is at least 20%, preferably at least 30%, more preferably at least 40%, most preferably at least 50% based on the decrease of the PWV after a period of treatment. Preferably, after discontinuation of the treatment for at least 3 months, preferably at least 6 months, the residual improvement of the PWV in a subject having diabetes mellitus type 1 is at least 30%, preferably at least 40%, more preferably at least 50%, most preferably at least 60% based on the decrease of the PWV after a period of treatment. Preferably, after discontinuation of the treatment for at least 3 months, preferably at least 6 months, the residual improvement of the PWV in a subject having diabetes mellitus type 2 is at least 40%, preferably at least 50%, more preferably at least 60%, most preferably at least 70% based on the decrease of the PWV after a period of treatment.

In yet another preferred embodiment, after discontinuation of the treatment for at least 3 months, preferably at least 6 months, the residual improvement of the PWV in a subject having at least one risk factor for a cardiovascular disorder, wherein the risk factor is a risky life style preferably selected from the group consisting of smoking, obesity and a combination thereof, is at least 25%, preferably at least 35%, more preferably at least 45%, most preferably at least 55% based on the decrease of the PWV after a period of treatment.

In one further embodiment of the present invention, the pharmaceutical compositions are characterized in that after discontinuation of the treatment for at least 3 months, preferably at least 6 months, the residual improvement of the β-stiffness is at least 15%, preferably at least 25%, more preferably at least 35%, most preferably at least 45% based on the decrease of the β-stiffness after a period of treatment.

In a preferred embodiment, after discontinuation of the treatment for at least 3 months, preferably at least 6 months, the residual improvement of the β-stiffness in a subject having a risk for a coronary heart disease (10-year risk) (according to the Framingham Risk score of more than 10%, preferably from 10 to 20%, more preferably from 14 to 18%), is at least 30%, preferably at least 40%, more preferably at least 50%, most preferably at least 60% based on the decrease of the β-stiffness after a period of treatment.

In another preferred embodiment, after discontinuation of the treatment for at least 3 months, preferably at least 6 months, the residual improvement of the β-stiffness in a subject having a risk for a coronary heart disease (10-year risk) (according to the Framingham Risk score of more than 20%, preferably from 20 to 30%, more preferably from 25 to 29%), is at least 25%, preferably at least 35%, more preferably at least 45%, most preferably at least 55% based on the decrease of the β-stiffness after a period of treatment.

In yet another preferred embodiment, after discontinuation of the treatment for at least 3 months, preferably at least 6 months, the residual improvement of the β-stiffness in a subject having at least one cardiovascular disorder, wherein the cardiovascular disorder is preferably post-myocardial infarction, is at least 40%, preferably at least 50%, more preferably at least 60%, most preferably at least 70% based on the decrease of the (3-stiffness after a period of treatment.

In yet another preferred embodiment, after discontinuation of the treatment for at least 3 months, preferably at least 6 months, the residual improvement of the β-stiffness in a subject having at least one risk factor for a cardiovascular disorder, wherein the risk factor is a disorder preferably selected from the group consisting of diabetes mellitus type 1, diabetes mellitus type 2, arterial hypertension, hypercholesterolemia and any combinations thereof, is at least 15%, preferably at least 25%, more preferably at least 35%, most preferably at least 45% based on the decrease of the β-stiffness after a period of treatment. Preferably, after discontinuation of the treatment for at least 3 months, preferably at least 6 months, the residual improvement of the β-stiffness in a subject having diabetes mellitus type 1 is at least 25%, preferably at least 35%, more preferably at least 45%, most preferably at least 55% based on the decrease of the β-stiffness after a period of treatment. Preferably, after discontinuation of the treatment for at least 3 months, preferably at least 6 months, the residual improvement of the β-stiffness in a subject having diabetes mellitus type 2 is at least 40%, preferably at least 50%, more preferably at least 60%, most preferably at least 70% based on the decrease of the β-stiffness after a period of treatment.

In yet another preferred embodiment, after discontinuation of the treatment for at least 3 months, preferably at least 6 months, the residual improvement of the β-stiffness in a subject having at least one risk factor for a cardiovascular disorder, wherein the risk factor is a risky life style preferably selected from the group consisting of smoking, obesity and a combination thereof, is at least 20%, preferably at least 30%, more preferably at least 40%, most preferably at least 50% based on the decrease of the (3-stiffness after a period of treatment.

In one embodiment of the present invention, the subject is treated over a treatment period of at least one week, preferably, at least 2 weeks, more preferably at least 1 month, still more preferably from about 1 to about 9 months, most preferably from about 1 to about 3 months, particularly preferably about 1 month.

In one further embodiment, the subject is treated over at least one intervention-cycle, wherein one intervention-cycle comprises a treatment period of 1 to 9 months of treatment, preferably 1 to 3 months of treatment, more preferably 1 month of treatment, and a rest period of 1 to 12 months of discontinuation of treatment, preferably 1 to 6 months of discontinuation of treatment, more preferably about 6 months of discontinuation of treatment.

In a preferred embodiment, the FMD is still increased by at least 10%, preferably at least 15%, more preferably at least 20%, most preferably at least 25% after 1 month of treatment and after 6 months of discontinuation of treatment.

In more preferred embodiment, the FMD in a subject having diabetes mellitus type 1 is still increased by at least 30%, preferably at least 45%, more preferably at least 54%, most preferably at least 57% after 1 month of treatment and after 6 months of discontinuation of treatment. In another more preferred embodiment, the FMD in a subject having diabetes mellitus type 2 is still increased by at least 60%, preferably at least 80%, more preferably at least 92%, most preferably at least 100% after 1 month of treatment and after 6 months of discontinuation of treatment.

In a preferred embodiment, the PWV is still decreased by at least 1%, preferably at least 1.5%, more preferably at least 2%, most preferably at least 2.1% after 1 month of treatment and after 6 months of discontinuation of treatment.

In more preferred embodiment, the PWV in a subject having diabetes mellitus type 1 is still decreased by at least 2.4%, preferably at least 3.6%, more preferably at least 4.8%, most preferably at least 6.3% after 1 month of treatment and after 6 months of discontinuation of treatment. In another more preferred embodiment, the PWV in a subject having diabetes mellitus type 2 is still decreased by at least 2.8%, preferably at least 4.2%, more preferably at least 5.6%, most preferably at least 7.7% after 1 month of treatment and after 6 months of discontinuation of treatment.

In a preferred embodiment, the β-stiffness is still decreased by at least 0.9%, preferably at least 1.8%, more preferably at least 2.7%, most preferably at least 3.4% after 1 month of treatment and after 6 months of discontinuation of treatment.

In a more preferred embodiment, the β-stiffness in a subject having diabetes mellitus type 1 is still decreased by at least 2.2%, preferably at least 3.3%, more preferably at least 4.4%, most preferably at least 5.5% after 1 month of treatment and after 6 months of discontinuation of treatment. In another more preferred embodiment, the β-stiffness in a subject having diabetes mellitus type 2 is still decreased by at least 2.8%, preferably at least 4.2%, more preferably at least 5.6%, most preferably at least 6.3% after 1 month of treatment and after 6 months of discontinuation of treatment.

The term pharmaceutical composition according to the present invention may mean that each component of the composition is administered to the subject separately in an individual dosage form simultaneously, separately or sequentially in any order. The present invention furthermore relates to a commercial package comprising the pharmaceutical composition according to the present invention together with instructions for simultaneous, separate or sequential use.

Alternatively the term pharmaceutical composition according to the present invention may mean that all or just some components of the compositions are administered to the subject in the same unit dosage form. The combination of two or more active agents in the same pharmaceutical composition provides the additional advantage of reducing the frequency of administration of a dosage, thereby increasing the safety of the therapy and it is more patient friendly.

The pharmaceutical composition of the present invention may further comprise one or more other active ingredient that does not belong to the class of RAAS inhibitors or HMG-CoA reductase inhibitors. For example the pharmaceutical composition according to the present invention may comprise at least one anti-inflammatory agent or at least one antioxidant.

Thus, it is one preferred embodiment of the present invention that the pharmaceutical composition comprises a further active agent, preferably selected from the group consisting of an anti-inflammatory agent, an antioxidant, and combinations thereof.

The term anti-inflammatory agent as used in the present invention can include, but is not limited to, classic non-steroidal antiinflammatory agents (NSAIDS), such as for example acetylsalicyclic acid, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nabumetone, acetaminophen and any pharmaceutically acceptable salts thereof; COX-2 inhibitors, such as for example nimesulide, flosulid, celecoxib, rofecoxib, parecoxib sodium, valdecoxib, etoricoxib, etodolac, meloxicam and any pharmaceutically acceptable salts thereof; glucocorticoids, such as for example hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, rapamycin and any pharmaceutically acceptable salts thereof; resveratrol and any analogues of these agents. Preferably anti-inflammatory agent can be selected from the group consisting of, but not limited to, acetylsalicyclic acid, ketoprofen, ibuprofen, naproxen, celecoxib, rofecoxib, meloxicam, hydrocortisone, cortisone, prednisone, prednisolone, betamethasone, dexamethasone, resveratrol and any pharmaceutically acceptable salts thereof and/or any analogues, more preferably acetylsalicyclic acid, ibuprofen, celecoxib, hydrocortisone, dexamethasone, resveratrol and any pharmaceutically acceptable salts thereof and/or any analogues of these agents, and even more preferably acetylsalicyclic acid and resveratrol and any pharmaceutically acceptable salts thereof and/or any analogues thereof.

According to one embodiment of the present invention, the anti-inflammatory agent is present in the pharmaceutical composition in the efficient amount to reduce inflammation.

The term antioxidant as used in the present invention can include, but is not limited to, butylated hydroxyanisole, butylated hydroxytoluene, malic acid, ascorbyl palmitate, sodium ascorbate, sodium metabisulphite, propyl gallate, beta-carotene, ascorbic acid, sodium ascorbyl phosphate, magnesium ascorbyl phosphate, ascorbic acid-2-glycoside, ascorbyl palmitate, ascorbyl stearate, α-lipoic acid, glutathione, coenzyme Q10, tocopherol, tocopherol acetate, retinol, retinol palmitate, genistein, quercetin, epigallocatechin, epigallocatechin gallate, gallocatechin gallate, sylibin, diosmetin, kaempferol, epicatechin, galangin, indolic acid, γ-linolenic acid, linoleic acid, chlorogenic acid, tocotrienol, astaxanthin, and any pharmaceutically acceptable salts thereof and/or any analogues thereof. Preferably, the antioxidant can be selected from the group consisting of, but not limited to, ascorbic acid, sodium ascorbyl phosphate, coenzyme Q10, magnesium ascorbyl phosphate, ascorbic acid-2-glycoside, butylated hydroxyanisole, chlorogenic acid, epigallocatechin gallate, indolic acid, α-lipoic acid and any pharmaceutically acceptable salts thereof and/or any analogues thereof, more preferably ascorbic acid, sodium ascorbyl phosphate, coenzyme Q10, magnesium ascorbyl phosphate, ascorbic acid-2-glycoside, butylated hydroxyanisole and any pharmaceutically acceptable salts thereof and/or any analogues thereof and even more preferably coenzyme Q10 and any pharmaceutically acceptable salts thereof and/or any analogue thereof.

According to one embodiment of the present invention, the antioxidant is present in the pharmaceutical composition in the efficient amount to inhibit oxidation.

In a preferred embodiment, the pharmaceutical composition of the present invention further comprises an anti-inflammatory agent and an antioxidant, which is not vitamin C or vitamin E.

In another preferred embodiment, the pharmaceutical composition of the present invention further comprises an anti-inflammatory agent, but not an antioxidant.

In yet another preferred embodiment, the pharmaceutical composition of the present invention further comprises an antioxidant and an anti-inflammatory agent, which is not acetylsalicylic acid.

In yet another preferred embodiment, the pharmaceutical composition of the present invention further comprises an antioxidant, but not an anti-inflammatory agent.

In yet another preferred embodiment, the pharmaceutical composition of the present invention further comprises an anti-inflammatory agent and/or an antioxidant, wherein the anti-inflammatory agent is resveratrol, and the antioxidant is coenzyme Q10 or any analogue thereof.

In one further embodiment of the present invention, the pharmaceutical composition further comprises one or more pharmaceutically acceptable excipients. The term 'pharmaceutically acceptable' as employed herein refers to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio. The term 'pharmaceutically acceptable excipient' means a component of a pharmaceutical product that is not an active ingredient. Useful pharmaceutically acceptable excipients of the present invention include, but are not limited to, diluents, disintegrants, binders, lubricants, antioxidants, surfactants, pH modifiers, antiadherants, pigments, colorants and the like, and any combinations thereof.

The pharmaceutical composition according to the present invention may be administered to the subject by any known route of administration such as for example peroral (mouth), topical (skin), parenteral (skin or mucous membrane), transmucosal (nasal, buccal/sublingual, vaginal, occular, rectal) or inhalation. The pharmaceutical composition according to the present invention may be useful for immediate-, delayed-, modified-, sustained-, extended-, pulsed-, continuous- or controlled-release applications. The pharmaceutical composition according to the present invention may be prepared by any process known from the state of the art.

The pharmaceutical composition according to the present invention suitable for peroral administration may take the form of, but is not limited to, solution, suspension, emulsion, tablet, pill, gel, syrup, elixir, capsule, powder, liquid or solid crystal, paste, and the like.

The pharmaceutical composition according to the present invention suitable for topical administration may take the form of, but are not limited to, cream, gel, liniment or balm, lotion, ointment, ear drops, eye drops, skin patch and the like.

The pharmaceutical composition according to the present invention suitable for parenteral administration may refer to modes of administration which include, but are not limited to, intradermal, intraosseous, intravenous, intramuscular, intraperitoneal, intrasternal, subcutaneous and intraarticular injection and infusion.

The pharmaceutical composition according to the present invention suitable for inhalation may take the form of, but is not limited to, aerosol, inhaler, nebulizer, vaporizer and the like.

The pharmaceutical combination composition according to the present invention may be in the form of suppositories such as for example rectal or vaginal suppositories.

In a preferred embodiment of the present invention, the pharmaceutical composition is in form of an oral dosage form, preferably a solid oral dosage form.

In one aspect, the present invention is also directed to a method for maintaining or improving the functional and morphological properties of the arterial wall, preventing, reducing or reversing arterial aging, and/or decreasing the worsening or the occurrence of cardiovascular disorders, in an unhealthy subject, comprising administering to said subject a pharmaceutical composition according to the present invention.

In another aspect, the present invention is also directed to a method for maintaining or improving the functional and morphological properties of the arterial wall, preventing, reducing or reversing arterial aging, and/or decreasing the worsening or the occurrence of cardiovascular disorders, in a subject having at least one cardiovascular disorder, comprising administering to said subject a pharmaceutical composition according to the present invention.

In yet another aspect, the present invention is also directed to a method for maintaining or improving the functional and morphological properties of the arterial wall, preventing, reducing or reversing arterial aging, and/or decreasing the worsening or the occurrence of cardiovascular disorders, in a subject having at least one risk factor for a cardiovascular disorder, comprising administering to said subject a pharmaceutical composition according to the present invention.

In one aspect, the present invention is also directed to the use of a pharmaceutical composition according to the present invention for the manufacture of a medicament for maintaining or improving the functional and morphological properties of the arterial wall, preventing, reducing or reversing arterial aging, and/or decreasing the worsening or the occurrence of cardiovascular disorders in an unhealthy subject.

In another aspect, the present invention is also directed to the use of a pharmaceutical composition according to the present invention for the manufacture of a medicament for maintaining or improving the functional and morphological properties of the arterial wall, preventing, reducing or reversing arterial aging, and/or decreasing the worsening or the occurrence of cardiovascular disorders in a subject having at least one cardiovascular disorder.

In yet another aspect, the present invention is also directed to the use of a pharmaceutical composition according to the present invention for the manufacture of a medicament for maintaining or improving the functional and morphological properties of the arterial wall, preventing, reducing or reversing arterial aging, and/or decreasing the worsening or the occurrence of cardiovascular disorders in a subject having at least one risk factor for a cardiovascular disorder.

When administering the pharmaceutical composition according to the present invention the significant and unexpected improvements in functional and morphological properties of arterial wall and consequently reduction and reversal of arterial age and decreasing worsening or occurrence of cardiovascular disorders are observed. The improvement is particularly astonishing in view of the teaching of the co-pending patent applications disclosing the use of pharmaceutical composition comprising at least one renin-angiotensin-aldosterone system inhibitor in a subtherapeutic daily dose and at least one HMG-CoA reductase inhibitor in a subtherapeutic daily dose in apparently healthy subjects who do not have manifested cardiovascular disorders and who do not have disorders which importantly influence the functional capacity of different tissues/organs or the whole body.

Furthermore, by using age-related normogram obtained on large sample of apparently healthy subjects the estimation of "biological" arterial age can be determined. The inventors of the present application surprisingly found out the significant and unexpected decrease of "biological" arterial age.

The above mentioned advantages of the present invention were determined in double-blind studies wherein patients with diabetes mellitus type I and type II, arterial hypertension, hypercholesterolemia, post-myocardial infarction and participants having smoking and obesity as risk factor for developing cardiovascular disorders were assigned to treatment (fluvastatin sodium 10 mg/valsartan 20 mg daily, 1 month—30 days). The main functional and morphological characteristics of arterial wall were tested by measurement of flow-mediated dilatation of brachial artery (FMD), pulse-wave velocity (PWV) and β-stiffness of carotid artery once at baseline and after 30 days. All parameters of arterial function were significantly improved after 30 days of treatment. Said beneficial arterial characteristics were not accompanied by any changes in lipids or blood pressure. Moreover, the arterial age calculated by age-related normogram substantially decreased.

To conclude, the inventors of the present application surprisingly found out that functional and morphological characteristics of arterial wall that can be measured by standard and widely used methods can be substantially improved by administering the pharmaceutical combination composition according to the present invention. The achieved beneficial arterial characteristics were not accompanied by the primary action of renin-angiotensin-aldosterone system inhibitors or HMG CoA reductase inhibitors i.e. reduction of lipids and blood pressure. Unexpectedly, the improvement in age-related characteristics in the observed subjects was achieved already after short-term treatment (for example at least one month) and again, unexpectedly, persists at substantial level approximately from about 3 to about 12 months or from about 6 to about 12 months after discontinuation of treatment. The pharmaceutical composition according to the present invention reveals several synergistic effects in comparison with both classes of drugs alone. The unique efficacy profile of said composition allows a cyclic treatment consisting of a short term treatment-period followed by a long term rest-period during which beneficial arterial characteristics are still present.

The present invention further comprises the following preferred embodiments:

1. A pharmaceutical combination composition comprising at least one renin-angiotensin-aldosterone system inhibitor selected from the group consisting of renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose for use in improving functional and morphological properties of arterial wall in a subject having at least one cardiovascular disorder or having at least one risk factor for cardiovascular disorder.

2. A pharmaceutical combination composition comprising at least one renin-angiotensin-aldosterone system inhibitor selected from the group consisting of renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose for use in reduction and reversal of arterial age in a subject having at least one cardiovascular disorder or having at least one risk factor for cardiovascular disorder.

3. A pharmaceutical combination composition comprising at least one renin-angiotensin-aldosterone system inhibitor selected from the group consisting of renin inhibitor, angiotensin-converting enzyme inhibitor and angiotensin II receptor antagonist and any combinations thereof in a subtherapeutic daily dose and at least one HMG-CoA reductase inhibitor in a subtherapeutic daily dose for use in decreasing worsening or occurrence of cardiovascular disorders in a subject having at least one cardiovascular disorder or having at least one risk factor for cardiovascular disorder.

4. The pharmaceutical combination composition according to items 1 to 3 wherein the subtherapeutic daily dose is between 1 and 50%, preferably between 1 and 25% of daily recommended therapeutic dose.

5. The pharmaceutical combination composition according to anyone of items 1 to 4 wherein cardiovascular disorder is selected from the group consisting of:
  a) cardiovascular disorder selected from the group consisting of ischemic heart disease, carotid and intracerebral artery disease, peripheral arterial disease, aortic aneurism, and any combinations thereof, preferably myocardial infarction, stroke, dementia, critical limb ischemia, aortic aneurism and any combinations thereof, more preferably myocardial infarction, stroke, vascular dementia and any combinations thereof or
  b) disorder which has high rate of cardiovascular disorder occurrence selected from the group consisting of, but not limited to, diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably diabetes, metabolic syndrome, arterial hypertension, hypercholesterolemia, and any combinations thereof, or
  c) risky life style which has high rate of cardiovascular occurrence selected from the group consisting of, but not limited to, smoking, obesity, physical inactivity, continuous stress, and any combinations thereof, preferably smoking, obesity, physical inactivity, continuous stress, and any combinations thereof, more preferably smoking, obesity, and any combinations thereof.

6. The pharmaceutical combination composition according to anyone of items 1 to 5 wherein renin-angiotensin-aldosterone system inhibitor is angiotensin II receptor antagonist, selected from the group consisting of, azilsartan, losartan, eprosartan, irbesartan, olmesartan, candesartan, valsartan and telmisartan and any pharmaceutically acceptable salts or esters thereof, preferably azilsartan, losartan, telmisartan, olmesartan, candesartan and valsartan and any pharmaceutically acceptable salts or esters thereof, more preferably losartan, telmisartan, azilsartan, candesartan and valsartan and any pharmaceutically acceptable salts or esters thereof and even more preferably valsartan and telmisartan and any pharmaceutically acceptable salts or esters thereof.

7. The pharmaceutical combination composition according to item 6 wherein angiotensin II receptor antagonist is valsartan or any pharmaceutically acceptable salts.

8. The pharmaceutical combination composition according to anyone of items 1 to 7 wherein HMG-CoA reductase inhibitor is selected from the group consisting of mevastatin, pitavastatin, lovastatin, simvastatin, pravastatin, fluvastatin, atorvastatin, cerivastatin, and rosuvastatin and any pharmaceutically acceptable salts or esters thereof, preferably simvastatin, fluvastatin, atorvastatin and rosuvastatin and any pharmaceutically acceptable salts or esters thereof, more preferably fluvastatin, atorvastatin and rosuvastatin and any pharmaceutically acceptable salts or esters thereof and even more preferably fluvastatin and atorvastatin and any pharmaceutically acceptable salts or esters thereof.

9. The pharmaceutical combination composition according to item 8 wherein HMG-CoA reductase inhibitor is fluvastatin sodium.

10. The pharmaceutical combination composition according to anyone of items 1 to 9 wherein one intervention-cycle consists of one treatment-period lasting between about 1 month to about 9 months, preferably between about 1 month to about 9 months and one rest-period lasting 12 months, preferably between 1 and 12 months or between 1 and 6 months or between 1 and 3 months.

11. The pharmaceutical combination composition comprising valsartan or any pharmaceutically acceptable salts thereof in a daily dose between 1 and 40 mg and fluvastatin or any pharmaceutically acceptable salts thereof in a daily dose between 1 and 10 mg for use in improving functional and morphological properties of arterial wall in a subject having at least one cardiovascular disorder or having at least one risk factor for cardiovascular disorder.

12. The pharmaceutical combination composition comprising valsartan or any pharmaceutically acceptable salts thereof in a daily dose between 1 and 40 mg and fluvastatin or any pharmaceutically acceptable salts thereof in a daily dose between 1 and 10 mg for use in reduction and reversal of arterial age in a subject having at least one cardiovascular disorder or having at least one risk factor for cardiovascular disorder.

13. The pharmaceutical combination composition comprising valsartan or any pharmaceutically acceptable salts thereof in a daily dose between 1 and 40 mg and fluvastatin or any pharmaceutically acceptable salts thereof in a daily dose between 1 and 10 mg for use in decreasing worsening or occurrence of cardiovascular disorders in a subject having at least one cardiovascular disorder or having at least one risk factor for cardiovascular disorder.

14. The pharmaceutical combination composition according to any one of items 1 to 13 further comprising one or more pharmaceutically acceptable excipient.

Still further, the present invention comprises the following items:

1. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in maintaining or improving the functional and morphological properties of the arterial wall in unhealthy subjects.

2. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in the prevention, reduction or reversal of arterial aging in unhealthy subjects.

3. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in decreasing the worsening or the occurrence of cardiovascular disorders in unhealthy subjects.

4. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in maintaining or improving the functional and morphological properties of the arterial wall in subjects having at least one cardiovascular disorder.

5. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in the prevention, reduction or reversal of arterial aging in subjects having at least one cardiovascular disorder.

6. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in decreasing the worsening or the occurrence of cardiovascular disorders in subjects having at least one cardiovascular disorder.

7. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in maintaining or improving the functional and morphological properties of the arterial wall in subjects having at least one risk factor for a cardiovascular disorder.

8. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in the prevention, reduction or reversal of arterial aging in subjects having at least one risk factor for a cardiovascular disorder.

9. A pharmaceutical composition comprising
   at least one renin-angiotensin-aldosterone system inhibitor in a subtherapeutic daily dose, and
   at least one HMG-CoA reductase inhibitor in a subtherapeutic daily dose, for use in decreasing the worsening or the occurrence of cardiovascular disorders in subjects having at least one risk factor for a cardiovascular disorder.

10. The pharmaceutical composition according to any one of items 1 to 3, wherein the unhealthy subjects have a risk for a coronary heart disease (10-year risk) according to the Framingham Risk Score of more than 10%, preferably more than 12%, more preferably more than 15%, most preferably more than 20%.

11. The pharmaceutical composition according to any one of items 4 to 6, wherein the cardiovascular disorder is selected from the group consisting of ischemic heart disease, carotid and intracerebral artery disease, peripheral arterial disease, aortic aneurism, and any combinations thereof.

12. The pharmaceutical composition according to any one of items 4 to 6, wherein the cardiovascular disorder is selected from the group consisting of myocardial infarction, stroke, dementia, critical limb ischemia, aortic aneurism, and any combinations thereof, preferably myocardial infarction, stroke, vascular dementia, and any combinations thereof, more preferably post-myocardial infarction.

13. The pharmaceutical composition according to any one of items 7 to 9, wherein the risk factor for a cardiovascular disorder is a disorder selected form the group consisting of diabetes, metabolic syndrome, hypercholesterolemia, hypertension, chronic inflammatory disorder, psoriasis, and any combinations thereof, preferably diabetes, metabolic syndrome, hypercholesterolemia, hypertension, and any combinations thereof, more preferably, diabetes, metabolic syndrome, arterial hypertension, hypercholesterolemia, and any combinations thereof, still more preferably diabetes mellitus type 1, diabetes mellitus type 2, arterial hypertension or hypercholesterolemia, and any combinations thereof, most preferably diabetes mellitus type 1 or diabetes mellitus type 2.

14. The pharmaceutical composition according to any one of items 7 to 9, wherein the risk factor for a cardiovascular disorder is a risky life style selected from the group consisting of smoking, obesity, physical inactivity, continuous stress, and any combinations thereof, preferably smoking, obesity, physical inactivity, continuous stress, and any combinations thereof, more preferably smoking, obesity, and any combinations thereof, most preferably smoking or obesity.

15. The pharmaceutical composition according to any one of items 1 to 14, wherein the renin-angiotensin-aldosterone inhibitor is selected from the group consisting of renin inhibitor, angiotensin converting enzyme inhibitor, angiotensin II receptor antagonist and combinations thereof.

16. The pharmaceutical composition according to any one of items 1 to 15, wherein the renin-angiotensin-aldosterone system inhibitor is an angiotensin II receptor antagonist.

17. The pharmaceutical composition according to any one of items 1 to 16, wherein the angiotensin II receptor antagonist is selected from the group consisting of azilsartan, losartan, eprosartan, irbesartan, olmesartan, candesartan, valsartan, telmisartan, and any pharmaceutically acceptable salts or esters and any combinations thereof.

18. The pharmaceutical composition according to any one of items 1 to 17, wherein the angiotensin II receptor antagonist is selected from the group consisting of azilsartan, losartan, olmesartan, irbesartan, candesartan, valsartan, telmisartan, and any pharmaceutically acceptable salts or esters, and combinations thereof.

19. The pharmaceutical composition according to any one of items 1 to 18, wherein the angiotensin II receptor antagonist is selected from the group consisting of candesartan, valsartan, telmisartan, irbesartan, olmesartan and any pharmaceutically acceptable salts or esters, and combinations thereof.

20. The pharmaceutical composition according to any one of items 1 to 19, wherein the angiotensin II receptor antagonist is selected from the group consisting of valsartan, telmisartan, irbesartan, olmesartan and any pharmaceutically acceptable salts or esters, and combinations thereof.

21. The pharmaceutical composition according to any one of items 1 to 20, wherein the angiotensin II receptor antagonist is selected from the group consisting of valsartan, telmisartan and any pharmaceutically acceptable salts or esters, and combinations thereof.

22. The pharmaceutical composition according to any one of items 1 to 21, wherein the angiotensin II receptor antagonist is valsartan or any pharmaceutically acceptable salt thereof, preferably valsartan.

23. The pharmaceutical composition according to any one of items 1 to 21, wherein the angiotensin II receptor antagonist is telmisartan or any pharmaceutically acceptable salt thereof.

24. The pharmaceutical composition according to any one of items 1 to 23, wherein the HMG-CoA reductase inhibitor is selected from the group consisting of mevastatin, pitavastatin, lovastatin, simvastatin, pravastatin, fluvastatin, atorvastatin, cerivastatin, rosuvastatin, and any pharmaceutically acceptable salts or esters, and combinations thereof.

25. The pharmaceutical composition according to any one of items 1 to 24, wherein the HMG-CoA reductase inhibitor is selected from the group consisting of simvastatin, fluvastatin, atorvastatin, rosuvastatin, and any pharmaceutically acceptable salts or esters, and combinations thereof.

26. The pharmaceutical composition according to any one of items 1 to 25, wherein the HMG-CoA reductase inhibitor is selected from the group consisting of fluvastatin, atorvastatin, rosuvastatin, and any pharmaceutically acceptable salts or esters, and combinations thereof.

27. The pharmaceutical composition according to any one of items 1 to 26, wherein the HMG-CoA reductase inhibitor is selected from the group consisting of fluvastatin, rosuvastatin, atorvastatin, and any pharmaceutically acceptable salts or esters, and combinations thereof.

28. The pharmaceutical composition according to any one of items 1 to 27, wherein the HMG-CoA reductase inhibitor is fluvastatin or any pharmaceutically acceptable salt thereof, and preferably is fluvastatin sodium.

29. The pharmaceutical composition according to any one of items 1 to 27, wherein the HMG-CoA reductase inhibitor is atorvastatin or any pharmaceutically acceptable salt thereof, and preferably is atorvastatin calcium.

30. The pharmaceutical composition according to any one of items 1 to 29, wherein the renin-angiotensin-aldosterone system inhibitor is an angiotensin II receptor antagonist selected from the group consisting of valsartan, telmisartan and any pharmaceutically acceptable salts or esters thereof, and the HMG-CoA reductase inhibitor is selected from the group consisting of fluvastatin and atorvastatin and any pharmaceutically acceptable salts or esters thereof.

31. The pharmaceutical composition according to any one of items 1 to 30, wherein angiotensin II receptor antagonist and HMG-CoA reductase inhibitor are present in the composition in a weight ratio of from 20:1 to 1:20, preferably in a weight ratio of from 10:1 to 1:10, more preferably in a weight ratio of from 5:1 to 1:5.

32. The pharmaceutical composition according to any one of items 1 to 31, wherein the renin-angiotensin-aldosterone system inhibitor is valsartan or a pharmaceutically acceptable salt or ester thereof and the HMG-CoA reductase inhibitor is fluvastatin or a pharmaceutically acceptable salt or ester thereof.

33. The pharmaceutical composition according to any one of items 1 to 32 wherein the renin-angiotensin-aldosterone system inhibitor is valsartan and the HMG-CoA reductase inhibitor is fluvastatin sodium.

34. The pharmaceutical composition according to any one of items 1 to 33, wherein valsartan and fluvastatin sodium are present in the composition in a weight ratio of from 9:1 to 1:9, preferably in a weight ratio of from 5:1 to 1:1, more preferably in a weight ratio of from 3:1 to 1:1, still more preferably in a weight ratio of from 2.5:1 to 1.6:1, most preferably in a weight ratio of 2:1.

35. The pharmaceutical composition according to any one of items 1 to 33, wherein valsartan and fluvastatin sodium are present in the composition in a weight ratio of from 9:1 to 1:9, preferably in a weight ratio of from 1:1 to 1:5, more preferably in a weight ratio of from 1:1 to 1:3, still more preferably in a weight ratio of from 1:1.6 to 1:2.5, most preferably in a weight ratio of 1:2.

36. The pharmaceutical composition according to any one of items 1 to 31, wherein the renin-angiotensin-aldosterone system inhibitor is valsartan or a pharmaceutically acceptable salt or ester thereof and the HMG-CoA reductase inhibitor is atorvastatin or a pharmaceutically acceptable salt or ester thereof.

37. The pharmaceutical composition according to any one of items 1 to 31, wherein the renin-angiotensin-aldosterone system inhibitor is valsartan or a pharmaceutically acceptable salt or ester thereof and the HMG-CoA reductase inhibitor is atorvastatin or a pharmaceutically acceptable salt or ester thereof.

38. The pharmaceutical composition according to any one of items 1 to 31, or 36-37, wherein the renin-angiotensin-aldosterone system inhibitor is valsartan and the HMG-CoA reductase inhibitor is atorvastatin calcium.

39. The pharmaceutical composition according to any one of items 1 to 31, 36 to 38, wherein valsartan and atorvastatin calcium are present in the composition in a weight ratio of from 9:1 to 1:9, preferably in a weight ratio of from 5:1 to 1:1, more preferably in a weight ratio of from 3.5:1 to 1.5:1, still more preferably in a weight ratio of from 3:1 to 2:1, most preferably in a weight ratio of 2.5:1.

40. The pharmaceutical composition according to any one of items 1 to 31, 36 to 38, wherein valsartan and atorvastatin calcium are present in the composition in a weight ratio of from 20:1 to 1:1, preferably in a weight ratio of from 12:1 to 5:1, more preferably in a weight ratio of from 10:1 to 6:1, still more preferably in a weight ratio of from 9:1 to 7:1, most preferably in a weight ratio of 8:1.

41. The pharmaceutical composition according to any one of items 1 to 40, wherein the subtherapeutic daily dose of the HMG-CoA reductase inhibitor does not substantially change the cholesterol level.

42. The pharmaceutical composition according to any one of items 1 to 41, wherein the subtherapeutic daily dose of the renin-angiotensin-aldosterone system inhibitor does not substantially change the systolic blood pressure.

43. The pharmaceutical composition according to any one of items 1 to 42, wherein the subtherapeutic daily dose of the renin-angiotensin-aldosterone system inhibitor does not substantially change the diastolic blood pressure.

44. The pharmaceutical composition according to any one of items 1 to 43, wherein the subtherapeutic daily dose of the HMG-CoA reductase inhibitor does not change the LDL cholesterol level in a subject by more than 15%, preferably more than 10%, more preferably more than 8%.

45. The pharmaceutical composition according to any one of items 1 to 44, wherein the subtherapeutic daily dose of the HMG-CoA reductase inhibitor does not change the LDL cholesterol level in a subject by more than 15%, preferably more than 10%, more preferably more than 8%, when administered for at least 10 days, preferably at least 14 days, more preferably at least 1 month.

46. The pharmaceutical composition according to any one of items 1 to 45, wherein the subtherapeutic daily dose of the HMG-CoA reductase inhibitor does not decrease the HDL cholesterol level in a subject by more than 15%, preferably more than 12%, and more preferably more than 10%.

47. The pharmaceutical composition according to any one of items 1 to 46, wherein the subtherapeutic daily dose of the HMG-CoA reductase inhibitor does not decrease the HDL cholesterol level in a subject by more than 15%, preferably more than 12%, and more preferably more than 10%, when administered for at least 10 days, preferably at least 14 days, more preferably at least 1 month.

48. The pharmaceutical composition according to any one of items 1 to 47, wherein the subtherapeutic daily dose of the renin-angiotensin-aldosterone system inhibitor does not change the systolic blood pressure in a subject by more than 10%, preferably more than 8%, more preferably more than 6%, most preferably more than 4%.

49. The pharmaceutical composition according to any one of items 1 to 48, wherein the subtherapeutic daily dose of the renin-angiotensin-aldosterone system inhibitor does not change the systolic blood pressure in a subject by more than 10%, preferably more than 8%, more preferably more than 6%, most preferably more than 4%, when administered for at least 10 days, preferably at least 14 days, more preferably at least 1 month.

50. The pharmaceutical composition according to any one of items 1 to 49, wherein the subtherapeutic daily dose of the renin-angiotensin-aldosterone system inhibitor does not change the diastolic blood pressure in a subject by more than 10%, preferably more than 8%, more preferably more than 6%, most preferably more than 5%.

51. The pharmaceutical composition according to any one of items 1 to 50, wherein the subtherapeutic daily dose of the renin-angiotensin-aldosterone system inhibitor does not change the diastolic blood pressure in a subject by more than 10%, preferably more than 8%, more preferably more than 6%, most preferably more than 5%, when administered for at least 10 days, preferably at least 14 days, more preferably at least 1 month.

52. The pharmaceutical composition according to any one of items 1 to 51, wherein the subtherapeutic daily dose of the renin-angiotensin-aldosterone system inhibitor and the subtherapeutic daily dose of the HMG-CoA reductase inhibitor together do not change the LDL cholesterol level by more than 15%, preferably more than 10%, more preferably more than 8%.

53. The pharmaceutical composition according to any one of items 1 to 52, wherein the subtherapeutic daily dose of the renin-angiotensin-aldosterone system inhibitor and the subtherapeutic daily dose of the HMG-CoA reductase inhibitor together do not change the LDL cholesterol level by more than 15%, preferably more than 10%, more preferably more than 8%, when administered for at least 10 days, preferably at least 14 days, more preferably at least 1 month.

54. The pharmaceutical composition according to any one of items 1 to 53, wherein the subtherapeutic daily dose of the renin-angiotensin-aldosterone system inhibitor and the subtherapeutic daily dose of the HMG-CoA reductase inhibitor together do not decrease the HDL cholesterol level by more than 15%, preferably more than 12%, more preferably more than 10%.

55. The pharmaceutical composition according to any one of items 1 to 54, wherein the subtherapeutic daily dose of the renin-angiotensin-aldosterone system inhibitor and the subtherapeutic daily dose of the HMG-CoA reductase inhibitor together do not decrease the HDL cholesterol level by more than 15%, preferably more than 12%, more preferably more than 10%, when administered for at least 10 days, preferably at least 14 days, more preferably at least 1 month.

56. The pharmaceutical composition according to any one of items 1 to 55, wherein the subtherapeutic daily dose of the renin-angiotensin-aldosterone system inhibitor and the subtherapeutic daily dose of the HMG-CoA reductase inhibitor together do not change the systolic blood pressure in a 57. The pharmaceutical composition according to any one of items 1 to 56, wherein the subtherapeutic daily dose of the renin-angiotensin-aldosterone system inhibitor and the subtherapeutic daily dose of the HMG-CoA reductase inhibitor together do not change the systolic blood pressure in a subject by more than 10%, preferably more than 8%, more preferably more than 6%, most preferably more than 4%, when administered for at least 10 days, preferably at least 14 days, more preferably at least 1 month.

58. The pharmaceutical composition according to any one of items 1 to 57, wherein the subtherapeutic daily dose of the renin-angiotensin-aldosterone system inhibitor and the subtherapeutic daily dose of the HMG-CoA reductase inhibitor together do not change the diastolic blood pressure in a subject by more than 10%, preferably more than 8%, more preferably more than 68%, most preferably more than 5%.

59. The pharmaceutical composition according to any one of items 1 to 58, wherein the subtherapeutic daily dose of the renin-angiotensin-aldosterone system inhibitor and the subtherapeutic daily dose of the HMG-CoA reductase inhibitor together do not change the diastolic blood pressure in a subject by more than 10%, preferably more than 8%, more preferably more than 6%, most preferably more than 5%, when administered for at least 10 days, preferably at least 14 days, more preferably at least 1 month.

60. The pharmaceutical composition according to any one of items 1 to 59, wherein the subtherapeutic daily dose of the renin-angiotensin-aldosterone inhibitor is between 1 and 50%, preferably between 1 and 25% of the daily recommended therapeutic dose.

61. The pharmaceutical composition according to any one of items 1 to 60, wherein the subtherapeutic daily dose of the renin-angiotensin-aldosterone inhibitor is between 1 and 75 mg, between 1 and 60 mg, between 1 and 50 mg, between 1 and 45 mg, between 1 and 40 mg, and/or between 1 and 25 mg.

62. The pharmaceutical composition according to any one of items 1 to 61, wherein the renin-angiotensin-aldosterone is valsartan or any pharmaceutically acceptable salts or esters thereof, and the subtherapeutic daily dose is between 1 and 75 mg, preferably between 1 and 60 mg, more preferably between 1 and 50 mg, still more preferably between 1 to 40 mg, most preferably between 10 to 30 mg, particularly preferably 20 mg.

63. The pharmaceutical composition according to any one of items 1 to 62, wherein the renin-angiotensin-aldosterone is valsartan or any pharmaceutically acceptable salts or esters thereof, and the subtherapeutical dose thereof is between 1 to 40 mg, preferably between 1 to 30 mg, most preferably 20 mg.

64. The pharmaceutical composition according to any one of items 1 to 63, wherein the subtherapeutic daily dose of the HMG-CoA reductase inhibitor is between 1 to 40 mg, preferably between 1 to 30 mg, more preferably between 1 and 25 mg, still more preferably between 1 and 20 mg, most preferably between 1 and 15 mg, particularly preferably between 1 and 12 mg.

65. The pharmaceutical composition according to any one of items 1 to 64, wherein the HMG-CoA reductase inhibitor is fluvastatin or any pharmaceutically acceptable salts or esters thereof, and the subtherapeutical dose thereof is between 1 to 20 mg, preferably between 1 to 10 mg, most preferably 10 mg.

66. The pharmaceutical composition according to any one of items 1 to 64, wherein the HMG-CoA reductase inhibitor is atorvastatin or any pharmaceutically acceptable salts or esters thereof, and the subtherapeutical dose thereof is between 1 to 10 mg, preferably between 1 to 5 mg, most preferably 5 mg.

67. The pharmaceutical composition according to any one of items 1 to 66, wherein the subjects are human subjects.

68. The pharmaceutical composition according to any one of items 1 to 67, wherein
maintaining or improving the functional and morphological properties of the arterial wall,
the prevention, reduction or reversal of arterial aging, and/or
decreasing the worsening or the occurrence of cardiovascular disorders, is achieved after treatment period for at least 1 week, preferably for at least 10 days, preferably for at least 2 weeks, more preferably for at least 1 month.

69. The pharmaceutical composition according to any one of items 1 to 68, wherein the flow-mediated dilatation of brachial artery (FMD) after a period of treatment, preferably after 1 month of treatment, is increased compared to the beginning of the treatment.

70. The pharmaceutical composition according to any one of items 1 to 69, wherein the pulse-wave velocity (PWV) after a period of treatment, preferably after 1 month of treatment, is decreased compared to the beginning of the treatment.

71. The pharmaceutical composition according to any one of items 1 to 70, wherein the β-stiffness of carotid artery after a period of treatment, preferably after 1 month of treatment, is decreased compared to the beginning of the treatment.

72. The pharmaceutical composition according to any one of items 1 to 71, wherein the pulse-wave velocity (PWV) and the β-stiffness of carotid artery after 1 month of treatment are decreased compared to the beginning of the treatment.

73. The pharmaceutical composition according to any one of items 1 to 72, wherein the FMD increases by at least 20%, preferably at least 35%, more preferably at least 50%, most preferably at least 60% after a treatment period, preferably 1 month of treatment.

74. The pharmaceutical composition according to any one of items 1 to 73, wherein the FMD
in a subject having a risk for a coronary heart disease (10-year risk) according to the Framingham Risk score of more than 10%, preferably from 10 to 20%, more preferably from 14 to 18%,
increases by at least 60%, preferably at least 100%, more preferably at least 120%, most preferably at least 135% after a treatment period, preferably 1 month of treatment.

75. The pharmaceutical composition according to any one of items 1 to 73, wherein the FMD
in a subject having a risk for a coronary heart disease (10-year risk) according to the Framingham Risk score of more than 20%, preferably from 20 to 30%, more preferably from 25 to 29%,
increases by at least 60%, preferably at least 90%, more preferably at least 110%, most preferably at least 120% after a treatment period, preferably 1 month of treatment.

76. The pharmaceutical composition according to any one of items 1 to 73, wherein the FMD in a subject having at least one cardiovascular disorder,
wherein the cardiovascular disorder is preferably post-myocardial infarction, increases by at least 30%, preferably at least 45%, more preferably at least 60%, most preferably at least 65% after a treatment period, preferably 1 month of treatment.

77. The pharmaceutical composition according to any one of items 1 to 73, wherein the FMD in a subject having at least one risk factor for a cardiovascular disorder,
  wherein the risk factor is a disorder preferably selected from the group consisting of diabetes mellitus type 1, diabetes mellitus type 2, arterial hypertension, hypercholesterolemia and any combinations thereof,
  increases by at least 20%, preferably at least 35%, more preferably at least 50%, most preferably at least 60% after a treatment period, preferably 1 month of treatment.

78. The pharmaceutical composition according to any one of items 1 to 73, or 77, wherein the FMD in a subject having diabetes mellitus type 1 increases by at least 40%, preferably at least 60%, more preferably at least 70%, most preferably at least 75% after a treatment period, preferably 1 month of treatment.

79. The pharmaceutical composition according to any one of items 1 to 73, or 77, wherein the FMD in a subject having diabetes mellitus type 2 increases by at least 40%, preferably at least 55%, more preferably at least 65%, most preferably at least 70% after a treatment period, preferably 1 month of treatment.

80. The pharmaceutical composition according to any one of items 1 to 73, wherein the FMD in a subject having at least one risk factor for a cardiovascular disorder,
  wherein the risk factor is a risky life style preferably selected from the group consisting of smoking, obesity and a combination thereof,
  increases by at least 100%, preferably at least 120%, more preferably at least 140%, most preferably at least 150% after a treatment period, preferably 1 month of treatment.

81. The pharmaceutical composition according to any one of items 1 to 80, wherein the PWV decreases by at least 2%, preferably at least 3%, more preferably at least 4%, most preferably at least 4.5% after a treatment period, preferably 1 month of treatment.

82. The pharmaceutical composition according to any one of items 1 to 81, wherein the PWV
  in a subject having a risk for a coronary heart disease (10-year risk) according to the Framingham Risk score of more than 10%, preferably from 10 to 20%, more preferably from 14 to 18%,
  decreases by at least 2%, preferably at least 3%, more preferably at least 4%, most preferably at least 4.2% after a treatment period, preferably 1 month of treatment.

83. The pharmaceutical composition according to any one of items 1 to 81, wherein the PWV
  in a subject having a risk for a coronary heart disease (10-year risk) according to the Framingham Risk score of more than 20%, preferably from 20 to 30%, more preferably from 25 to 29%,
  decreases by at least 2%, preferably at least 3%, more preferably at least 3.5%, most preferably at least 4% after a treatment period, preferably 1 month of treatment.

84. The pharmaceutical composition according to any one of items 1 to 81, wherein the PWV in a subject having at least one cardiovascular disorder,
  wherein the cardiovascular disorder is preferably post-myocardial infarction,
  decreases by at least 3%, preferably at least 5%, more preferably at least 6%, most preferably at least 7% after a treatment period, preferably 1 month of treatment.

85. The pharmaceutical composition according to any one of items 1 to 81, wherein the PWV in a subject having at least one risk factor for a cardiovascular disorder,
  wherein the risk factor is a disorder preferably selected from the group consisting of diabetes mellitus type 1, diabetes mellitus type 2, arterial hypertension, hypercholesterolemia, and any combinations thereof,
  decreases by at least 2%, preferably at least 3%, more preferably at least 4%, most preferably at least 4.2% after a treatment period, preferably 1 month of treatment.

86. The pharmaceutical composition according to any one of items 1 to 81, or 85, wherein the PWV in a subject having diabetes mellitus type 1 decreases by at least 3%, preferably at least 5%, more preferably at least 6%, most preferably at least 7% after a treatment period, preferably 1 month of treatment.

87. The pharmaceutical composition according to any one of items 1 to 81, or 85, wherein the PWV in a subject having diabetes mellitus type 2 decreases by at least 4%, preferably at least 6%, more preferably at least 8%, most preferably at least 8.2% after a treatment period, preferably 1 month of treatment.

88. The pharmaceutical composition according to any one of items 1 to 81, wherein the PWV in a subject having at least one risk factor for a cardiovascular disorder,
  wherein the risk factor is a risky life style preferably selected from the group consisting of smoking, obesity and a combination thereof,
  decreases by at least 2%, preferably at least 4%, more preferably at least 5%, most preferably at least 6% after a treatment period, preferably 1 month of treatment.

89. The pharmaceutical composition according to any one of items 1 to 88, wherein the β-stiffness decreases by at least 2%, preferably at least 4%, more preferably at least 6%, most preferably at least 7.2% after a treatment period, preferably 1 month of treatment.

90. The pharmaceutical composition according to any one of items 1 to 89, wherein the β-stiffness
  in a subject having a risk for a coronary heart disease (10-year risk) according to the Framingham Risk score of more than 10%, preferably from 10 to 20%, more preferably from 14 to 18%,
  decreases by at least 3%, preferably at least 5%, more preferably at least 6%, most preferably at least 6.5% after a treatment period, preferably 1 month of treatment.

91. The pharmaceutical composition according to any one of items 1 to 89, wherein the β-stiffness
  in a subject having a risk for a coronary heart disease (10-year risk) according to the Framingham Risk score of more than 20%, preferably from 20 to 30%, more preferably from 25 to 29%,
  decreases by at least 2%, preferably at least 3%, more preferably at least 3.5%, most preferably at least 4% after a treatment period, preferably 1 month of treatment.

92. The pharmaceutical composition according to any one of items 1 to 89, wherein the β-stiffness in a subject having at least one cardiovascular disorder,
  wherein the cardiovascular disorder is preferably post-myocardial infarction, decreases by at least 3%, preferably at least 5%, more preferably at least 6%, most preferably at least 6.5% after a treatment period, preferably 1 month of treatment.

93. The pharmaceutical composition according to any one of items 1 to 89, wherein the β-stiffness in a subject having at least one risk factor for a cardiovascular disorder,
wherein the risk factor is a disorder preferably selected from the group consisting of diabetes mellitus type 1, diabetes mellitus type 2, arterial hypertension or hypercholesterolemia,
decreases by at least 2%, preferably at least 4%, more preferably at least 6%, most preferably at least 7% after a treatment period, preferably 1 month of treatment.

94. The pharmaceutical composition according to any one of items 1 to 89, or 93, wherein the β-stiffness in a subject having diabetes mellitus type 1 decreases by at least 4%, preferably at least 6%, more preferably at least 8%, most preferably at least 10% after a treatment period, preferably 1 month of treatment.

95. The pharmaceutical composition according to any one of items 1 to 89, or 93, wherein the β-stiffness in a subject having diabetes mellitus type 2 decreases by at least 3%, preferably at least 5%, more preferably at least 6%, most preferably at least 7% after a treatment period, preferably 1 month of treatment.

96. The pharmaceutical composition according to any one of items 1 to 89, wherein the β-stiffness in a subject having at least one risk factor for a cardiovascular disorder,
wherein the risk factor is a risky life style preferably selected from the group consisting of smoking, obesity and a combination thereof,
decreases by at least 2%, preferably at least 4%, more preferably at least 6%, most preferably at least 8% after a treatment period, preferably 1 month of treatment.

97. The pharmaceutical composition according to any one of items 1 to 96, wherein after discontinuation of the treatment for at least 3 months, preferably at least 6 months, the residual improvement of the FMD is at least 20%, preferably at least 30%, more preferably at least 40%, most preferably at least 50% based on the increase of the FMD after a period of treatment.

98. The pharmaceutical composition according to any one of items 1 to 97, wherein after discontinuation of the treatment for at least 3 months, preferably at least 6 months, the residual improvement of the FMD
in a subject having a risk for a coronary heart disease (10-year risk) according to the Framingham Risk score of more than 10%, preferably from 10 to 20%, more preferably from 14 to 18%,
is at least 45%, preferably at least 55%, more preferably at least 65%, most preferably at least 75% based on the increase of the FMD after a period of treatment.

99. The pharmaceutical composition according to any one of items 1 to 97, wherein after discontinuation of the treatment for at least 3 months, preferably at least 6 months, the residual improvement of the FMD
in a subject having a risk for a coronary heart disease (10-year risk) according to the Framingham Risk score of more than 20%, preferably from 20 to 30%, more preferably from 25 to 29%,
is at least 40%, preferably at least 50%, more preferably at least 60%, most preferably at least 70% based on the increase of the FMD after a period of treatment.

100. The pharmaceutical composition according to any one of items 1 to 97, wherein after discontinuation of the treatment for at least 3 months, preferably at least 6 months, the residual improvement of the FMD in a subject having at least one cardiovascular disorder,
wherein the cardiovascular disorder is preferably post-myocardial infarction,
is at least 50%, preferably at least 60%, more preferably at least 70%, most preferably at least 80% based on the increase of the FMD after a period of treatment.

101. The pharmaceutical composition according to any one of items 1 to 97, wherein after discontinuation of the treatment for at least 3 months, preferably at least 6 months, the residual improvement of the FMD in a subject having at least one risk factor for a cardiovascular disorder,
wherein the risk factor is a disorder preferably selected from the group consisting of diabetes mellitus type 1, diabetes mellitus type 2, arterial hypertension, hypercholesterolemia and any combinations thereof,
is at least 20%, preferably at least 30%, more preferably at least 40%, most preferably at least 50% based on the increase of the FMD after a period of treatment.

102. The pharmaceutical composition according to any one of items 1 to 97, or 101, wherein after discontinuation of the treatment for at least 3 months, preferably at least 6 months, the residual improvement of the FMD in a subject having diabetes mellitus type 1 is at least 30%, preferably at least 40%, more preferably at least 50%, most preferably at least 60% based on the increase of the FMD after a period of treatment.

103. The pharmaceutical composition according to any one of items 1 to 97, or 101, wherein after discontinuation of the treatment for at least 3 months, preferably at least 6 months, the residual improvement of the FMD in a subject having diabetes mellitus type 2 is at least 50%, preferably at least 60%, more preferably at least 70%, most preferably at least 80% based on the increase of the FMD after a period of treatment.

104. The pharmaceutical composition according to any one of items 1 to 97, Wherein after discontinuation of the treatment for at least 3 months, preferably at least 6 months, the residual improvement of the FMD in a subject having at least one risk factor for a cardiovascular disorder,
wherein the risk factor is a risky life style preferably selected from the group consisting of smoking, obesity and a combination thereof,
is at least 20%, preferably at least 30%, more preferably at least 40%, most preferably at least 50% based on the increase of the FMD after a period of treatment.

105. The pharmaceutical composition according to any one of items 1 to 104, wherein after discontinuation of the treatment for at least 3 months, preferably at least 6 months, the residual improvement of the PWV is at least 20%, preferably at least 30%, more preferably at least 40%, most preferably at least 50% based on the decrease of the PWV after a period of treatment.

106. The pharmaceutical composition according to any one of items 1 to 105, wherein after discontinuation of the treatment for at least 3 months, preferably at least 6 months, the residual improvement of the PWV
in a subject having a risk for a coronary heart disease (10-year risk) according to the Framingham Risk score of more than 10%, preferably from 10 to 20%, more preferably from 14 to 18%,
is at least 35%, preferably at least 45%, more preferably at least 55%, most preferably at least 65% based on the decrease of the PWV after a period of treatment.

107. The pharmaceutical composition according to any one of items 1 to 105, wherein after discontinuation of the treatment for at least 3 months, preferably at least 6 months, the residual improvement of the PWV
in a subject having a risk for a coronary heart disease (10-year risk) according to the Framingham Risk score of more than 20%, preferably from 20 to 30%, more preferably from 25 to 29%,
is at least 30%, preferably at least 40%, more preferably at least 50%, most preferably at least 60% based on the decrease of the PWV after a period of treatment.

108. The pharmaceutical composition according to any one of items 1 to 105, wherein after discontinuation of the treatment for at least 3 months, preferably at least 6 months, the residual improvement of the PWV in a subject having at least one cardiovascular disorder,
wherein the cardiovascular disorder is preferably post-myocardial infarction,
is at least 40%, preferably at least 50%, more preferably at least 60%, most preferably at least 70% based on the decrease of the PWV after a period of treatment.

109. The pharmaceutical composition according to any one of items 1 to 105, wherein after discontinuation of the treatment for at least 3 months, preferably at least 6 months, the residual improvement of the PWV in a subject having at least one risk factor for a cardiovascular disorder,
wherein the risk factor is a disorder preferably selected from the group consisting of diabetes mellitus type 1, diabetes mellitus type 2, arterial hypertension, hypercholesterolemia and any combinations thereof,
is at least 20%, preferably at least 30%, more preferably at least 40%, most preferably at least 50% based on the decrease of the PWV after a period of treatment.

110. The pharmaceutical composition according to any one of items 1 to 105, or 108, wherein after discontinuation of the treatment for at least 3 months, preferably at least 6 months, the residual improvement of the PWV in a subject having diabetes mellitus type 1 is at least 30%, preferably at least 40%, more preferably at least 50%, most preferably at least 60% based on the decrease of the PWV after a period of treatment.

111. The pharmaceutical composition according to any one of items 1 to 105, or 108, wherein after discontinuation of the treatment for at least 3 months, preferably at least 6 months, the residual improvement of the PWV in a subject having diabetes mellitus type 2 is at least 40%, preferably at least 50%, more preferably at least 60%, most preferably at least 70% based on the decrease of the PWV after a period of treatment.

112. The pharmaceutical composition according to any one of items 1 to 105, wherein after discontinuation of the treatment for at least 3 months, preferably at least 6 months, the residual improvement of the PWV in a subject having at least one risk factor for a cardiovascular disorder,
wherein the risk factor is a risky life style preferably selected from the group consisting of smoking, obesity and a combination thereof,
is at least 25%, preferably at least 35%, more preferably at least 45%, most preferably at least 55% based on the decrease of the PWV after a period of treatment.

113. The pharmaceutical composition according to any one of items 1 to 112, wherein after discontinuation of the treatment for at least 3 months, preferably at least 6 months, the residual improvement of the β-stiffness is at least 15%, preferably at least 25%, more preferably at least 35%, most preferably at least 45% based on the decrease of the β-stiffness after a period of treatment.

114. The pharmaceutical composition according to any one of items 1 to 113, wherein after discontinuation of the treatment for at least 3 months, preferably at least 6 months, the residual improvement of the β-stiffness
in a subject having a risk for a coronary heart disease (10-year risk) according to the Framingham Risk score of more than 10%, preferably from 10 to 20%, more preferably from 14 to 18%,
is at least 30%, preferably at least 40%, more preferably at least 50%, most preferably at least 60% based on the decrease of the β-stiffness after a period of treatment.

115. The pharmaceutical composition according to any one of items 1 to 113, wherein after discontinuation of the treatment for at least 3 months, preferably at least 6 months, the residual improvement of the β-stiffness
in a subject having a risk for a coronary heart disease (10-year risk) according to the Framingham Risk score of more than 20%, preferably from 20 to 30%, more preferably from 25 to 29%,
is at least 25%, preferably at least 35%, more preferably at least 45%, most preferably at least 55% based on the decrease of the β-stiffness after a period of treatment.

116. The pharmaceutical composition according to any one of items 1 to 113, wherein after discontinuation of the treatment for at least 3 months, preferably at least 6 months, the residual improvement of the β-stiffness in a subject having at least one cardiovascular disorder,
wherein the cardiovascular disorder is preferably post-myocardial infarction,
is at least 40%, preferably at least 50%, more preferably at least 60%, most preferably at least 70% based on the decrease of the β-stiffness after a period of treatment.

117. The pharmaceutical composition according to any one of items 1 to 113, wherein after discontinuation of the treatment for at least 3 months, preferably at least 6 months, the residual improvement of the β-stiffness in a subject having at least one risk factor for a cardiovascular disorder,
wherein the risk factor is a disorder preferably selected from the group consisting of diabetes mellitus type 1, diabetes mellitus type 2, arterial hypertension, hypercholesterolemia and any combinations thereof,
is at least 15%, preferably at least 25%, more preferably at least 35%, most preferably at least 45% based on the decrease of the β-stiffness after a period of treatment.

118. The pharmaceutical composition according to any one of items 1 to 113, or 116, wherein after discontinuation of the treatment for at least 3 months, preferably at least 6 months, the residual improvement of the β-stiffness in a subject having diabetes mellitus type 1 is at least 25%, preferably at least 35%, more preferably at least 45%, most preferably at least 55% based on the decrease of the β-stiffness after a period of treatment.

119. The pharmaceutical composition according to any one of items 1 to 113, or 116, wherein after discontinuation of the treatment for at least 3 months, preferably at least 6 months, the residual improvement of the β-stiffness in a subject having diabetes mellitus type 2 is at least 40%, preferably at least 50%, more preferably at least 60%, most preferably at least 70% based on the decrease of the β-stiffness after a period of treatment.

120. The pharmaceutical composition according to any one of items 1 to 113, wherein after discontinuation of the treatment for at least 3 months, preferably at least 6 months, the residual improvement of the β-stiffness in a subject having at least one risk factor for a cardiovascular disorder,
wherein the risk factor is a risky life style preferably selected from the group consisting of smoking, obesity and a combination thereof, is at least 20%, preferably at least 30%, more preferably at least 40%, most preferably at least 50% based on the decrease of the β-stiffness after a period of treatment.

121. The pharmaceutical composition according to any one of items 1 to 120, wherein the subject is treated over a treatment period of at least one week, preferably, at least 2 weeks, more preferably at least 1 month, still more preferably from about 1 to about 9 months, most preferably from about 1 to about 3 months, particularly preferably about 1 month.

122. The pharmaceutical composition according to any one of items 1 to 121, wherein the subject is treated over at least one intervention-cycle, wherein one intervention-cycle comprises a treatment period of 1 to 9 months of treatment, preferably 1 to 3 months of treatment, more preferably 1 month of treatment, and a rest period of 1 to 12 months of discontinuation of treatment, preferably 1 to 6 months of discontinuation of treatment, more preferably about 6 months of discontinuation of treatment.

123. The pharmaceutical composition according to any one of items 1 to 122, wherein the FMD is still increased by at least 10%, preferably at least 15%, more preferably at least 20%, most preferably at least 25% after 1 month of treatment and after 6 months of discontinuation of treatment.

124. The pharmaceutical composition according to any one of items 1 to 123, wherein the FMD in a subject having diabetes mellitus type 1 is still increased by at least 30%, preferably at least 45%, more preferably at least 54%, most preferably at least 57% after 1 month of treatment and after 6 months of discontinuation of treatment.

125. The pharmaceutical composition according to any one of items 1 to 123, wherein the FMD in a subject having diabetes mellitus type 2 is still increased by at least 60%, preferably at least 80%, more preferably at least 92%, most preferably at least 100% after 1 month of treatment and after 6 months of discontinuation of treatment.

126. The pharmaceutical composition according to any one of items 1 to 125, wherein the PWV is still decreased by at least 1%, preferably at least 1.5%, more preferably at least 2%, most preferably at least 2.1% after 1 month of treatment and after 6 months of discontinuation of treatment.

127. The pharmaceutical composition according to any one of items 1 to 126, wherein the PWV in a subject having diabetes mellitus type 1 is still decreased by at least 2.4%, preferably at least 3.6%, more preferably at least 4.8%, most preferably at least 6.3% after 1 month of treatment and after 6 months of discontinuation of treatment.

128. The pharmaceutical composition according to any one of items 1 to 126, wherein the PWV in a subject having diabetes mellitus type 2 is still decreased by at least 2.8%, preferably at least 4.2%, more preferably at least 5.6%, most preferably at least 7.7% after 1 month of treatment and after 6 months of discontinuation of treatment.

129. The pharmaceutical composition according to any one of items 1 to 128, wherein the β-stiffness is still decreased by at least 0.9%, preferably at least 1.8%, more preferably at least 2.7%, most preferably at least 3.4% after 1 month of treatment and after 6 months of discontinuation of treatment.

130. The pharmaceutical composition according to any one of items 1 to 129, wherein the β-stiffness in a subject having diabetes mellitus type 1 is still decreased by at least 2.2%, preferably at least 3.3%, more preferably at least 4.4%, most preferably at least 5.5% after 1 month of treatment and after 6 months of discontinuation of treatment.

131. The pharmaceutical composition according to any one of items 1 to 129, wherein the β-stiffness in a subject having diabetes mellitus type 2 is still decreased by at least 2.8%, preferably at least 4.2%, more preferably at least 5.6%, most preferably at least 6.3% after 1 month of treatment and after 6 months of discontinuation of treatment.

132. The pharmaceutical composition according to any one of items 1 to 131, comprising a further active agent, preferably selected from the group consisting of an anti-inflammatory agent, an antioxidant, and combinations thereof.

133. The pharmaceutical composition according to any one of items 1 to 132, further comprising an anti-inflammatory agent and an antioxidant, which is not vitamin C or vitamin E.

134. The pharmaceutical composition according to any one of items 1 to 133, further comprising an anti-inflammatory agent, but not comprising an antioxidant.

135. The pharmaceutical composition according to any one of items 1 to 134, further comprising an antioxidant and an anti-inflammatory agent, which is not acetylsalicylic acid.

136. The pharmaceutical composition according to any one of items 1 to 135, further comprising an antioxidant, but not comprising an anti-inflammatory agent.

137. The pharmaceutical composition according to any one of items 1 to 136, further comprising an anti-inflammatory agent and/or an antioxidant, wherein the anti-inflammatory agent is resveratrol, and the antioxidant is coenzyme Q10 or any analogue thereof.

138. The pharmaceutical composition according to any one of items 1 to 137 further comprising one or more pharmaceutically acceptable excipient.

139. The pharmaceutical composition according to any one of items 1 to 138, wherein the composition is in form of an oral dosage form, preferably a solid oral dosage form.

140. A method for
maintaining or improving the functional and morphological properties of the arterial wall,
preventing, reducing or reversing arterial aging, and/or
decreasing the worsening or the occurrence of cardiovascular disorders, in an unhealthy subject, comprising administering to said subject a pharmaceutical composition as defined in any one of items 1 to 139.

141. A method for
maintaining or improving the functional and morphological properties of the arterial wall,
preventing, reducing or reversing arterial aging, and/or
decreasing the worsening or the occurrence of cardiovascular disorders, in a subject having at least one cardiovascular disorder, comprising administering to said subject a pharmaceutical composition as defined in any one of items 1 to 139.

142. A method for
maintaining or improving the functional and morphological properties of the arterial wall,
preventing, reducing or reversing arterial aging, and/or
decreasing the worsening or the occurrence of cardiovascular disorders, in a subject having at least one risk factor for a cardiovascular disorder, comprising administering to said subject a pharmaceutical composition as defined in any one of items 1 to 139.

143. Use of a pharmaceutical composition as defined in any one of items 1 to 139 for the manufacture of a medicament for
maintaining or improving the functional and morphological properties of the arterial wall,
preventing, reducing or reversing arterial aging, and/or
decreasing the worsening or the occurrence of cardiovascular disorders in an unhealthy subject.

144. Use of a pharmaceutical composition as defined in any one of items 1 to 139 for the manufacture of a medicament for
maintaining or improving the functional and morphological properties of the arterial wall,
preventing, reducing or reversing arterial aging, and/or
decreasing the worsening or the occurrence of cardiovascular disorders in a subject having at least one cardiovascular disorder.

145. Use of a pharmaceutical composition as defined in any one of items 1 to 139 for the manufacture of a medicament for
maintaining or improving the functional and morphological properties of the arterial wall,
preventing, reducing or reversing arterial aging, and/or
decreasing the worsening or the occurrence of cardiovascular disorders in a subject having at least one risk factor for a cardiovascular disorder.

The present invention is illustrated in further detail with reference to the following examples. However, the scope of the present invention is not limited to these examples.

EXAMPLE 1

Patients with Moderate Framingham Risk Score (More than 10-20%)

a) Subjects and Experimental Design

Twenty male individuals, aged 63.9±5.4 years, were included in the study. An inclusion criterion was moderate Framingham risk score (more than 10-20%), disclosing moderate risk for occurrence of cardiovascular diseases (myocardial infarction, stroke) in next 10 years.

Before study they were not taking renin inhibitor, neither angiotensin-converting enzyme, neither angiotensin II receptor antagonist, neither HMG-CoA reductase inhibitor. They have no clinical manifested atherosclerosis.

The treated group (n=10) received a combination of subtherapeutic dose of valsartan—20 mg daily and subtherapeutic dose of fluvastatin sodium—10 mg daily during a period of 1 month (30 days), whereas control group (n=10) received placebo.

All subjects underwent clinical examination, blood pressure measurements (Welch AllynSpiedel&Keller automated sphygmomanometer) and ultrasound measurement of flow-mediated dilation of brachial artery (FMD), pulse-wave velocity (PWV) and β-stiffness of carotid artery at inclusion ($0^{th}$ day) and after 1 month ($30^{th}$ day) and again after 6 months (after discontinuation of treatment). Fasting blood samples were taken at the beginning and at the end of the study for laboratory analysis. Blood glucose, electrolytes and cholesterol analysis were obtained using the VITRO 5.1 FS Chemical system (Ortho Clinical Diagnostics, Inc.).

b) Ultrasound Measurements

Ultrasound measurements were performed by a single examiner using AlokaProSound Alpha 10 echo-machine. Endothelial function was measured by means of FMD on the brachial artery according to FMD guidelines (Corretti M C et al. Guidelines for the ultrasound assessment of endothelial-dependent flow-mediated vasodilation of the brachial artery: a report of the International Brachial Artery Reactivity Task Force. J Am Coll Cardiol 2002; 39: 257-65). The echo-machine continuously tracked and recorded the brachial artery diameter. Following the measurement of baseline brachial artery diameter (1 min), the forearm blood pressure cuff was inflated to 50 mmHg above the systolic pressure for 4 min. After the occlusion period, the cuff was rapidly deflated, inducing reactive hyperemia, and the brachial artery diameter was recorded for 3 min. At the end of the measurement, the machine automatically provided the values of FMD.

The measurements of PWV and β-stiffness were performed on the right common carotid artery. The Aloka ultrasound device was also equipped with special software for automatic determination of the PWV and beta-stiffness through the analysis of pulse waves (Carerj S et al. Normal vascular aging evaluated by a new tool: e-tracking. Eur J Echocardiography 2006; suppl: S 49).

c) Statistical Analysis

All values were expressed as arithmetic mean±SEM and were normally distributed. Differences between values recorded at the beginning ($0^{th}$ day) and at the end of the study ($30^{th}$ day) were determined by one-way analysis of variance (ANOVA). When a significant interaction was present, the Bonferroni post-test was performed. A P-value of less than 0.05 was considered significant. All statistical analyses were performed using Graph Pad Prism 5.0 software.

d) Results

Characteristics of the individuals at the beginning and at the end of the treatment in both groups are shown in Table 1. All participants had a Framingham risk score of more than 10 to 20%, the average Framingham risk score was 16.8%.

TABLE 1

Subject characteristics in the placebo and in the test group

| | Placebo (n = 10) | | Fluvastatin 10 mg/ Valsartan 20 mg (n = 10) | |
|---|---|---|---|---|
| | $0^{th}$ day | $30^{th}$ day | $0^{th}$ day | $30^{th}$ day |
| Systolic BP (mmHg) | 138.0 ± 4.2 | 140.1 ± 3.9 | 141.2 ± 4.1 | 140.0 ± 5.1 |
| Diastolic BP (mmHg) | 86.1 ± 4.0 | 84.8 ± 3.9 | 90.6 ± 3.9 | 89.2 ± 3.6 |
| Heart rate (b.p.m.) | 76.1 ± 3.4 | 75.4 ± 2.3 | 77.2 ± 3.0 | 76.6 ± 4.0 |
| Total cholesterol (mmol/l) | 6.4 ± 0.2 | 6.3 ± 0.2 | 6.5 ± 0.3 | 6.3 ± 0.2 |
| LDL cholesterol (mmol/l) | 4.0 ± 0.4 | 4.1 ± 0.2 | 4.1 ± 0.3 | 4.0 ± 0.4 |
| HDL cholesterol (mmol/l) | 0.9 ± 0.1 | 0.9 ± 0.2 | 0.8 ± 0.2 | 0.9 ± 0.1 |
| Triglycerides (mmol/l) | 2.0 ± 0.2 | 2.1 ± 0.2 | 2.1 ± 0.2 | 2.0 ± 0.4 |
| Plasma glucose (mmol/l) | 5.0 ± 0.3 | 4.9 ± 0.2 | 4.9 ± 0.1 | 4.9 ± 0.2 |

All values are expressed as arithmetic mean ± SEM.
BP: blood pressure;
b.p.m.: beats per minute;
LDL: low-density lipoprotein;
HDL: high-density lipoprotein.

No statistically significant differences in the listed parameters (systolic and diastolic blood pressure, heart rate, total cholesterol, LDL cholesterol, HDL cholesterol, triglycerides and glucose concentration) were observed between the placebo and test groups.

TABLE 2

Functional and structural arterial wall parameters before and after treatment

| | Before treatment | After treatment | Improvement |
|---|---|---|---|
| FMD (%) | 1.4 | 3.3 | +135.7% |
| PWV (m/s) | 6.9 | 6.6 | −4.6% |
| β-stiffness (U) | 9.3 | 8.7 | −6.9% |
| Arterial age according to age-related normogram (years) | 64.0 | 58.0 | −6.0 |

The results presented in Table 2 and FIG. 1 show that FMD increased by 135.7% (P<0.001; FIG. 1A), PWV decreased by 4.6% (FIG. 1B) and β-stiffness of the carotid artery decreased by 6.9% (P<0.05; FIG. 1C) after 1 month treatment period. The improvement was observed in each subject of the test group in all measured ultrasound parameters. No significant changes in described parameters in the placebo group throughout the study were observed.

The results show the improvement in PWV and β-stiffness after 1-month treatment corresponding to the decrease of calculated arterial age by using age-related normograms (according to the methods described in Jurasic M J et al. Beta stiffness—setting age standards. Acta Clin Croat 2009; 48:253-8; and Carerj S. Normal vascular aging evaluated by a new tool e-tracking. Eur J Echocardiography 2006; suppl 1:S49). Overall, 1-month treatment with combination of valsartan—20 mg and fluvastatin sodium—10 mg daily resulted in important decrease of arterial age.

Follow-up ultrasound measurements were repeated after 6 months of therapy discontinuation in all participants.

TABLE 3

Residual improvement expressed in % of effect achieved after 1 month of treatment after 6 months of therapy discontinuation.

| | After rest period of 6 months | Residual improvement |
|---|---|---|
| FMD (%) | 2.9 | 78.9% |
| PWV (m/s) | 6.8 | 67.0% |
| β-stiffness (U) | 8.9 | 66.7% |
| Arterial age according to age-related normogram (years) | 59.8 | −4.2 |

The results of measurements repeated after 6 months of therapy discontinuation revealed an prolonged effect of an improvement (Table 3).

EXAMPLE 2

Patients with High Framingham Risk Score (>20%)

a) Subjects and Experimental Design

Twenty male individuals, aged 65.8±5.4 years, were included in the study. An inclusion criterion was high Framingham risk score (greater than 20%), disclosing high risk for occurrence of cardiovascular diseases (myocardial infarction, stroke) in next 10 years. The average Framingham Risk score was 27.1%.

Before study they were taking renin inhibitor, and/or angiotensin-converting enzyme and/or angiotensin II receptor antagonist, and/or HMG-CoA reductase inhibitor each in a therapeutically effective daily dose. They were not taking valsartan and/or fluvastatin.

The treated group (n=10) received a combination of subtherapeutic dose of valsartan—20 mg daily and subtherapeutic dose of fluvastatin sodium—10 mg daily during a period of 1 month (30 days), whereas control group (n=10) received placebo.

All subjects underwent clinical examination, blood pressure measurements (Welch AllynSpiedel&Keller automated sphygmomanometer) and ultrasound measurement of flow-mediated dilation of brachial artery (FMD), pulse-wave velocity (PWV) and β-stiffness of carotid artery at inclusion ($0^{th}$ day) and after 1 month ($30^{th}$ day) and again after 6 months (after discontinuation of treatment). Fasting blood samples were taken at the beginning and at the end of the study for laboratory analysis. Blood glucose, electrolytes and cholesterol analysis were obtained using the VITRO 5.1 FS Chemical system (Ortho Clinical Diagnostics, Inc.).

b) Ultrasound Measurements

Ultrasound measurements were performed by a single examiner using AlokaProSound Alpha 10 echo-machine. Endothelial function was measured by means of FMD on the brachial artery according to FMD guidelines (Corretti M C et al. Guidelines for the ultrasound assessment of endothelial-dependent flow-mediated vasodilation of the brachial artery: a report of the International Brachial Artery Reactivity Task Force. J Am Coll Cardiol 2002; 39: 257-65). The echo-machine continuously tracked and recorded the brachial artery diameter. Following the measurement of baseline brachial artery diameter (1 min), the forearm blood pressure cuff was inflated to 50 mmHg above the systolic pressure for 4 min. After the occlusion period, the cuff was rapidly deflated, inducing reactive hyperemia, and the brachial artery diameter was recorded for 3 min. At the end of the measurement, the machine automatically provided the values of FMD.

The measurements of PWV and β-stiffness were performed on the right common carotid artery. The Aloka ultrasound device was also equipped with special software for automatic determination of the PWV and beta-stiffness through the analysis of pulse waves (Carerj S et al. Normal vascular aging evaluated by a new tool: e-tracking. Eur J Echocardiography 2006; suppl: S 49).

c) Statistical Analysis

All values were expressed as arithmetic mean±SEM and were normally distributed. Differences between values recorded at the beginning ($0^{th}$ day) and at the end of the study ($30^{th}$ day) were determined by one-way analysis of variance (ANOVA). When a significant interaction was present, the Bonferroni post-test was performed. A P-value of less than 0.05 was considered significant. All statistical analyses were performed using Graph Pad Prism 5.0 software.

d) Results

Characteristics of the individuals at the beginning and at the end of the treatment in both groups are shown in Table 4.

TABLE 4

Subject characteristics in the placebo and in the test group

| | Placebo (n = 10) | | Fluvastatin sodium 10 mg/Valsartan 20 mg (n = 10) | |
|---|---|---|---|---|
| | $0^{th}$ day | $30^{th}$ day | $0^{th}$ day | $30^{th}$ day |
| Systolic BP (mmHg) | 145.0 ± 5.4 | 140.0 ± 4.5 | 149.1 ± 5.2 | 146.0 ± 4.4 |
| Diastolic BP (mmHg) | 95.0 ± 3.1 | 92.4 ± 3.4 | 96.0 ± 3.5 | 95.1 ± 4.2 |

TABLE 4-continued

Subject characteristics in the placebo and in the test group

| | Placebo (n = 10) | | Fluvastatin sodium 10 mg/Valsartan 20 mg (n = 10) | |
|---|---|---|---|---|
| | 0th day | 30th day | 0th day | 30th day |
| Heart rate (b.p.m.) | 85.0 ± 4.6 | 85.4 ± 3.1 | 84.1 ± 4.5 | 83.1 ± 3.8 |
| Total cholesterol (mmol/l) | 7.5 ± 0.4 | 7.4 ± 0.3 | 7.6 ± 0.4 | 7.4 ± 0.5 |
| LDL cholesterol (mmol/l) | 4.2 ± 0.5 | 4.3 ± 0.4 | 4.7 ± 0.4 | 4.6 ± 0.5 |
| HDL cholesterol (mmol/l) | 0.8 ± 0.2 | 0.8 ± 0.1 | 0.7 ± 0.1 | 0.7 ± 0.2 |
| Triglycerides (mmol/l) | 2.3 ± 0.3 | 2.2 ± 0.3 | 2.4 ± 0.3 | 2.3 ± 0.3 |
| Plasma glucose (mmol/l) | 4.9 ± 0.1 | 4.9 ± 0.3 | 5.0 ± 0.2 | 4.9 ± 0.3 |

All values are expressed as arithmetic mean ± SEM.
BP: blood pressure;
b.p.m.: beats per minute;
LDL: low-density lipoprotein;
HDL: high-density lipoprotein.

No statistically significant differences in the listed parameters (systolic and diastolic blood pressure, heart rate, total cholesterol, LDL cholesterol, HDL cholesterol, triglycerides and glucose concentration) were observed between the placebo and test groups.

TABLE 5

Functional and structural arterial wall parameters before and after treatment

| | Before treatment | After treatment | Improvement |
|---|---|---|---|
| FMD (%) | 1.4 | 3.1 | +121.1% |
| PWV (m/s) | 7.2 | 6.9 | −4.3% |
| β-stiffness (U) | 9.5 | 9.1 | −4.4% |
| Arterial age according to age-related normogram (years) | 66.0 | 60.0 | −6.0 |

The results presented in Table 5 and FIG. 2 show that FMD increased by 121.1% (P<0.001; FIG. 2A), PWV decreased by 4.3% (FIG. 2B) and β-stiffness of the carotid artery decreased by 4.4% (FIG. 2C) after 1 month treatment period. The improvement was observed in each subject of the test group in all measured ultrasound parameters. No significant changes in described parameters in the placebo group throughout the study were observed.

The results show the improvement in PWV and β-stiffness after 1 month treatment corresponding to the decrease of calculated arterial age by using age-related normograms (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49). Overall, 1 month treatment with combination of valsartan—20 mg daily and fluvastatin sodium—10 mg daily results in important decrease of arterial age.

Follow-up ultrasound measurements were repeated after 6 months of therapy discontinuation in all participants.

TABLE 6

Residual improvement expressed in % of effect achieved after 1 month of treatment after 6 months of therapy discontinuation.

| | After rest period of 6 months | Residual improvement |
|---|---|---|
| FMD (%) | 2.6 | 70.6% |
| PWV (m/s) | 7.0 | 66.7% |
| β-stiffness (U) | 9.3 | 50.0% |
| Arterial age according to age-related normogram (years) | 62.4 | −3.6 |

The results of measurements repeated after 6 months of therapy discontinuation revealed an prolonged effect of an improvement (Table 6).

EXAMPLE 3

Patients with Diabetes Mellitus Type 1

Study I
a) Subjects and Experimental Design 21 young (on average 38.7 years) patients (11 women and 10 men) with type 1 diabetes mellitus (DM) were included in the study. They all had DM for at least 5 years and were well treated (Hb A1c less than 7% in the last 6 months). Before study they were not taking renin inhibitor, neither angiotensin-converting enzyme, neither angiotensin II receptor antagonist, neither HMG-CoA reductase inhibitor. They have no clinical manifested atherosclerosis.

The pharmaceutical combination composition comprising 20 mg valsartan (as a representative of RAAS inhibitor and angiotensin H receptor antagonist) and 10 mg fluvastatin sodium (as a representative of HMG CoA reductase inhibitor) and following pharmaceutically acceptable excipients microcrystalline cellulose, crospovidone, colloidal anhydrous silica, potassium hydrogen carbonate, magnesium stearate, hydroxypropyl methylcellulose, polyethylene glycol, talc, titanium dioxide and iron oxide was used.

All subjects underwent clinical examination, blood pressure measurements (Welch Allyn Spiedel & Keller automated sphygmomanometer) and ultrasound measurement of flow-mediated dilatation of brachial artery (FMD), pulse-wave velocity (PWV) and (3-stiffness of carotid artery at inclusion ($0^{th}$ day) and after 1 month ($30^{th}$ day) of the study. Fasting blood samples were taken at the beginning and at the end of the study for laboratory analysis. Blood glucose, electrolytes, hsCRP and cholesterol were obtained using the VITRO 5.1 FS Chemical system (Ortho Clinical Diagnostics, Inc.).

b) Ultrasound Measurements

Ultrasound measurements were performed by a single examiner using Aloka ProSound Alpha 10 echo-machine. Endothelial function was measured by means of FMD on the brachial artery according to FMD guidelines (Corretti M C et al. Guidelines for the ultrasound assessment of endothelial-dependent flow-mediated vasodilation of the brachial artery: a report of the International Brachial Artery Reactivity Task Force. J Am Coll Cardiol 2002; 39: 257-65). The echo-machine continuously tracked and recorded the brachial artery diameter. Following the measurement of baseline brachial artery diameter (1 min), the forearm blood pressure cuff was inflated to 50 mmHg above the systolic pressure for 4 min. After the occlusion period, the cuff was rapidly deflated, inducing reactive hyperemia, and the brachial artery diameter was recorded for 3 min. At the end of the measurement, the machine automatically provided the values of FMD.

The measurements of PWV and β-stiffness were performed on the right common carotid artery. The Aloka ultrasound device was also equipped with special software for automatic determination of the PWV and beta-stiffness through the analysis of pulse waves (Carerj S et al. Normal vascular aging evaluated by a new tool: e-tracking. Eur J Echocardiography 2006; suppl: S 49).

c) Statistical Analysis

All values were expressed as mean±SEM and were normally distributed. Differences between values recorded at the beginning ($0^{th}$ day) and at the end of the study ($30^{th}$ day) were determined by one-way analysis of variance (ANOVA). When a significant interaction was present, the Bonferroni post-test was performed. A P-value of less than 0.05 was considered significant. All statistical analyses were performed using Graph Pad Prism 5.0 software.

d) Results

TABLE 7

Functional and morphological parameters before and after treatment

|  | Before treatment | After treatment | Improvement |
|---|---|---|---|
| FMD (%) | 1.92 | 3.85 | +100.5% |
| PWV (m/s) | 6.00 | 5.41 | −10.9% |
| β-stiffness (U) | 7.31 | 6.64 | −10.1% |
| Arterial age according to age-related normogram (years) | 52.0 | 41.0 | −11.0 |

The results presented in Table 7 and FIG. 4 show that FMD increased by 100.5% (P<0.001; FIG. 4A), PWV decreased by 10.9% (P<0.01; FIG. 4B) and β-stiffness of the carotid artery decreased by 10.1% (P<0.001; FIG. 4C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II a) Subjects and Experimental Design

Forty individuals (12 women and 28 men) with type 1 diabetes mellitus, aged 36.4±4.1 years were included in the study. Inclusion criteria were type 1 diabetes mellitus duration of at least 5 years, stable and approximately the same dose of insulin and good treatment (levels of HbA1c below 7.5% for the last 6 months). They were not taking angiotensin-converting enzyme or angiotensin II receptor antagonist and/or HMG-CoA reductase inhibitor before the study. They had no clinical manifested atherosclerosis.

The treated group (n=22) received a combination of subtherapeutic dose of valsartan—20 mg daily and subtherapeutic dose of fluvastatin sodium—10 mg daily during a period of 1 month (30 days), whereas control group (n=18) received placebo.

The same ultrasound measurements and the same statistical analysis as in Examples 1 and 2 were performed.

b) Results

TABLE 8

Functional and structural arterial wall parameters before and after treatment

|  | Before treatment | After treatment | Improvement |
|---|---|---|---|
| FMD (%) | 3.0 | 5.4 | +80.0% |
| PWV (m/s) | 5.8 | 5.4 | −7.4% |
| β-stiffness (U) | 6.0 | 5.3 | −13.2% |
| Arterial age according to age-related normogram (years) | 40.0 | 32.0 | −8.0 |

The results presented in Table 8 and FIG. 3 show that FMD increased by 80.0% (P<0.001; FIG. 3A), PWV decreased by 7.4% and β-stiffness of the carotid artery decreased by 13.2% (P<0.05; FIG. 3B and FIG. 3C) after 1 month treatment period. The improvement was observed in each subject of the test group in all measured ultrasound parameters. No significant changes in described parameters in the placebo group throughout the study were observed.

The results show the improvement in PWV and β-stiffness after 1-month treatment corresponding to the decrease of calculated arterial age by using age-related normograms (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49). Overall, 1-month treatment with combination of valsartan—20 mg daily and fluvastatin sodium—10 mg daily results in important decrease of arterial age.

Study III

Follow-up ultrasound measurements were repeated after 6 months of therapy discontinuation in all participants of study I.

TABLE 9

Residual improvement expressed in % of effect achieved after 1 month of treatment after 6 months of therapy discontinuation.

|  | After rest period of 6 months | Residual improvement |
|---|---|---|
| FMD (%) | 4.5 | 62.5% |
| PWV (m/s) | 5.6 | 50.0% |
| β-stiffness (U) | 5.6 | 57.1% |
| Arterial age according to age-related normogram (years) | 35.1 | −4.6 |

The results of measurements repeated after 6 months of therapy discontinuation clearly revealed an important prolonged effect (Table 9).

EXAMPLE 4

Patients with Diabetes Mellitus Type 2

Study I a) Subjects and Experimental Design 10 male patients (on average 44.7 years) with type 2 diabetes mellitus (DM) were included in the study. They all had DM for at least 5 years and were well treated (Hb A1c less than 7.0% in the last 6 months Before study they were not taking renin inhibitor, neither angiotensin-converting enzyme, neither angiotensin II receptor antagonist, neither HMG-CoA reductase inhibitor. They have no clinical manifested atherosclerosis.

Application of the same pharmaceutical composition as in Example 3, Study I, same ultrasound measurement, same statistical analysis.

b) Results

TABLE 10

Functional and morphological parameters before and after treatment

|  | Before treatment | After treatment | Improvement |
| --- | --- | --- | --- |
| FMD (%) | 2.04 | 4.66 | +128.4% |
| PWV (m/s) | 5.90 | 5.30 | −11.3% |
| β-stiffness (U) | 7.03 | 6.44 | −9.2% |
| Arterial age according to age-related normogram (years) | 46.5 | 37.0 | −9.5 |

The results presented in Table 10 and FIG. 6 show that FMD increased by 128.4% (P<0.001; FIG. 6A), PWV decreased by 11.3% (P<0.01; FIG. 6B) and β-stiffness of the carotid artery decreased by 9.2% (P<0.001; FIG. 6C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II a) Subjects and Experimental Design

Twenty male patients with type 2 diabetes mellitus, aged 48.1±5.2 years were included in the study. They all had diabetes mellitus type II for at least 5 years and were well treated (Hb A1c less than 7.0% in the last 6 months). They were taking angiotensin-converting enzyme or angiotensin II receptor antagonist and/or HMG-CoA reductase inhibitor before the study.

Before study they were not taking renin inhibitor, neither angiotensin-converting enzyme, neither angiotensin II receptor antagonist, neither HMG-CoA reductase inhibitor. They have no clinical manifested atherosclerosis.

The treated group (n=10) received a combination of subtherapeutic dose of valsartan—20 mg daily and subtherapeutic dose of fluvastatin sodium—10 mg daily during a period of 1 month (30 days), whereas control group (n=10) received placebo.

The same ultrasound measurements and the same statistical analysis as in Examples 1 and 2 were performed.

b) Results

TABLE 11

Functional and structural arterial wall parameters before and after treatment

|  | Before treatment | After treatment | Improvement |
| --- | --- | --- | --- |
| FMD (%) | 2.3 | 4.0 | +73.9% |
| PWV (m/s) | 6.3 | 5.8 | −8.6% |
| β-stiffness (U) | 7.3 | 6.8 | −7.4% |
| Arterial age according to age-related normogram (years) | 49.0 | 42.0 | −7.0 |

The results presented in Table 11 and FIG. 5 show that FMD increased by 73.9% (P<0.001, FIG. 5A), PWV decreased by 8.6% (P<0.05; FIG. 5B) and β-stiffness of the carotid artery decreased by 7.4% (FIG. 5C) after 1 month treatment period. The improvement was observed in each subject of the test group in all measured ultrasound parameters. No significant changes in described parameters in the placebo group throughout the study were observed.

The results show the improvement in PWV and β-stiffness after 1 month treatment corresponding to the decrease of calculated arterial age by using age-related normograms (according to the methods described in Jurasic M J et al. Beta stiffness—setting age standards. Acta Clin Croat 2009; 48:253-8; and Carerj S. Normal vascular aging evaluated by a new tool:e-tracking. Eur J Echocardiography 2006; suppl 1:S49). Overall, 1 month treatment with a combination of valsartan—20 mg daily and fluvastatin sodium—10 mg daily results in important decrease of arterial age.

Study III

Follow-up ultrasound measurements were repeated after 6 months of therapy discontinuation in all participants of study I.

TABLE 12

Residual improvement expressed in % of effect achieved after 1 month of treatment after 3 months of therapy discontinuation.

|  | After rest period of 3 months | Residual improvement |
| --- | --- | --- |
| FMD (%) | 3.7 | 82.4% |
| PWV (m/s) | 5.9 | 80.0% |
| β-stiffness (U) | 6.9 | 80.0% |
| Arterial age according to age-related normogram (years) | 43.6 | −5.4 |

The results of measurements repeated after 6 months of therapy discontinuation revealed an prolonged effect of an improvement (Table 12).

EXAMPLE 5

Post-Myocardial Infarction Patients (Patients with Coronary Artery Disease)

Study I a) Subjects and Experimental Design 3 male patients (on average 46.6 years) post-myocardial infarction were included in the study.

Application of the same pharmaceutical composition as in Example 3, Study I, same ultrasound measurement, same statistical analysis.

b) Results

TABLE 13

Functional and morphological parameters before and after treatment

|  | Before treatment | After treatment | Improvement |
| --- | --- | --- | --- |
| FMD (%) | 1.64 | 3.95 | +140.9% |
| PWV (m/s) | 7.61 | 6.90 | −10.3% |
| β-stiffness (U) | 8.83 | 8.00 | −10.4% |
| Arterial age according to age related normogram (years) | 63.0 | 55.0 | −8.0 |

The results presented in Table 13 and FIG. 8 show that FMD increased by 140.9% (P<0.001; FIG. 8A), PWV decreased by 10.3% (P<0.01; FIG. 8B) and β-stiffness of the carotid artery decreased by 10.4% (P<0.001; FIG. 8C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II a) Subjects and Experimental Design

Thirteen post-myocardial infarction male patients aged 47.2±4.1 years were included in the study.

Before study they were taking renin inhibitor, and/or angiotensin-converting enzyme and/or angiotensin II receptor antagonist, and/or HMG-CoA reductase inhibitor each in a therapeutically effective daily dose. They were not taking valsartan and/or fluvastatin.

The control group (n=5) received placebo, while the test group (n=10) received subtherapeutic daily dose of valsartan—20 mg daily and subtherapeutic daily dose of fluvastatin sodium—10 mg daily during a period of 1 month—30 days.

The same ultrasound measurements and the same statistical analysis as in Examples 1 and 2 were performed.

b) Results

TABLE 14

Functional and structural arterial wall parameters before and after treatment

| | Before treatment | After treatment | Improvement |
|---|---|---|---|
| FMD (%) | 3.2 | 5.4 | +68.7% |
| PWV (m/s) | 6.0 | 5.6 | −7.1% |
| β-stiffness (U) | 7.7 | 7.2 | −6.9% |
| Arterial age according to age-related normogram (years) | 49.0 | 43.0 | −6.0 |

The results presented in Table 14 and FIG. 7 show that FMD increased by 68.7% (P<0.001; FIG. 7A), PWV decreased by 7.1% (FIG. 7B) and β-stiffness of the carotid artery decreased by 6.9% (FIG. 7C) after 1 month treatment period. The improvement was observed in each subject of the test group in all measured ultrasound parameters. No significant changes in described parameters in the placebo group throughout the study were observed.

The results show the improvement in PWV and β-stiffness after 1 month treatment corresponding to the decrease of calculated arterial age by using age-related normograms (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49). Overall, 1 month treatment with a combination of valsartan—20 mg daily and fluvastatin sodium—10 mg daily results in decrease of arterial age.

Study III

Follow-up ultrasound measurements were repeated after 6 months of therapy discontinuation in all participants of study I.

TABLE 15

Residual improvement expressed in % of effect achieved after 1 month of treatment after 3 months of therapy discontinuation.

| | After rest period of 3 months | Residual improvement |
|---|---|---|
| FMD (%) | 5.0 | 81.8% |
| PWV (m/s) | 5.7 | 75.0% |

TABLE 15-continued

Residual improvement expressed in % of effect achieved after 1 month of treatment after 3 months of therapy discontinuation.

| | After rest period of 3 months | Residual improvement |
|---|---|---|
| β-stiffness (U) | 7.3 | 80.0% |
| Arterial age according to age-related normogram (years) | 44.6 | −4.4 |

The results of measurements repeated after 6 months of therapy discontinuation revealed an prolonged effect of an improvement (Table 15).

EXAMPLE 6

Patients with Arterial Hypertension

Study I a) Subjects and Experimental Design 3 male patients (on average 50.1 years) with arterial hypertension Framingham Risk score 12.0% were included in the study.

Application of the same pharmaceutical composition as in Example 3, Study I, same ultrasound measurement, same statistical analysis.

b) Results

TABLE 16

Functional and morphological parameters before and after treatment

| | Before treatment | After treatment | Improvement |
|---|---|---|---|
| FMD (%) | 1.91 | 3.14 | +64.4% |
| PWV (m/s) | 6.20 | 5.93 | −4.5% |
| β-stiffness (U) | 8.73 | 8.10 | −7.8% |
| Arterial age according to age-related normogram (years) | 55.0 | 48.5 | −6.5 |

The results presented in Table 16 and FIG. 9 show that FMD increased by 64.4% (P<0.001; FIG. 9A), PWV decreased by 4.5% (P<0.01; FIG. 9B) and n-stiffness of the carotid artery decreased by 7.8% (P<0.001; FIG. 9C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II

Follow-up ultrasound measurements were repeated after 6 months of therapy discontinuation in all participants of study I.

TABLE 17

Residual improvement expressed in % of effect achieved after 1 month of treatment after 6 months of therapy discontinuation.

| | After rest period of 6 months | Residual improvement |
|---|---|---|
| FMD (%) | 2.7 | 66.7% |
| PWV (m/s) | 6.0 | 66.7% |

TABLE 17-continued

Residual improvement expressed in % of effect achieved after 1 month of treatment after 6 months of therapy discontinuation.

|  | After rest period of 6 months | Residual improvement |
|---|---|---|
| β-stiffness (U) | 8.4 | 50.0% |
| Arterial age according to age-related normogram (years) | 51.0 | −4.0 |

The results of measurements repeated after 6 months of therapy discontinuation revealed an prolonged effect of an improvement (Table 17).

EXAMPLE 7

Patients with Hypercholesterolemia

Study I
a) Subjects and Experimental Design
3 male patients (on average 48.1 years) with hypercholesterolemia Framingham Risk score 14.1% were included in the study.
Application of the same pharmaceutical composition as in Example 3, Study I, same ultrasound measurement, same statistical analysis.
b) Results

TABLE 18

Functional and morphological parameters before and after treatment

|  | Before treatment | After treatment | Improvement |
|---|---|---|---|
| FMD (%) | 1.90 | 3.74 | +96.8% |
| PWV (m/s) | 6.22 | 5.70 | −9.1% |
| β-stiffness (U) | 7.91 | 7.34 | −7.8% |
| Arterial age according to age related normogram (years) | 51.0 | 45.0 | −6.0 |

The results presented in Table 18 and FIG. 10 show that FMD increased by 96.8% (P<0.001; FIG. 10A), PWV decreased by 9.1% (P<0.01; FIG. 10B) and n-stiffness of the carotid artery decreased by 7.8% (P<0.001; FIG. 10C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II
Follow-up ultrasound measurements were repeated after 6 months of therapy discontinuation in all participants of study I.

TABLE 19

Residual improvement expressed in % of effect achieved after 1 month of treatment after 6 months of therapy discontinuation.

|  | After rest period of 6 months | Residual improvement |
|---|---|---|
| FMD (%) | 2.8 | 50.0% |
| PWV (m/s) | 5.9 | 60.0% |
| β-stiffness (U) | 7.6 | 55.0% |
| Arterial age according to age-related normogram (years) | 47.9 | −3.1 |

The results of measurements repeated after 6 months of therapy discontinuation revealed an prolonged effect of an improvement (Table 19).

EXAMPLE 8

Participants with Risk Factor for CVD—Smoking

Study I
a) Subjects and Experimental Design
3 male patients (on average 46.1 years) exposed to smoking Framingham Risk score 16.9% (CHD risk factor, 10 years) were included in the study.
Application of the same pharmaceutical composition as in Example 3, Study I, same ultrasound measurement, same statistical analysis.
b) Results

TABLE 20

Functional and morphological parameters before and after treatment

|  | Before treatment | After treatment | Improvement |
|---|---|---|---|
| FMD (%) | 2.00 | 5.21 | +160.5% |
| PWV (m/s) | 6.11 | 5.73 | −6.6% |
| β-stiffness (U) | 7.63 | 6.91 | −10.4% |
| Arterial age according to age-related normogram (years) | 50.0 | 43.0 | −7.0 |

The results presented in Table 20 and FIG. 11 show that FMD increased by 160.5% (P<0.001; FIG. 11A), PWV decreased by 6.6% (P<0.01; FIG. 11B) and β-stiffness of the carotid artery decreased by 10.4% (P<0.001; FIG. 11C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II
Follow-up ultrasound measurements were repeated after 6 months of therapy discontinuation in all participants of study I.

TABLE 21

Residual improvement expressed in % of effect achieved after 1 month of treatment after 6 months of therapy discontinuation.

|  | After rest period of 6 months | Residual improvement |
|---|---|---|
| FMD (%) | 3.7 | 53.1% |
| PWV (m/s) | 5.9 | 50.0% |

TABLE 21-continued

Residual improvement expressed in % of effect achieved after 1 month of treatment after 6 months of therapy discontinuation.

|  | After rest period of 6 months | Residual improvement |
|---|---|---|
| β-stiffness (U) | 7.2 | 57.1% |
| Arterial age according to age-related normogram (years) | 46.4 | −3.6 |

The results of measurements repeated after 6 months of therapy discontinuation revealed an prolonged effect of an improvement (Table 21).

EXAMPLE 9

Participants with Risk Factor for CVD—Obesity

Study I
a) Subjects and Experimental Design
3 male obese patients (on average 46.8 years; BMI>30.0) with arterial hypertension and with the average Framingham Risk score 14.0% (CHD risk factor, 10 years) were included in the study.
Application of the same pharmaceutical composition as in Example 3, Study I, same ultrasound measurement, same statistical analysis.
b) Results

TABLE 22

Functional and morphological parameters before and after treatment

|  | Before treatment | After treatment | Improvement |
|---|---|---|---|
| FMD (%) | 2.10 | 5.30 | +152.4% |
| PWW (m/s) | 6.03 | 5.66 | −6.5% |
| β-stiffness (U) | 7.70 | 7.12 | −8.1% |
| Arterial age according to age related normogram (years) | 49.0 | 42.5 | −6.5 |

The results presented in Table 22 and FIG. 12 show that FMD increased by 152.4% (P<0.001; FIG. 12A), PWV decreased by 6.5% (P<0.01; FIG. 12B) and β-stiffness of the carotid artery decreased by 8.1% (P<0.001; FIG. 12C) after 1 month treatment period. The substantial improvement was observed in each subject of the test group in all measured ultrasound parameters. Moreover, the arterial age calculated by age-related normogram (according to the methods described in Jurasic M J et al. Beta stiffness—setting age standards. Acta Clin Croat 2009; 48:253-8; and Carerj S. Normal vascular aging evaluated by a new tool: e-tracking. Eur J Echocardiography 2006; suppl 1:S49.) substantially decreased.

Study II
Follow-up ultrasound measurements were repeated after 6 months of therapy discontinuation in all participants of study I.

TABLE 23

Residual improvement expressed in % of effect achieved after 1 month of treatment after 6 months of therapy discontinuation.

|  | After rest period of 6 months | Residual improvement |
|---|---|---|
| FMD (%) | 4.1 | 62.5% |
| PWV (m/s) | 5.8 | 50.0% |

TABLE 23-continued

Residual improvement expressed in % of effect achieved after 1 month of treatment after 6 months of therapy discontinuation.

|  | After rest period of 6 months | Residual improvement |
|---|---|---|
| β-stiffness (U) | 7.4 | 50.0% |
| Arterial age according to age-related normogram (years) | 45.0 | −4.0 |

The results of measurements repeated after 6 months of therapy discontinuation revealed an prolonged effect of an improvement (Table 23).

The invention claimed is:

1. A method for using a pharmaceutical composition comprising
administering to a subject a subtherapeutic dose of the pharmaceutical composition by a treatment regime comprising at least one intervention-cycle, wherein one intervention-cycle comprises a treatment period of 1 week to 9 months of treatment and a rest period of 1 to 12 months of discontinuation of treatment, wherein the intervention-cycle is repeated, wherein the (a) functional and morphological properties of an arterial wall in the subject are maintained or improved, (b) arterial aging in the subject is prevented, reduced, or reversed, (c) worsening or occurrence of cardiovascular disorders in the subject are decreased, or a combination thereof,
wherein the subject comprises at least one cardiovascular disorder or at least one risk factor for a cardiovascular disorder or a risk for a coronary heart disease (10-year risk) according to the Framingham Risk Score of more than 10%
wherein the cardiovascular disorder is selected from the group consisting of ischemic heart disease, carotid and intracerebral artery disease, peripheral arterial disease, aortic aneurism, and any combinations thereof, or
wherein the risk factor for a cardiovascular disorder is a disorder selected from the group consisting of diabetes, metabolic syndrome, hypercholesterolemia, hypertension, chronic inflammatory disorder, psoriasis, and any combinations thereof, or
wherein the risk factor for a cardiovascular disorder is a risky life style selected from the group consisting of smoking, obesity, and a combination thereof,
and wherein the pharmaceutical composition comprises:
at least one renin-angiotensin-aldosterone system inhibitor in a subtherapeutic daily dose, wherein the subtherapeutic daily dose of the at least one renin-angiotensin-aldosterone system inhibitor does not change the systolic and/or diastolic blood pressure by more than 15%, wherein the at least one renin-angiotensin-aldosterone system inhibitor is an angiotensin II receptor antagonist selected from the group consisting of azilsartan, losartan, eprosartan, irbesartan, olmesartan, candesartan, valsartan, telmisartan and any pharmaceutically acceptable salt or ester thereof and combinations thereof, and
at least one HMG-CoA reductase inhibitor in a subtherapeutic daily dose, wherein the subtherapeutic daily dose of the at least one HMG-CoA reductase inhibitor does not change the LDL cholesterol level in a subject by more than 15%, wherein the at least one HMG-CoA reductase inhibitor is selected from the group consisting of mevastatin, pitavastatin, lovastatin, simvastatin, pravastatin, fluvastatin, atorvastatin, cerivastatin, rosuvastatin, and any pharmaceutically acceptable salt or ester thereof, and combinations thereof.

2. The method according to claim 1, wherein the sub-therapeutic daily dose of the HMG-CoA reductase inhibitor is between 1 to 40 mg.

3. The method according to claim 1, wherein the subject is a human subjects.

4. The method according to claim 1, wherein
the maintaining or improving the functional and morphological properties of the arterial wall,
the prevention, reduction or reversal of arterial aging, or
the decreasing the worsening or the occurrence of cardiovascular disorders, or a combination thereof is achieved after treatment period for at least 1 week.

5. The method according to claim 1, wherein the subject is treated over a treatment period of from about 1 to about 9 months.

6. The method according to claim 1, wherein the subject is treated over at least one intervention-cycle, wherein one intervention-cycle comprises a treatment period of 1 to 9 months of treatment, and a rest period of 1 to 6 months of discontinuation of treatment.

* * * * *